United States Patent
Tanaka et al.

(10) Patent No.: US 10,532,065 B2
(45) Date of Patent: Jan. 14, 2020

(54) BISPHOSPHONIC ACID DERIVATIVE AND APPLICATION FOR SAME

(71) Applicant: NAGASAKI UNIVERSITY, Nagasaki-shi, Nagasaki (JP)

(72) Inventors: Yoshimasa Tanaka, Nagasaki (JP); Kenji Matsumoto, Kyoto (JP); Kosuke Hayashi, Kyoto (JP); Yuki Sakai, Nagasaki (JP); Nagahiro Minato, Kyoto (JP)

(73) Assignee: NAGASAKI UNIVERSITY, Nagasaki (JP)

( * ) Notice: Subject to any disclaimer, the term of this patent is extended or adjusted under 35 U.S.C. 154(b) by 0 days.

(21) Appl. No.: 15/537,398

(22) PCT Filed: Dec. 18, 2015

(86) PCT No.: PCT/JP2015/085590
§ 371 (c)(1),
(2) Date: Jun. 16, 2017

(87) PCT Pub. No.: WO2016/098904
PCT Pub. Date: Jun. 23, 2016

(65) Prior Publication Data
US 2017/0360811 A1    Dec. 21, 2017

(30) Foreign Application Priority Data

Dec. 19, 2014 (JP) .................................. 2014-257451

(51) Int. Cl.
| | | |
|---|---|---|
| A61K 31/675 | (2006.01) |
| C07F 9/6503 | (2006.01) |
| C07F 9/60 | (2006.01) |
| C07F 9/6524 | (2006.01) |
| C07F 9/653 | (2006.01) |
| C07F 9/6539 | (2006.01) |
| C07F 9/6561 | (2006.01) |
| A61K 47/69 | (2017.01) |
| A61K 45/06 | (2006.01) |
| C07F 9/48 | (2006.01) |

(52) U.S. Cl.
CPC ............ *A61K 31/675* (2013.01); *A61K 45/06* (2013.01); *A61K 47/6951* (2017.08); *C07F 9/48* (2013.01); *C07F 9/60* (2013.01); *C07F 9/653* (2013.01); *C07F 9/6524* (2013.01); *C07F 9/65031* (2013.01); *C07F 9/6539* (2013.01); *C07F 9/6561* (2013.01); *C07F 9/65395* (2013.01)

(58) Field of Classification Search
None
See application file for complete search history.

(56) References Cited

U.S. PATENT DOCUMENTS

| | | |
|---|---|---|
| 5,283,057 A | 2/1994 | Shinoda |
| 5,635,495 A | 6/1997 | White et al. |
| 5,710,268 A | 1/1998 | Wimmer |
| 5,719,303 A | 2/1998 | Yoshida et al. |
| 7,358,361 B2 | 4/2008 | Sanders et al. |
| 7,687,482 B2 | 3/2010 | Oldfield et al. |
| 7,745,422 B2 | 6/2010 | Sanders et al. |
| 8,012,949 B2 | 9/2011 | Oldfield et al. |
| 8,071,573 B2 | 12/2011 | Sanders et al. |
| 9,493,582 B2 | 11/2016 | Antle et al. |
| 2005/0113331 A1 | 5/2005 | Prniak et al. |
| 2006/0079487 A1 | 4/2006 | Sanders et al. |
| 2007/0275931 A1 | 11/2007 | Oldfield et al. |
| 2008/0255070 A1 | 10/2008 | Oldfield et al. |
| 2008/0318906 A1 | 12/2008 | Sanders et al. |
| 2010/0316676 A1 | 12/2010 | Sanders et al. |
| 2011/0130370 A1 | 6/2011 | Briault et al. |
| 2015/0045311 A1 | 2/2015 | Antle |
| 2017/0158781 A1 | 6/2017 | Antle et al. |

FOREIGN PATENT DOCUMENTS

| | | |
|---|---|---|
| JP | H01-196255 A | 8/1989 |
| JP | H02-227044 A | 9/1990 |
| JP | H07-149801 A | 6/1995 |
| JP | H08-508245 A | 9/1996 |
| JP | 2009-530414 A | 8/2009 |
| JP | 2010-523709 A | 7/2010 |
| JP | 2011-111458 A | 6/2011 |
| WO | WO 1994/009017 A1 | 4/1994 |
| WO | WO 2005/023270 A2 | 3/2005 |
| WO | WO 2007/076091 A2 | 7/2007 |

(Continued)

OTHER PUBLICATIONS

Silverman, R. "The Organic Chemistry of Drug Design and Drug Action," 2004, Elsevier, pp. 29-32.*

(Continued)

*Primary Examiner* — Heidi Reese

(74) *Attorney, Agent, or Firm* — Leydig, Voit & Mayer, Ltd.

(57) ABSTRACT

The novel bisphosphonic acid ester derivatives represented by the following formula (1):

$$Y-Cy-(NH)_m-(CH_2)_n-C(X)(PO(OR^1)(OR^2))_2 \quad (1)$$

wherein each symbol is as defined in the DESCRIPTION, which has an amino group substituted by a heterocyclic group or a heterocyclic group containing a nitrogen atom, and the acid moiety is esterified with a POM group, an n-butanoyloxymethyl (BuOM) group and the like, exhibit a superior direct or indirect cytotoxicity effect on tumor cells and virus infected cells.

17 Claims, 17 Drawing Sheets

(56) References Cited

FOREIGN PATENT DOCUMENTS

| WO | WO 2009/056952 A1 | 5/2009 |
|---|---|---|
| WO | WO 2013/130666 A1 | 9/2013 |

OTHER PUBLICATIONS

Zhang, Y. et al., J. Med. Chem. (2006), 49(19), pp. 5804-5814.*
Gao et al., "Discovery of potent inhibitor for farnesyl pyrophosphate synthase in the mevalonate pathway," *Chem. Commun.*, 46(29): 5340-5342 (2010).
European Patent Office, Extended European Search Report in European Patent Application No. 15870103.7 (Jun. 29, 2018).
Dunford et al., "Structure-Activity Relationships for Inhibition of Farnesyl Diphosphate Synthase in Vitro and Inhibition of Bone Resorption in Vivo by Nitrogen-Containing Bisphosphonates," *J. Pharmacol. Exp. Ther.*, 296(2): 235-242 (2001).
Ghosh et al., "Effect of Bisphosphonates on the Growth of *Entamoeba histolytica* and *Plasmodium* Species in Vitro and in Vivo," *J. Med. Chem.*, 47(1): 175-187 (2004).
Gnant et al, "Endocrine Therapy plus Zoledronic Acid in Premenopausal Breast Cancer," *N. Engl. J. Med.*, 360(7): 679-691 (2009).
Hounslow et al., "Determination of the Microscopic Equilibrium Dissociation Constants for Risedronate and Its Analogues Reveals Two Distinct Roles for the Nitrogen Atom in Nitrogen-Containing Bisphosphonate Drugs," *J. Med. Chem.*, 51(14): 4170-4178 (2008).
Kunzmann et al., "γ/σT-Cell Stimulation by Pamidronate," *N. Engl. J. Med.*, 340(9): 737-738 (1999).
Lacbay et al., "Modular Assembly of Purine-like Bisphosphonates as Inhibitors of HIV-1 Reverse Transcriptase," *J. Med. Chem.*, 57(17): 7435-7449 (2014).

Mao et al., "Solid-State NMR, Crystallographic, and Computational Investigation of Bisphosphonates and Farnesyl Diphosphate Synthase-Bisphosphonate Complexes," *J. Am. Chem. Soc.*, 128(45): 14485-14497 (2006).
Morgan et al., "First-line treatment with zoledronic acid as compared with clodronic acid with multiple myeloma (MRC Myeloma IX): a randomized controlled trial," *Lancet*, 376(9757): 1989-1999 (2010).
No et al., "Lipophilic analogs of zoledronate and risedronate inhibit *Plasmodium* geranylgeranyl diphosphate synthase (GGPPS) and exhibit potent antimalarial activity," *Pro. Natl. Acad. Sci. U.S.A.*, 109(11): 4058-4063 (2012).
Sanders et al., "3-D QSAR Investigations of the Inhibition of *Leishmania major* Farnesyl Pyrophosphate Synthase by Bisphosphonates," *J. Med. Chem.*, 46(24): 5171-5183 (2003).
Song et al., "Bisphosphonate inhibitors of ATP-mediated HIV-1 reverse transcriptase catalyzed excision of chain-terminating 3'-azido, 3'-deoxythymidine: A QSAR investigation," *Bioorg. Med. Chem.*, 16(19): 8959-8967 (2008).
Wiemer et al., "Pivaloyloxymethyl-modified isoprenoid bisphosphonates display enhanced inhibition of cellular geranylgeranylation," *Bioorg. Med. Chem.*, 16(7): 3652-3660 (2008).
Zhang et al., "Activity of Nitrogen-Containing and Non-Nitrogen-Containing Bisphosphonates on Tumor Cell Lines," *J. Med. Chem.*, 49(19): 5804-5814 (2006).
Japanese Patent Office, International Search Report in International Patent Application No. PCT/JP2015/085590 (Mar. 22, 2016).
Nash, "Cyclodextrins," *Handbook of Pharmaceutical Excipients*, 5$^{th}$ edition [Japanese version], pp. 400-406 (2005).

* cited by examiner $99.48 \times 100/(0.18 + 99.48) = 99.8\%$ $94.37 \times 100/(3.72 + 94.37) = 96.2\%$

BISPHOSPHONIC ACID DERIVATIVE AND APPLICATION FOR SAME

CROSS-REFERENCE TO RELATED APPLICATIONS

This patent application is the U.S. national phase of International Patent Application No. PCT/JP2015/085590, filed on Dec. 18, 2015, which claims the benefit of Japanese Patent Application No. 2014-257451, filed Dec. 19, 2014, the disclosures of which are incorporated herein by reference in their entireties for all purposes.

TECHNICAL FIELD

The present invention relates to novel bisphosphonic acid derivatives and use thereof. More particularly, the present invention relates to bisphosphonic acid ester derivatives and a pharmaceutical composition, an anti-tumor cell agent, an anti-virus-infected cell agent, a lymphocyte-treating agent and the like, each containing said derivative as an active ingredient.

BACKGROUND ART

Bisphosphonic acids are a group of compounds having a P—C—P skeleton, have high affinity for bone tissues and, when incorporated into osteoclasts, show cytotoxicity and suppress bone resorption. Utilizing such properties for therapeutic purposes, they are used as prophylactic or therapeutic drugs for diseases relating to the fragility of bone such as osteoporosis, osteitis deformans, osteogenesis imperfecta and the like. In addition, bisphosphonic acids containing a nitrogen atom in the side chain such as pamidronic acid, alendronic acid, risedronic acid, zoledronic acid and the like are commercially available as drugs for hypercalcemia of malignancy. Recently, moreover, it has been reported that the disease-free survival is significantly extended when zoledronic acid is used as an adjuvant therapy drug in the endocrine therapy and chemotherapy of premenopausal estrogen sensitive early breast cancer cases and multiple myeloma (non-patent documents 1, 2). Accordingly, the relationship between bisphosphonic acid having a nitrogen atom in the side chain and an antitumor effect is suggested, and direct cytotoxicity and/or indirect cytotoxicity via activation of immunocytes on tumor cells are/is considered to be the cause thereof, though a consensus has not been reached regarding the action mechanism thereof.

For example, a part of zoledronic acid administered to a living body enters into the cell by fluid phase endocytosis, is transferred to nucleoside monophosphate, is converted to a nucleoside triphosphate analog compound, and may antagonistically inhibit biological enzyme reaction utilizing high energy phosphate bond of nucleoside triphosphate, which is suggested to injure tumor cells.

Furthermore, intracellularly transferred bisphosphonic acid has been shown to inhibit farnesyl diphosphate synthase involved in the biosynthesis of isoprenoid metabolites such as cholesterol and the like. The enzyme catalyzes a reaction to synthesize geranyl diphosphate from isopentenyl diphosphate and dimethylallyl diphosphate, and a reaction to synthesize farnesyl diphosphate from isopentenyl diphosphate and geranyl diphosphate. Therefore, inhibition of farnesyl diphosphate synthase interferes with the metabolic pathway downstream of geranyl diphosphate, as well as causes accumulation of isopentenyl diphosphate in the cytoplasm. When the biosynthetic pathway downstream of geranyl diphosphate is inhibited, isoprenoid compounds such as cholesterol, liposoluble vitamins, bile acid, lipoprotein and the like are not biosynthesized, and the proliferation of tumor cells is considered to be suppressed.

The isoprenyl group of farnesyl diphosphate and geranylgeranyl diphosphate biosynthesized by farnesyl diphosphate synthase is transferred to, what is called, small G proteins such as Ras, Rho, Rap, Rab, Rac and the like. The small G protein having the transferred isoprenyl group is translocated to a cellular membrane since the isoprenyl group acts as an anchor, and plays an important role in the proliferation, adhesion and the like of cells. In this case, when nitrogen-containing bisphosphonic acids such as zoledronic acid and the like inhibits farnesyl diphosphate synthase, transfer of the isopropenyl group is inhibited, translocation to the membrane of small G protein is prevented, and, as a result, tumor cell proliferation is inhibited.

When farnesyl diphosphate synthase is inhibited, the intracellular concentration of isopentenyl diphosphate as a substrate thereof increases. The increase in the intracellular concentration of isopentenyl diphosphate is detected by a butyrophilin 3A1 transmembrane protein, and the change thereof is recognized by γδ T cells having a Vγ2Vδ2 T cell receptor. As a result, the γδ T cells are degranulated to release perforin and granzyme B, which induce apoptosis of tumor cells and virus infected cells. It is shown that nitrogen-containing bisphosphonic acids efficiently kill tumor cells and virus-infected cells indirectly via the activation of immunocytes.

The direct and indirect toxicity on tumor cells and virus infected cells as mentioned above by the nitrogen-containing bisphosphonic acids is not effectively induced unless the nitrogen-containing bisphosphonic acids enters into the target cells. However, since bisphosphonic acids clinically applicable at present have all been designed and synthesized for the purpose of improving bone-related diseases, their permeability into tumor cells and virus infected cells is markedly low. In fact, the molecules are negatively charged due to an acid structure of P—C—P it has, thus resulting in markedly low permeability into cells.

While it is disclosed that a pivaloyloxymethyl (POM) group ester derivative of bisphosphonic acid having an unsubstituted 2-pyridyl group, specifically, 2-(pyridyl-2-amino)ethylidene-1,1-bisphosphonic acid tetrakispivaloyloxy methyl ester shows cytotoxicity, and suppresses proliferation of tumor cells, the mechanism thereof has not been clarified (non-patent document 3).

In addition, while bisphosphonic acid derivative can be used by dissolving in DMSO and the like in the in vitro experiment system, when it is administered to the living body, it needs to be solubilized in a biotolerable form. Various techniques have been developed as a means to solubilize medicaments. For example, a method using surfactants such as Tween 80, HCO-60 and the like, a method using clathrating agents such as cyclodextrin (hereinafter sometimes to be referred to as "CD") and the like, and the like are known. Patent document 1 discloses a production method of alkylated cyclodextrin, and a method of solubilizing hardly water-soluble medicaments by using alkylated cyclodextrin. The alkylated cyclodextrin described in patent document 1 is a methylated cyclodextrin derivative characteristically having an average substitution rate of 1.7-1.9 as measured by $^1$H-NMR, and the 06-position methylated by 55-75%.

DOCUMENT LIST

Patent Document patent document 1: JP-A-7-149801

Non-Patent Documents non-patent document 1: N. Engl. J. Med., 360(7):679-691 Feb. 12, 2009
non-patent document 2: Lancet 376: 1989-1999 2010
non-patent document 3: J. Med. Chem., 49(19):5804-5814 2006
non-patent document 4: N. Engl. J. Med., 340(9):737-738 Mar. 4, 1999

SUMMARY OF THE INVENTION

Problems to be Solved by the Invention

The problem of the present invention is to provide novel bisphosphonic acid derivatives capable of exhibiting a superior direct and indirect cytotoxicity effect on tumor cells and virus infected cells.

Means of Solving the Problems

The present inventors have conducted intensive studies in an attempt to solve the above-mentioned problem, and found that novel bisphosphonic acids derivative having an amino group substituted by a heterocyclic group or a heterocyclic group containing a nitrogen atom, wherein an acid moiety is esterified with a POM group, an n-butanoyloxymethyl (BuOM) group or the like becomes a prodrug, are easily translocated into various tumor cells and virus infected cells and, as a result, have a high growth suppressive activity and cytotoxicity, which resulted in the completion of the present invention.

Accordingly, the present invention is as shown below.
[1] Bisphosphonic acid ester derivative represented by the following formula (1):

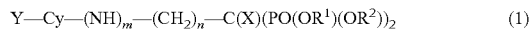

$$Y\text{—}Cy\text{—}(NH)_m\text{—}(CH_2)_n\text{—}C(X)(PO(OR^1)(OR^2))_2 \quad (1)$$

wherein Cy is a phenyl group or a heterocyclic group, Y is a hydrogen atom, an alkyl group, a halogen atom, an alkyl halide group, a hydroxyl group, an aryl group optionally substituted by a halogen atom or an alkoxy group, or an aralkyloxy group, X is a hydrogen atom or a hydroxyl group, $R^1$ and $R^2$ are the same or different from each other and each is a hydrogen atom or an alkylcarbonyloxyalkyl group, at least one of $R^1$ and $R^2$ is an alkylcarbonyloxyalkyl group, m is a number, 0 or 1, and n is an integer of 1-6 (excluding when Cy is a 2-pyridyl group, m is 1, n is 1, X is a hydrogen atom, Y is a hydrogen atom, and $R^1$ and $R^2$ are each a pivaloyloxymethyl group).
[2] The derivative of the above-mentioned [1], wherein, in the formula (1), Cy is a phenyl group.
[3] The derivative of the above-mentioned [1], wherein, in the formula (1), Cy is a 5- to 10-membered heterocyclic group containing 1 to 3 atoms selected from a nitrogen atom, a sulfur atom and an oxygen atom.
[4] The derivative of the above-mentioned [1], wherein, in the formula (1), Cy is a 5- or 6-membered heterocyclic group containing 1 or 2 atoms selected from a nitrogen atom and a sulfur atom.

[5] The derivative of the above-mentioned [1], wherein, in the formula (1), Cy is a thiazolyl group, a pyridyl group, a pyrimidyl group, or a 7-azaindolyl group.
[6] The derivative of any of the above-mentioned [1]-[5], wherein, in the formula (1), X is a hydrogen atom, Y is a hydrogen atom, a $C_{1-3}$ alkyl group, a halogen atom, an alkyl halide group or a phenyl group, and $R^1$ and $R^2$ are each a $C_{2-7}$ alkylcarbonyloxy-$C_{1-3}$ alkyl group.
[7] The derivative of the above-mentioned [1], wherein, in the formula (1), Cy is a thiazolyl group or a pyrimidyl group, X is a hydrogen atom, Y is a hydrogen atom or a halogen atom, and $R^1$ and $R^2$ are each an alkylcarbonyloxyalkyl group.
[8] The derivative of the above-mentioned [1], wherein, in the formula (1), Cy is a thiazolyl group, X is a hydrogen atom, Y is a hydrogen atom or a halogen atom, and $R^1$ and $R^2$ are each an alkylcarbonyloxyalkyl group.
[9] The derivative of the above-mentioned [1], wherein, in the formula (1), Cy is a pyrimidyl group, X is a hydrogen atom, Y is a hydrogen atom or a halogen atom, and $R^1$ and $R^2$ are each an alkylcarbonyloxyalkyl group.
[10] The derivative of the above-mentioned [1], wherein, in the formula (1), Cy is a thiazolyl group or a pyrimidyl group, X is a hydrogen atom, Y is a hydrogen atom or a halogen atom, and $R^1$ and $R^2$ are each a pivaloyloxymethyl (POM) group.
[11] The derivative of the above-mentioned [1], wherein, in the formula (1), Cy is a thiazolyl group, X is a hydrogen atom, Y is a hydrogen atom or a halogen atom, and $R^1$ and $R^2$ are each a pivaloyloxymethyl (POM) group.
[12] The derivative of the above-mentioned [1], wherein, in the formula (1), Cy is a pyrimidyl group, X is a hydrogen atom, Y is a hydrogen atom or a halogen atom, and $R^1$ and $R^2$ are each a pivaloyloxymethyl (POM) group.
[13] The derivative of the above-mentioned [1], wherein, in the formula (1), Cy is a thiazolyl group or a pyrimidyl group, X is a hydrogen atom, Y is a hydrogen atom or a halogen atom, and $R^1$ and $R^2$ are each a butanoyloxymethyl (BuOM) group.
[14] The derivative of the above-mentioned [1], wherein, in the formula (1), Cy is a thiazolyl group, X is a hydrogen atom, Y is a hydrogen atom or a halogen atom, and $R^1$ and $R^2$ are each a butanoyloxymethyl (BuOM) group.
[15] The derivative of the above-mentioned [1], wherein, in the formula (1), Cy is a pyrimidyl group, X is a hydrogen atom, Y is a hydrogen atom or a halogen atom, and $R^1$ and $R^2$ are each a butanoyloxymethyl (BuOM) group.
[16] A pharmaceutical composition comprising the derivative of any of the above-mentioned [1]-[15] as an active ingredient.
[17] A pharmaceutical composition comprising the derivative of any of the above-mentioned [1]-[15] and alkylated cyclodextrin.
[18] The pharmaceutical composition of the above-mentioned [17], wherein the alkylated cyclodextrin is trimethyl-β-cyclodextrin.
[19] The pharmaceutical composition of any of the above-mentioned [16]-[18], which is an anti-tumor cell agent.
[20] The pharmaceutical composition of any of the above-mentioned [16]-[18], which is an anti-virus-infected cell agent.
[21] The pharmaceutical composition of any of the above-mentioned [16]-[18], which is a lymphocyte-treating agent.
[22] A method of dissolving a hardly water-soluble medicament in a solvent, comprising a step of dissolving alkylated cyclodextrin in a water-soluble organic solvent, and a step of mixing a hardly water-soluble medicament with the water-soluble organic solvent dissolving the alkylated cyclodextrin.

[23] The method of the above-mentioned [22], wherein the hardly water-soluble medicament is a bisphosphonic acid ester derivative.

[24] The method of the above-mentioned [23], wherein the bisphosphonic acid ester derivative is the derivative of any of the above-mentioned [1]-[15].

[25] The method of any of the above-mentioned [22]-[24], wherein the alkylated cyclodextrin is trimethyl-β-cyclodextrin.

[26] A method of treating a lymphocyte in a living body, comprising administering an effective amount of the bisphosphonic acid ester derivative of any of the above-mentioned [1]-[15] to the body.

[27] A method of proliferating and/or inducing a γδ T cell, comprising administering an effective amount of the bisphosphonic acid ester derivative of any of the above-mentioned [1]-[15] to a living body.

[28] A method of suppressing proliferation of a tumor cell, comprising administering an effective amount of the bisphosphonic acid ester derivative of any of the above-mentioned [1]-[15] to a living body.

[29] A method of treating cancer, comprising administering an effective amount of the bisphosphonic acid ester derivative of any of the above-mentioned [1]-[15] to a living body.

[30] A method of proliferating and/or inducing a γδ T cell, comprising reacting ex vivo the bisphosphonic acid ester derivative of any of the above-mentioned [1]-[15] with a sample containing γδ T cells.

[31] A method of suppressing proliferation of a tumor cell, comprising a step of reacting the bisphosphonic acid ester derivative of any of the above-mentioned [1]-[15] with a sample containing γδ T cells collected from a living body, and a step of returning the γδ T cells to the living body.

Effect of the Invention

Since the novel bisphosphonic acid ester derivatives of the present invention are efficiently translocated into cells as compared to unesterified bisphosphonic acids, they have high farnesyl diphosphate synthase inhibitory activity. Accordingly, they suppress production of isoprenoid metabolites such as cholesterol, liposoluble vitamin, lipoprotein and the like, essential for the survival of cells, and exhibit a superior direct tumor cytotoxicity effect and a superior virus-infected cell cytotoxicity effect. By efficiently increasing the intracellular level of isopentenyl diphosphate to be a substrate of farnesyl diphosphate synthase, activation of γδ T cells via butyrophilin 3A1 is induced, and an efficient indirect tumor cytotoxicity effect and an efficient virus-infected cell cytotoxicity effect, via an immune effect, are exhibited.

A method of synthesizing the derivatives of the present invention can produce nitrogen-containing bisphosphonic acids esterified with various alkylcarbonyloxyalkyl groups such as a POM group, a BuOM group and the like, in a high yield and efficiently, as compared to conventional methods. That is, vinylidenephosphonic acid POM ester and BuOM ester, obtained by POM esterification or BuOM esterification of vinylidene bisphosphonic acid tetramethylester, can be obtained in a high yield (30%-100%). In addition, since the number of reactions in derivative synthesis can be reduced by simple purification of vinylidenebisphosphonic acid POM ester and BuOM ester, various novel bisphosphonic acid ester derivatives capable of exhibiting superior indirect and direct tumor cytotoxicity action and virus-infected cell cytotoxicity action can be efficiently synthesized.

Furthermore, the derivatives of the present invention can be solubilized by including with a cyclodextrin type clathrating agent. When compared to the use of surfactants such as Tween 80, HC0-60 and the like, and the like, bisphosphonic acid ester derivatives can be solubilized with a small amount of alkylated cyclodextrin, and the solubilized bisphosphonic acid ester derivatives are also superior in the preservation stability.

For solubilization with a surfactant, 100 molar equivalents of a bisphosphonic acid ester derivative are necessary and the content of the surfactant becomes too excessive. In the case of alkylated cyclodextrin, a sufficient solubilization effect was afforded with 10 molar equivalents of a bisphosphonic acid ester derivative. When solubilized with a surfactant, the medicament precipitated when left standing at room temperature for about one week, whereas with alkylated cyclodextrin, precipitation was not observed even after leaving for one week, and superior preservation stability was afforded.

When a medicament is included in cyclodextrin, intracellular transferability is limited, and a sufficient effect cannot be expected in some cases. In the present invention, however, even when included, good intracellular transferability can be maintained, and cytotoxicity against tumor cells and γδ T cell proliferation and/or induction ability of the derivative can be effectively exhibited.

DESCRIPTION OF EMBODIMENTS

Figure 1:
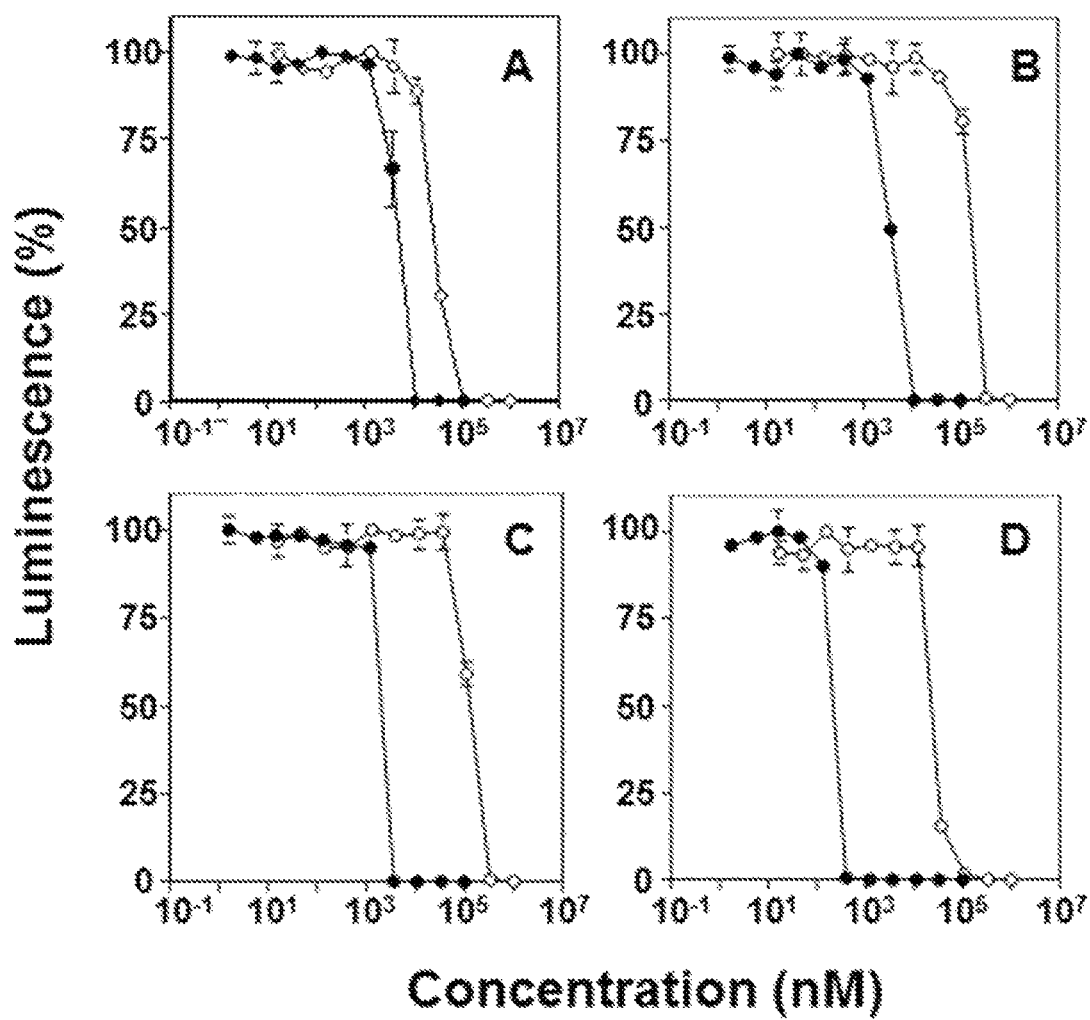
FIG. 1 is a graph showing the results of comparison study of the direct antitumor action of bisphosphonic acid POM ester derivatives (compounds 3, 4, 6, 7) and bisphosphonic acids corresponding thereto (compounds 10, 11, 13, 14) by using monocyte tumor-derived U937 cells.

One embodiment of the bisphosphonic acid ester derivatives used in the present invention is represented by the following formula (1):

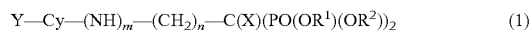

Y—Cy—(NH)$_m$—(CH$_2$)$_n$—C(X)(PO(OR$^1$)(OR$^2$))$_2$     (1)

The bisphosphonic acid ester derivatives represented by the above-mentioned formula (1) do not include a derivative wherein Cy is a 2-pyridyl group, m is 1, n is 1, X is a hydrogen atom, Y is a hydrogen atom, and R$^1$ and R$^2$ are each a pivaloyloxymethyl group, i.e., 2-(pyridyl-2-amino)ethylidene-1,1-bisphosphonic acid tetrakispivaloyloxymethyl ester.

In the above-mentioned formula, Cy is a phenyl group or a heterocyclic group, Y is a hydrogen atom, an alkyl group, a halogen atom, an alkyl halide group, a hydroxyl group, an aryl group optionally substituted by a halogen atom or an alkoxy group, or an aralkyloxy group, X is a hydrogen atom or a hydroxyl group, R$^1$ and R$^2$ are the same or different from each other and each is a hydrogen atom or an alkylcarbonyloxyalkyl group, at least one of $R^1$ and $R^2$ is an alkylcarbonyloxyalkyl group, m is a number, 0 or 1, and n is an integer of 1-6.

Cy is a phenyl group or a heterocyclic group, to which at least Y is bonded. The heterocyclic group is a 4- to 15-membered monocyclic heterocyclic group or condensed polycyclic heterocyclic group containing, as a ring-constituting atom besides carbon atom, 1-4 hetero atoms selected from a nitrogen atom, a sulfur atom and an oxygen atom. Examples of the heterocyclic group include furyl, pyridyl, pyrimidinyl, pyridazinyl, pyrazinyl, pyrrolyl, imidazolyl, pyrazolyl, triazolyl, isothiazolyl, oxazolyl, isoxazolyl, oxadiazolyl, thiadiazolyl, triazolyl, tetrazolyl, triazinyl, quinolyl, isoquinolyl, quinazolyl, quinoxalyl, benzofuryl, benzothienyl, benzoxazolyl, benzisoxazolyl, benzothiazolyl, benzimidazolyl, benzotriazole, indolyl, indazolyl, pyrrolopyrazinyl, imidazopyridinyl, imidazopyrazinyl, pyrazolopyridinyl, pyazolothienyl, pyrazolotriazinyl, oxetanyl, pyrrolidinyl, piperidinyl, morpholinyl, thiomorpholinyl, piperazinyl, hexamethyleniminyl, oxazolidinyl, thiazolidinyl, imidazolidinyl, oxazolinyl, thiazolinyl, imidazolinyl, dioxolanyl, dihydrooxadiazolyl, pyranyl, tetrahydropyranyl, thiopyranyl, tetrahydrothiopyranyl, tetrahydrofuryl, pyrazolidinyl, pyrazolinyl, tetrahydropyrimidinyl, dihydroindolyl, dihydroisoindolyl, dihydrobenzofuranyl, dihydrobenzodioxinyl, dihydrobenzodioxepinyl, tetrahydrobenzofuranyl, chromenyl, dihydroquinolinyl, tetrahydroquinolinyl, dihydroisoquinolinyl, tetrahydroisoquinolinyl, dihydrophthalazinyl, 7-azaindolyl and the like.

Preferably, the above-mentioned heterocyclic group is a 5- to 10-membered heterocyclic group containing 1-3 hetero atoms selected from a nitrogen atom, a sulfur atom and an oxygen atom, more preferably a 5- or 6-membered heterocyclic group containing 1 or 2 hetero atoms selected from a nitrogen atom and a sulfur atom. Such heterocyclic group is specifically preferably thiazolyl, pyridyl, pyrimidyl or 7-azaindolyl, more preferably thiazolyl or pyrimidyl, particularly preferably a 2-thiazolyl group or a 4-pyrimidyl group.

In the above-mentioned heterocyclic group, Y is bonded at a substitutable position. Y is a hydrogen atom, an alkyl group (e.g., $C_{1-10}$ alkyl group such as methyl, ethyl, hexyl, octyl and the like), a halogen atom, (e.g., chlorine atom, fluorine atom, bromine atom), an alkyl halide group (e.g., $C_{1-3}$ alkyl group (e.g., methyl, ethyl, propyl) substituted by 1 to 3 halogen atoms (as defined above), a hydroxyl group, an aryl group, or an aralkyloxy group. As used herein, the aforementioned aryl group is optionally substituted by a halogen atom (as defined above) or an alkoxy group (e.g., $C_{1-3}$ alkoxy group such as methoxy, ethoxy, propoxy and the like). Preferably, Y is a hydrogen atom, a $C_{1-3}$ alkyl group, a halogen atom, an alkyl halide group, an unsubstituted aryl group, more preferably, a hydrogen atom, a methyl group, a halogen atom, a trifluoromethyl group or a phenyl group, most preferably, a hydrogen atom or a bromine atom.

The aryl group encompasses a monocyclic aryl group and a condensed polycyclic aryl group, and specifically, phenyl, biphenyl, naphthyl, anthryl, phenanthryl and acenaphthylenyl can be mentioned. It is preferably a $C_{6-18}$ aryl group, more preferably a $C_{6-8}$ aryl group, particularly preferably a phenyl group.

The aralkyloxy group is preferably a $C_{7-18}$ aralkyloxy group, specifically benzyloxy, phenethyloxy and the like, with preference given to benzyloxy.

$R^1$ and $R^2$ are the same or different from each other and each is a hydrogen atom or an alkylcarbonyloxyalkyl group, and at least one of $R^1$ and $R^2$ is an alkylcarbonyloxyalkyl group. Examples of the alkylcarbonyloxyalkyl group include a $C_{2-7}$ alkylcarbonyloxy-$C_{1-3}$ alkyl group, preferably, $C_{3-4}$ alkylcarbonyloxy-methyl, particularly preferably, pivaloyloxymethyl or n-butanoyloxymethyl. Both $R^1$ and $R^2$ are preferably alkylcarbonyloxyalkyl groups.

m is 0 or 1, preferably 1. In the case wherein Cy is secondary amine such as pyrrolyl, pyrrolidinyl, piperidinyl, morpholinyl, thiomorpholinyl, piperazinyl, hexamethyleniminyl, oxazolidinyl, thiazolidinyl, imidazolidinyl and the like, m is 0, Cy is bonded to —$(CH_2)_n$— group at the nitrogen atom. n is an integer of 1-6, preferably 1-3, particularly preferably 1.

X is a hydrogen atom or a hydroxyl group, preferably a hydrogen atom.

Specific examples of the bisphosphonic acid ester derivative of the present invention include the following compounds.

The numbers in the parentheses in the following structural formulas show compound Nos. In addition, the numbers in the parentheses after the compound names also show compound Nos. The bisphosphonic acid ester derivative of the present invention is preferably a compound of compound No. 5, 6, 7, 34, 39, 43 or 44.

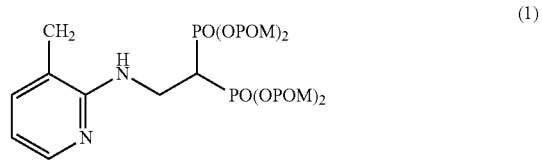

(1)

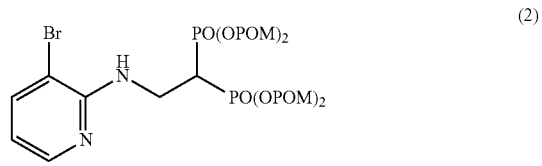

(2)

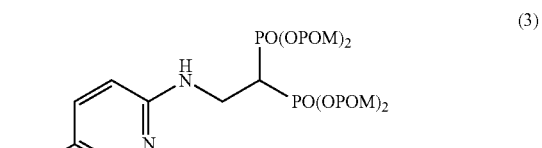

(3)

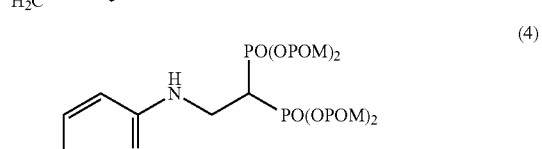

(4)

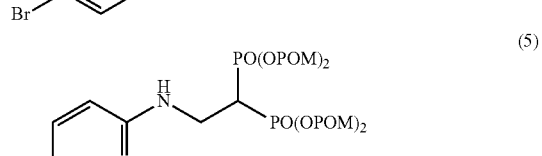

(5)

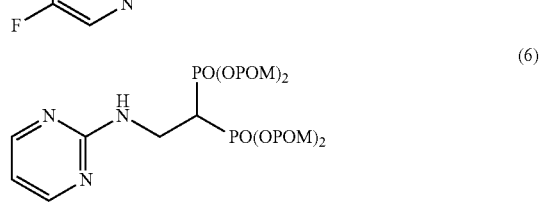

(6)

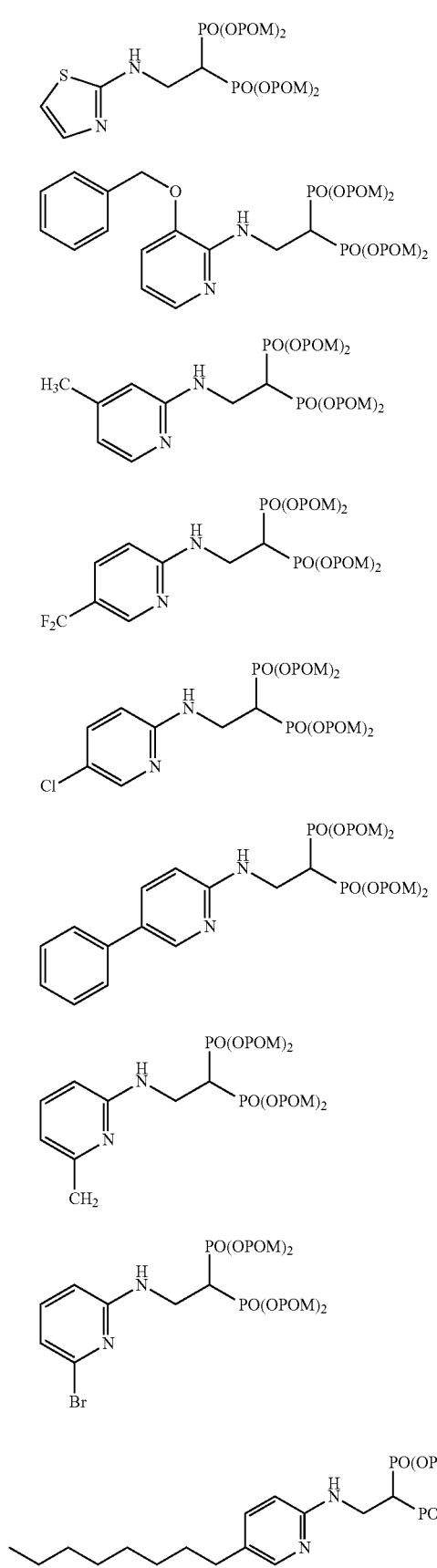
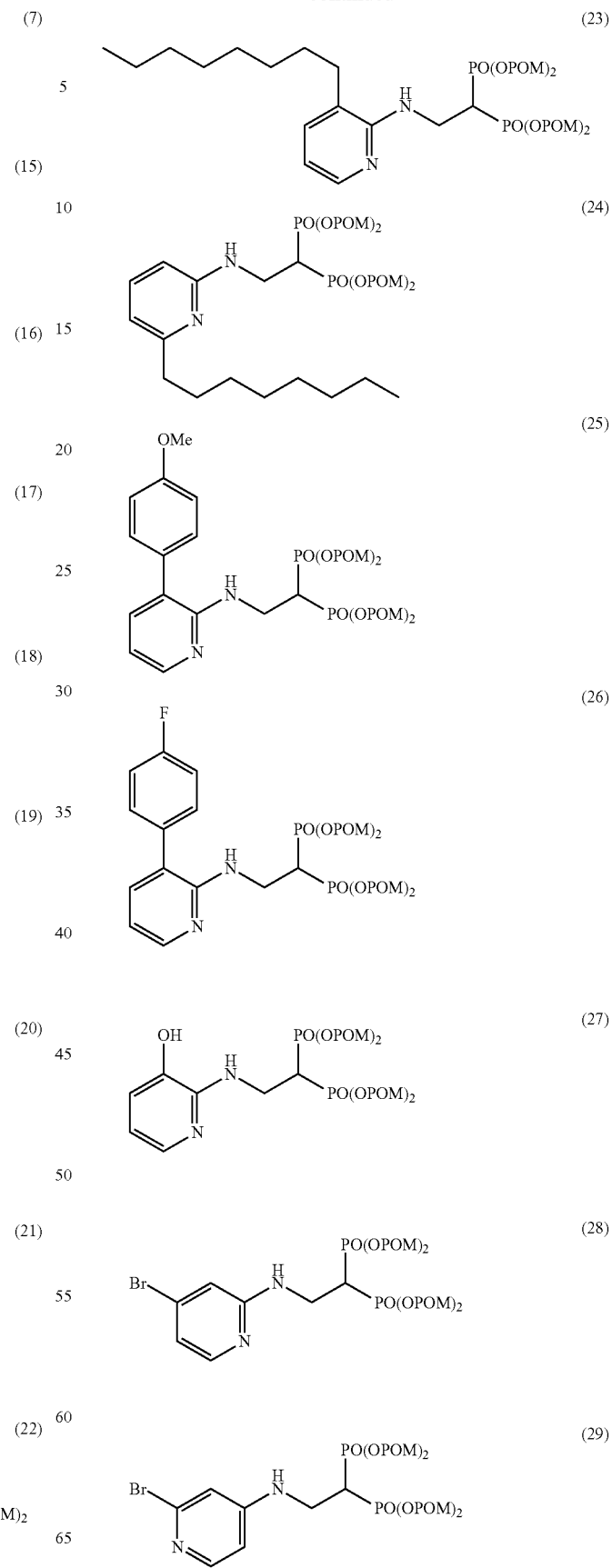

(30) 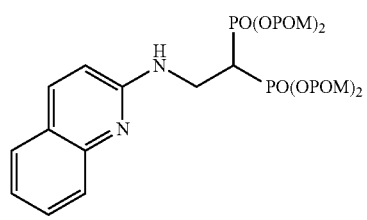
(31) 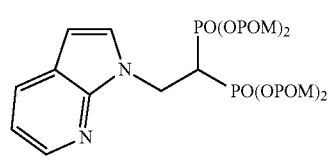
(32) 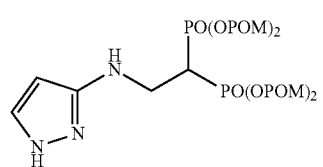
(33) 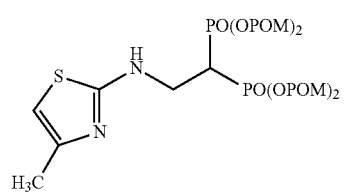
(34) 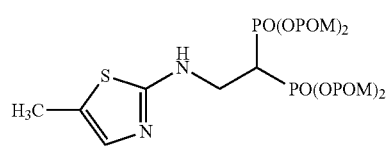
(35) 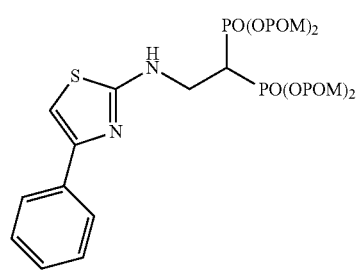
(36) 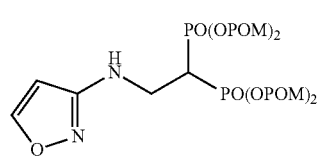
(37) 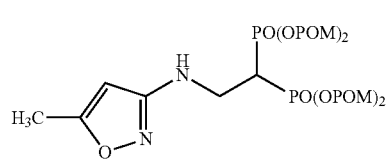
(38) 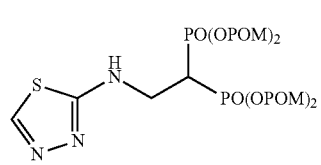
(39) 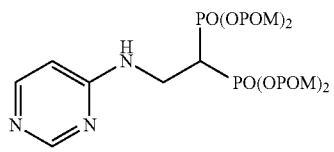
(42) 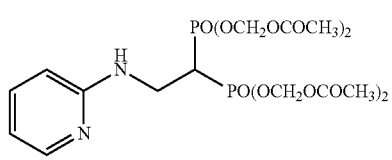
(43) 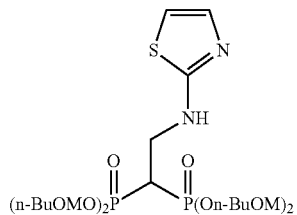
(44) 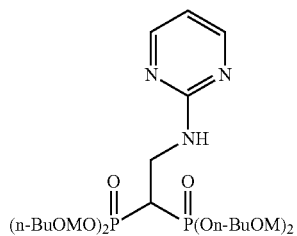
(45) 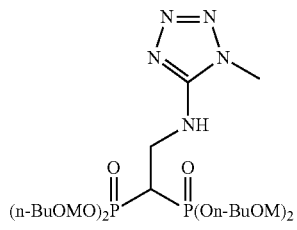
(46) 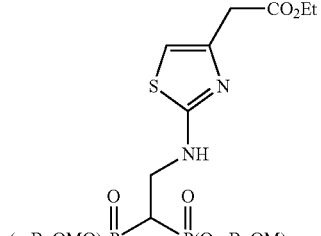
(47) 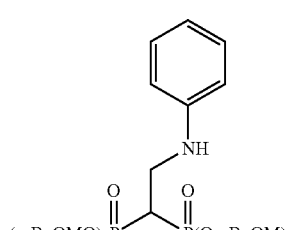

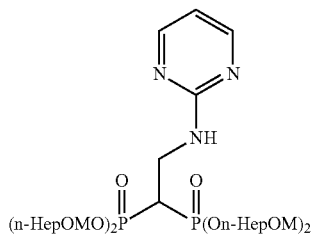

(48)

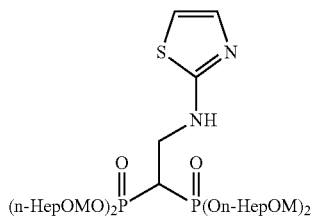

(49)

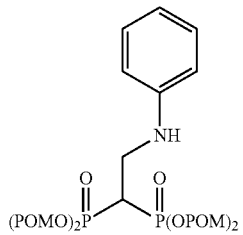

(50)

In addition, bisphosphonic acids corresponding to the above-mentioned compounds 1-7 are the following compounds 8-14, respectively.

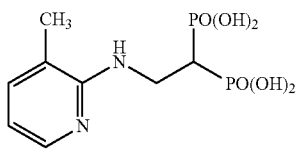

(8)

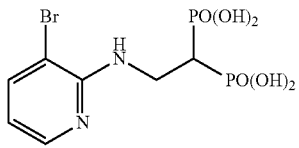

(9)

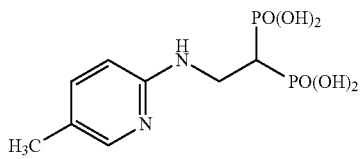

(10)

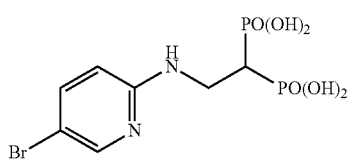

(11)

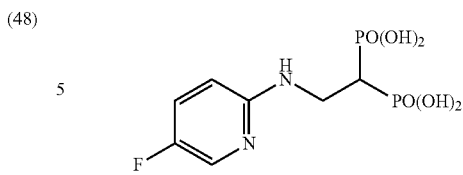

(12)

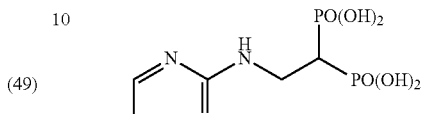

(13)

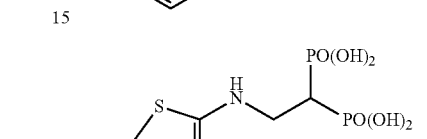

(14)

The bisphosphonic acid ester derivative in the present invention can be efficiently produced by 3 synthesis steps. It is explained below by taking conversion to pivaloyloxymethyl (POM) as an example.

First, using (a) tetramethyl methylenediphosphonate ester as a starting material, tetramethyl vinylidenediphosphonate ester is synthesized. Next, (b) tetramethyl vinylidenediphosphonate ester is converted to POM, pivaloyloxymethyl vinylidenediphosphonate ester is synthesized, and separated by purification. Lastly, (c) using the pivaloyloxymethyl vinylidenediphosphonate ester as an acceptor, Michael addition of a desired compound is performed.

When tetrakispivaloyloxymethyl 2-(thiazol-2-ylamino)ethylidene-1,1-bisphosphonate (compound 7) is synthesized as the final product, 2-aminothiazole is used as the desired compound in stage (c).

The derivative of the present invention can be specifically synthesized according to the synthesis procedure of Reference Example. For example, compound 7 can be produced according to the following scheme 1.

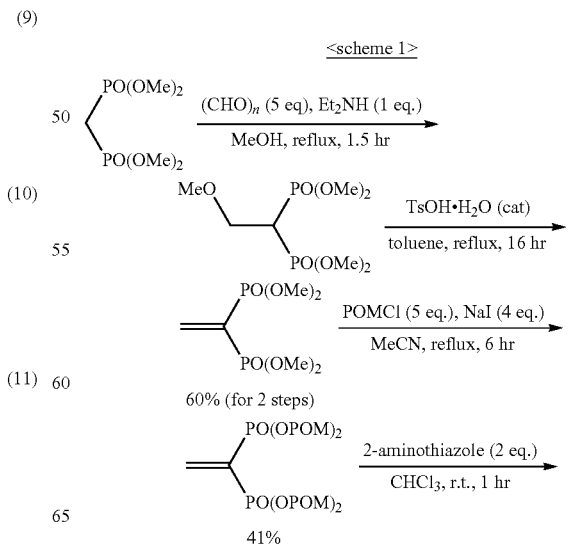

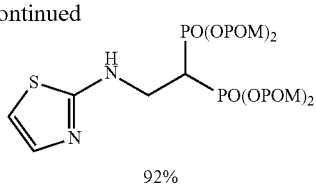

92%

By appropriately modifying or altering the starting materials and reagents, and reaction conditions and the like used in the methods shown in the Examples, based on known methods, all compounds encompassed in the scope of the present invention can be produced and, for example, a compound wherein n is 2-6 can be produced by appropriately modifying or altering based on the method described in Japanese Unexamined Patent Application Publication (Translation of PCT Application) No. 8-508245.

In the case of conversion to n-butanoyloxymethyl (BuOM), the compound can be produced by using BuOMCl instead of POMCl in the first reaction of the lower panel of scheme 1.

The derivative in the present invention may further be a pharmaceutically acceptable salt. When the derivative of the present invention or a salt thereof contains an isomer (e.g., optical isomer, geometric isomer and tautomer) and the like, the present invention encompasses such isomers and also encompasses solvate, hydrate and various shapes of crystals.

In the present invention, as a pharmaceutically acceptable salt, general salts pharmacologically and pharmaceutically acceptable salts can be mentioned. Specific examples of such salt include the following.

Examples of basic addition salt include alkali metal salts such as sodium salt, potassium salt and the like; alkaline earth metal salts such as calcium salt, magnesium salt and the like; ammonium salt; trimethylamine salt, triethylamine salt; aliphaticamine salts such as dicyclohexylamine salt, ethanolamine salt, diethanolamine salt, triethanolamine salt, procaine salt and the like; aralkylamine salts such as N,N-dibenzylethylenediamine and the like; heterocycle aromatic amine salts such as pyridine salt, picoline salt, quinoline salt, isoquinoline salt and the like; quaternary ammonium salts such as tetramethylammonium salt, tetraethylammonium salt, benzyltrimethylammonium salt, benzyltriethylammonium salt, benzyltributylammonium salt, methyltrioctylammonium salt, tetrabutylammonium salt and the like; arginine salt; basic amino acid salts such as lysine salt and the like; and the like.

Examples of acid addition salt include inorganic acid salts such as hydrochloride, sulfate, nitrate salt, phosphate, carbonate, hydrogencarbonates, perchlorate and the like; organic acid salts such as acetate, propionate, lactate, maleate, fumarate, tartrate, malate, citrate, ascorbate and the like; sulfonates such as methanesulfonate, isethionate, benzenesulfonate, p-toluenesulfonate and the like; acidic amino acid salts such as aspartate, glutamate and the like; and the like.

Since the novel bisphosphonic acid ester derivatives of the present invention are efficiently transferred into cells as compared to unesterified bisphosphonic acid, they have high farnesyl diphosphate synthase inhibitory activity. As a result, they suppress production of isoprenoid metabolites such as cholesterol, liposoluble vitamin, lipoprotein and the like, which are essential for cell survival and exhibit superior direct tumor damaging effect and virus-infected cell cytotoxicity effect. Therefore, the present invention provides direct or indirect antitumor agents and antiviral agents containing the bisphosphonic acid ester derivative as an active ingredient.

The antitumor and antiviral agents of the present invention can be used by administering to the living body, and preferably administered to mammals (human, mouse, rat, hamster, rabbit, cat, dog, bovine, sheep, monkey etc.).

The novel bisphosphonic acid ester derivatives of the present invention specifically stimulate and proliferate and/or induce γδ T cells present in the blood such as peripheral blood in the living body, or lymph fluid, as well as can induce or potentiate an antitumor action of these cells. Therefore, the present invention provides lymphocyte-treating agent containing the bisphosphonic acid ester derivative as an active ingredient.

As an antitumor action of the γδ T cells, recognition of a molecule expressing in cancer cells, for example, MICA/B and IPP (isopentenyl pyrophosphate) via a T cell receptor thereof and injury of the cell by γδ T cells can be mentioned. Furthermore, enhancement of antitumor activity by the action of cytokines such as TNF-α, INF-γ and the like produced by γδ T cells can be mentioned.

The lymphocyte-treating agents of the present invention have an action to proliferate and/or induce γδ T cells in vivo and ex vivo. Therefore, the lymphocyte-treating agent of the present invention can be used by treating a sample containing γδ T cells collected from a living body, or directly administering to a living body. Here, the living body means mammals (human, mouse, rat, hamster, rabbit, cat, dog, bovine, sheep, monkey etc.), and human is particularly preferable.

The present invention also includes a method of suppressing proliferation of tumor cells, comprising a step of proliferating and/or inducing γδ T cells by reacting the lymphocyte-treating agent of the present invention on a sample containing γδ T cells collected from a living body, and a step of returning the γδ T cells to the living body.

As a sample containing γδ T cells collected from a living body, blood such as peripheral blood and lymph fluid can be recited as examples. As a target of the lymphocyte-treating agent of the present invention, peripheral blood is preferable, and it is more preferable to use a mononuclear cell fraction separated from the peripheral blood by a specific gravity centrifugation method.

It is possible to stimulate γδ T cells in a sample with the lymphocyte-treating agent of the present invention by culturing the lymphocyte-treating agent and the sample according to a conventional method. It is possible to induce and/or proliferate γδ T cells by culturing in the presence of a bisphosphonic acid ester derivative in a trace amount of 100 pM-100 μM, preferably 100 pM-20 μM, further preferably 100 pM-5 μM.

Since the bisphosphonic acid ester derivatives as the active ingredient in the lymphocyte-treating agent of the present invention have a bisphosphonic acid skeleton, they show resistance to alkaliphosphatase as compared to conventional lymphocyte-treating agents (Biology Trace Element Research, 104, 131-140 (2005)). Therefore, as a culture medium of γδ T cells to induce and/or proliferate γδ T cells, one containing a serum can be used and, for example, human AB serum, fetal calf serum and the like can be used. Since a medium containing a serum can be used, γδ T cells can be advantageously provided in an amount sufficient for use in a cancer treatment, conveniently and in a short time.

As a constitution embodiment for use of the lymphocyte-treating agent of the present invention ex vivo for proliferating and/or inducing γδ T cells, the bisphosphonic acid ester derivative itself as the active ingredient may be used alone. In addition, it can also be produced as a solution of ethanol, DMSO and the like. Where necessary, other additive can also be added simultaneously. When the lymphocyte-treating agent is reacted with a sample, interleukin-2 (IL-2), interleukin-7 (IL-7), interleukin-15 (IL-15) and the like may also be added as an aid factor at a concentration of 0.1-150 IU/ml, preferably 1-100 IU/ml. Specific enhancement of the γδ T cells becomes remarkable by the addition of these.

Induction and/or proliferation of specific γδ T cells by the lymphocyte-treating agent can be evaluated by measuring, after culturing, the IFN-γ amount and/or TNF-α amount produced in the culture supernatant. For example, when the TNF-α production amount is higher than that at the time of start of culture, γδ T cells can be judged to have been induced. The IFN-γ amount and/or TNF-α amount can be performed using a conventionally-known method by using an anti-IFN-γ antibody, an anti-TNF-α antibody and the like.

The γδ T cells treated with the lymphocyte-treating agent of the present invention as mentioned above can be used by administration as a medicament to a patient. For example, a mononuclear cell fraction derived from a patient having a tumor is treated with the lymphocyte-treating agent of the present invention, and a mononuclear cell fraction found to show proliferation and/or induction of γδ T cells is administered to the patient as peripheral blood and the like to allow for exhibition of an antitumor activity. As an administration method, methods such as topical injection, intravenous injection, transdermal absorption and the like.

When the antitumor agent, antiviral agent and lymphocyte-treating agent of the present invention are used as pharmaceutical products, they are generally mixed with pharmaceutically acceptable carrier, excipient, diluent, filler, disintegrant, stabilizer, preservative, buffering agent, aromatic, colorant, sweetening agent, thickener, corrigent, solubilizing agents, and other additive known per se, specifically, water, vegetable oil, alcohol (e.g., ethanol, benzyl alcohol etc.), polyethylene glycol, glyceroltriacetate, gelatin, hydrocarbonate (e.g., lactose, starch etc.), magnesium stearate, talc, lanolin, petrolatum and the like, and a tablet, pill, powder, granule, suppository, injection, eye drop, liquid, capsule, troche, aerosol, elixir, suspension, emulsion, syrup and the like are formed by conventional methods, and they can be administered systemically or topically, orally or parenterally.

While the dose varies depending on the age, body weight, symptom, treatment effect, administration method and the like, it is generally 0.001 mg/kg-1000 mg/kg, preferably 0.01 mg/kg-100 mg/kg, for an adult, which is administered once to several times per day, orally or in the form of injection such as intravenous injection and the like.

The antitumor agent of the present invention encompasses direct and indirect antitumor agent and antiviral agent, and shows a treatment effect on benign and malignant tumor, and virus infected cells. In addition, the lymphocyte-treating agent of the present invention is useful for the prophylaxis and/or treatment of tumor. Examples of the tumor target include malignant tumors such as brain tumor (malignant astrocytoma, glioma having oligodendroglial tumor component etc.), esophagus cancer, gastric cancer, liver cancer, pancreatic cancer, large intestine cancer (colon cancer, rectal cancer etc.), bladder cancer, lung cancer (non-small cell lung cancer, small cell lung cancer, primary and metastatic squamous cell carcinoma etc.), renal cancer, breast cancer, ovarian cancer, prostate cancer, skin cancer, neuroblastoma, sarcoma, bone and soft tissue tumor, bone tumor, osteosarcoma, testis tumor, extragonadal tumor, orchis tumor, uterine cancer (uterus cervix cancer, endometrial cancer etc.), head and neck tumor (maxilla cancer, laryngeal cancer, pharyngeal cancer, tongue cancer, mouth cavity cancer etc.), multiple myeloma, malignant lymphoma (reticulum cell sarcoma, lymphosarcoma, Hodgkin's disease etc.), polycythemia vera, leukemia (acute myeloid leukemia, chronic myeloid leukemia, acute lymphocytic leukemia, chronic lymphocytic leukemia etc.), thyroid cancer, renal pelvis cancer, ureter tumor, bladder tumor, gallbladder cancer, cholangiocarcinoma, choriocarcinoma, malignant melanoma, pediatric tumor (Ewing sarcoma family, Wilms' tumor, rhabdomyosarcoma, blood vessel sarcoma, testicular embryonal carcinoma, neuroblastoma, retinoblastoma, hepatoblastoma, nephroblastoma etc.) and the like and the like. As viral infectious disease to be the target, viral infectious disease such as HTLV-1 infections, HIV infections, influenza disease, herpes disease and the like, and the like can be mentioned. In the present invention, application to bladder cancer, renal cancer, lung cancer, breast cancer, hematologic tumor such as leukemia and the like, and HTLV-1 infections is preferable.

The bisphosphonic acid ester derivative of the present invention may be included in alkylated cyclodextrin. That is, the present invention provides a pharmaceutical composition containing the above-mentioned bisphosphonic acid ester derivative of the present invention and alkylated cyclodextrin (hereinafter to be also referred to as "alkylated cyclodextrin-containing pharmaceutical composition containing of the present invention"). The alkylated cyclodextrin contained in the pharmaceutical composition refers to a compound which is cyclodextrin which is a cyclic oligosaccharide composed of 6-12 (1-4) bonded anhydrous glucose units, wherein a part or the whole of the free hydroxyl groups at the 2-, 3- and 6-position of glucose is(are) substituted by an alkyl group. β-Cyclodextrin having 7 glucose residues (hereinafter to be also referred to as "βCD") is known to have lower water-solubility as compared to α-cyclodextrin having 6 glucose residues and γ-cyclodextrin having 8 glucose residues. It is known that water-solubility markedly increases, the alcohol solubility increases when hydroxyl group of β-cyclodextrin is completely methylated.

The number of glucose residues of alkylated cyclodextrin used in alkylated cyclodextrin-containing pharmaceutical composition of the present invention is preferably 6-8, particularly preferably 7. In addition, the alkyl group is an alkyl group having 1-4 carbon atoms such as methyl, ethyl, propyl and the like, preferably an alkyl group having 1-2 carbon atoms, particularly preferably a methyl group.

The ratio of alkylation of a free hydroxyl group in cyclodextrin is not less than 60%, preferably not less than 80%, particularly preferably 100%. In cyclodextrin having an alkylation ratio of not less than 60% and less than 100%, an alkyl group may substitute a free hydroxyl group at the 2, 3 or 6-position of glucose, wherein the position and number of the substituent in glucose are not the same and may be random. A glucose wherein two hydroxyl groups of the free hydroxyl groups at the 2, 3, 6-positions are substituted by an alkyl group is dialkyldextrin, and a glucose wherein all three hydroxyl groups are substituted is trialkyldextrin. A cyclodextrin having an alkylation ratio of 100% means trialkylated dextrin. The alkylated cyclodextrin used in the present invention is particularly preferably trimethyl-β-dextrin. The alkylated cyclodextrin contained in the alkylated cyclodextrin-containing pharmaceutical composition of the present invention may be one kind or two or more kinds thereof may be used in a mixture.

The alkylated cyclodextrin to be used in the present invention may be obtained by synthesis by a method known per se, or a commercially available one may be purchased and used. For example, it is available from Tokyo Chemical Industry Co., Ltd.

In the alkylated cyclodextrin-containing pharmaceutical composition of the present invention, the molar ratio of alkylated cyclodextrin is 2-100, preferably 2-30, particularly preferably 5-15, relative to bisphosphonic acid ester derivative.

Furthermore, the alkylated cyclodextrin-containing pharmaceutical composition of the present invention optionally contains a water-soluble organic solvent. While a smaller content of the water-soluble organic solvent is more preferable, not more than 10% (weight) of the composition is preferable. It is more preferably 0.1-5%, furthermore preferably 0.5-3%. To provide the pharmaceutical composition of the present invention as an injection preparation, ethanol is used as a water-soluble organic solvent. However, it is not necessarily limited to ethanol, and an organic solvent blendable with water, which can dissolve cyclodextrin and can be used for an injection preparation, can be used.

In the production method of the alkylated cyclodextrin-containing pharmaceutical composition of the present invention, alkylated cyclodextrin is first dissolved in a water-soluble organic solvent (e.g., ethanol). The amount to be used is generally 4-400 ml, preferably 5-50 ml, per 100 mg of alkylated cyclodextrin. Then, a bisphosphonic acid derivative is added to an ethanol solution dissolving alkylated cyclodextrin, and dissolved by stirring. The obtained mixed solution is a transparent solution. The mixed solution may be directly preserved under an environment of, for example, −80° C.-4° C. and the like, or the obtained solution may be preserved as a powder by freeze-drying or drying under reduced pressure. When used as an injection preparation, a mixed solution or powder may be diluted or dissolved with injectable distilled water or an isotonic aqueous solution prepared with sodium chloride, saccharides and the like to be used.

Bisphosphonic acid derivatives are generally hardly water-soluble and desirably solubilized in a biotolerable form for administration to a living body. The present invention provides a method of solubilizing such hardly water-soluble medicament to be suitable for administration to a living body. The method specifically includes a step of mixing alkylated cyclodextrin with a hardly water-soluble medicament in a water-soluble organic solvent (hereinafter to be also referred to as "the solubilization method of the present invention").

The alkylated cyclodextrin to be used in the solubilization method of the present invention is the same as the alkylated cyclodextrin used for the above-mentioned alkylated cyclodextrin-containing pharmaceutical composition of the present invention.

As the "hardly water-soluble medicament", a bisphosphonic acid derivative, a bisphosphonic acid ester derivative and the like can be mentioned. As the bisphosphonic acid derivative, first generation bisphosphonate such as etidronate, clodronate and the like, second generation bisphosphonate such as pamidronate, neridronate, alendronate, olpadronate, ibandronate and the like, and third generation bisphosphonate tiludronate, incadronate, risedronate, zoledronate and the like can be mentioned. As the bisphosphonic acid ester derivative, the bisphosphonic acid ester derivative of the present invention can be mentioned. Besides these, prodrugs of carboxylic acid, phosphoric acid, phosphorous acid, bisphosphonic acid and the like are, which are protected by an alkoxymethyl group, also examples of the hardly water-soluble medicament.

In the solubilization method of the present invention, alkylated cyclodextrin is first dissolved in a water-soluble organic solvent (e.g., ethanol). The amount to be used is generally 4-400 ml, preferably 5-50 ml, per 100 mg of alkylated cyclodextrin. Then, a hardly water-soluble medicament is added to an ethanol solution dissolving alkylated cyclodextrin, and dissolved by stirring. The obtained mixed solution is a transparent solution.

In the solubilization method of the present invention, while the ratio of alkylated cyclodextrin relative to the poorly soluble medicament is appropriately determined according to the kind of the medicament to be used, when a bisphosphonic acid ester derivative is used, it is 1:2-100, preferably 1:2-30, particularly preferably 1:5-15, in a molar ratio.

The production method of the bisphosphonic acid ester derivative of the present invention is specifically explained below, and the production methods of the compounds shown in Comparative Examples are also shown below. The production method of the bisphosphonic acid ester derivative of the present invention is not limited to those specifically explained below. Furthermore, the pharmacological action of the compounds shown in these Examples and Comparative Examples is shown in each Experimental Example. Furthermore, the study results of the alkylated cyclodextrin-containing pharmaceutical composition of the present invention, and the solubilization method of the present invention are shown in each Experimental Example.

Unless specifically indicated, all reactions were performed under air atmosphere. Unless specifically indicated, various reagents used were commercially available products.

(Measurement Method and Marking)

$^1$H NMR and $^{13}$C NMR spectrum were measured by JNM-AL-400 spectrometer ($^1$H NMR at 400 MHz, $^{13}$C NMR at 100 MHz) and JNM-ECA-500 spectrometer ($^1$H NMR at 500 MHz, $^{13}$C NMR at 125 MHz) (JEOL Ltd., Akishima, Tokyo, Japan) in CDCl$_3$ solution. $^1$H NMR chemical shift refers to tetramethylsilane (TMS) (0.00 ppm) and $^{13}$C NMR chemical shift refers to CDCl$_3$ (77.0 ppm). The chemical shift is shown in one-millionth (ppm).

The multiplicity of the peak is abbreviated as follows. s, singlet; d, doublet; t, triplet; q, quartet; quin, quintet; sept, septet; m, multiplet; br, broadened IR spectrum was measured by FT/IR-4100 (JASCO Corp., Hachioji, Tokyo, Japan).

Mass spectrum and high resolution mass spectrum were measured by JMS-HX/HX 110A (JEOL Ltd.).

Thin layer chromatography (TLC) was performed on a pre-coated plate (0.25 mm, silica gel plate 60F$_{245}$, Merck Millipore, Mass.).

Column chromatography was performed on a silica gel plate (Kanto Chemical Co., Inc.).

(List of Abbreviations)

CHCl$_3$: chloroform, (CHO)n: para-formaldehyde, Et$_2$NH: diethylamine, MeCN: acetonitrile, MeOH: methanol, NaI: sodium iodide, POMCl: chloromethyl pivalate, TsOH: p-toluenesulfonic acid•monohydrate, N—BP: nitrogen-containing type bisphosphonic acid (derivative)

Synthesis of 1,1-Bisphosphonic Acid POM Ester

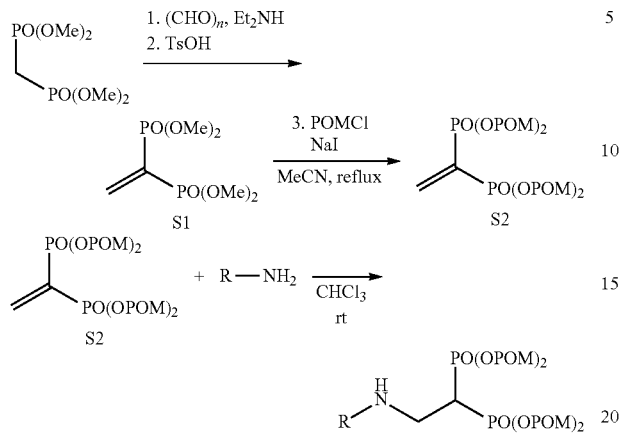

(1) Synthesis of tetramethylvinylidene-1,1-bisphosphonate (S1)

Reference document: Degenhardt, C. R.; Burdsall, D. C. J. Org. Chem. 1986, 51, 3488-3490

To a solution of para-formaldehyde (9.0 g; 300 mmol) in methanol (230 ml) was added diethylamine (6.3 ml; 60 mmol) at room temperature and the mixture was stirred at 65° C. for 30 min. Thereafter, a solution of tetramethylmethylenediphosphonate (14 g; 60 mmol) in methanol (10 ml) was added and the mixture was heated under reflux for 1.5 hr. The obtained mixture was concentrated under reduced pressure to give a crude product, which was used for the next reaction without further purification. The crude product was dissolved in toluene (200 ml), and p-toluenesulfonic acid monohydrate (114 mg; 0.6 mmol). The reaction mixture was heated under reflux for 16 hr using a Dean-Stark trap, and then diluted with chloroform. The obtained mixture was washed with brine, dried over magnesium sulfate, filtered, and concentrated under reduced pressure to give a crude product. Thereafter, the product was purified by silica gel column chromatography (methanol/chloroform=10%) to give the title object compound as a colorless oil (8.9 g; 60%).

$^1$H-NMR (400 MHz, CDCl$_3$) δ: 7.15-6.95 (2H, m), 3.85-3.75 (12H, m).

(2) Synthesis of tetrakispivaloyloxymethylvinylidene-1,1-bisphosphonate (S2)

Reference document: Degenhardt, C. R.; Burdsall, D. C. J. Org. Chem. 1986, 51, 3488-3490

To a solution of compound S1 (4.2 g; 17 mmol) in acetonitrile (85 ml) were added sodium iodide (10.2 g; 68 mmol) and POMCl (12.4 ml; 85 mmol), and the mixture was heated under reflux for 14 hr. Water was added, and the obtained mixture was extracted with ethyl acetate. The organic layer was washed with brine, dried over magnesium sulfate, filtered, and concentrated under reduced pressure to give a crude product. This was purified by silica gel column chromatography (ethyl acetate/hexane=50%) to give the title object compound as a pale-yellow oil (3.8 g; 35%).

$^1$H-NMR (400 MHz, CDCl$_3$) δ: 7.12-6.93 (2H, m), 5.75-5.65 (8H, m), 1.23 (36H, s); $^{13}$C-NMR (125 MHz, CDCl$_3$) δ: 176.5 (s), 150.1 (t), 130.8 (s, t: J$_{CP}$=175 Hz), 82.0 (t, t: J$_{CP}$=3.0 Hz), 38.6 (s), 26.7 (q); IR (neat) cm$^{-1}$: 1757, 1279, 1138, 964; FABMS m/z 667 (M$^+$+Na); FABHRMS Calcd for C$_{29}$H$_{49}$O$_{14}$N$_2$P$_2$S (M$^+$+Na): 667.2260, found: 667.2271.

Example 1: Synthesis of tetrakispivaloyloxymethyl 2-(thiazol-2-ylamino) ethylidene-1,1-bisphosphonate (7)

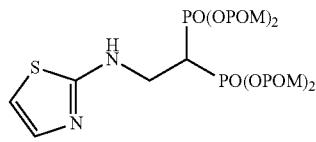

To a solution of compound S2 (64 mg; 0.1 mmol) in chloroform (0.4 ml) was added 2-aminothiazole (20 mg; 0.2 mmol), and the mixture was stirred at room temperature for 1 hr. The obtained mixture was concentrated under reduced pressure, the solvent was evaporated, and the residue was purified by silica gel column chromatography (ethyl acetate/chloroform=50%) to give the title object compound as a colorless solid (69 mg; 0 92%).

$^1$H-NMR (400 MHz, CDCl$_3$) δ: 7.09 (1H, d, J=3.7 Hz), 6.50 (1H, d, J=3.7 Hz), 5.90 (1H, br), 5.77-5.67 (8H, m), 4.00-3.88 (2H, m), 3.11 (1H, tt, J=6.0 Hz, J$_{HP}$=23.8 Hz), 1.23 (18H, s), 1.22 (18H, s); $^{13}$C-NMR (125 MHz, CDCl$_3$) δ: 176.82 (s), 176.77 (s), 168.2 (s), 138.9 (d), 107.6 (d), 82.2 (t, d: J$_{CP}$=6.0 Hz), 82.1 (t, d: J$_{CP}$=6.0 Hz), 40.6 (t, br), 38.6 (s), 38.0 (d, t: J$_{CP}$=133 Hz), 26.7 (q); IR (CHCl$_3$) cm$^{-1}$: 3735, 1749, 1279, 1136, 958; FABMS m/z 743 (M$^-$–H); FABHRMS Calcd for C$_{29}$H$_{49}$O$_{14}$N$_2$P$_2$S (M$^-$–H): 743.2379, found: 743.2383.

Example 2: Synthesis of tetrakispivaloyloxymethyl 2-(methylpyridin-2-ylamino)ethylidene-1,1-bisphosphonate (1)

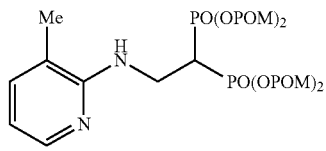

The title object compound (83%) was obtained by a method similar to that in Example 1.

$^1$H-NMR (400 MHz, CDCl$_3$) δ: 7.96 (1H, d, J=4.9 Hz), 7.21 (1H, d, J=7.1 Hz), 6.53 (1H, dd, J=4.9, 7.1 Hz), 5.77-5.68 (8H, m), 5.16 (1H, brt, J=5.8 Hz), 4.10 (2H, ddt, J=5.8, 6.1 Hz, J$_{HP}$=16.3 Hz), 3.18 (1H, tt, J=6.1 Hz, J$_{HP}$=23.4 Hz), 2.10 (3H, s), 1.22 (18H, s), 1.20 (18H, s); $^{13}$C-NMR (125 MHz, CDCl$_3$) δ: 176.8 (s), 155.7 (s), 145.2 (d), 136.8 (d), 117.6 (s), 113.4 (d), 82.2 (t, d: J$_{CP}$=6.0 Hz), 82.1 (t, d: J$_{CP}$=6.0 Hz), 38.7 (s), 38.0 (d, t: J$_{CP}$=132 Hz), 37.3 (t, br), 26.8 (q), 16.6 (q); IR (CHCl$_3$) cm$^{-1}$: 1753, 1601, 1481, 1279, 1138, 958; FABMS m/z 751 (M$^-$–H); FABHRMS Calcd for C$_{32}$H$_{53}$O$_{14}$N$_2$P$_2$ (M$^-$–H): 751.2972, found: 751.2982.

Example 3: Synthesis of tetrakispivaloyloxymethyl 2-(3-bromopyridin-2-ylamino)ethylidene-1,1-bisphosphonate (2)

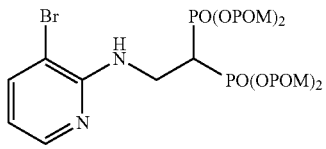

The title object compound (91%) was obtained by a method similar to that in Example 1.

$^1$H-NMR (400 MHz, CDCl$_3$) δ: 8.04 (1H, dd, J=1.7, 4.9 Hz), 7.61 (1H, dd, J=1.7, 7.6 Hz), 6.48 (1H, dd, J=4.9, 7.6 Hz), 5.87 (1H, brt, J=6.1 Hz), 5.76-5.64 (8H, m), 4.06 (2H, ddt, J=6.1, 6.3 Hz, $J_{HP}$=16.1 Hz), 3.16 (1H, tt, J=6.3 Hz, $J_{HP}$=23.3 Hz), 1.22 (18H, s), 1.21 (18H, s); $^{13}$C-NMR (125 MHz, CDCl$_3$) δ: 176.61 (s), 176.59 (s), 153.6 (s), 146.5 (d), 139.6 (d), 114.0 (d), 105.7 (s), 82.1 (t, d: $J_{CP}$=6.0 Hz), 82.0 (t, d: $J_{CP}$=6.0 Hz), 38.6 (s), 37.8 (d, t: $J_{CP}$=132 Hz), 37.3 (t, br), 26.7 (q); IR (CHCl$_3$) cm$^{-1}$: 3689, 1753, 1595, 1508, 1263, 1136, 958; FABMS m/z 815 (M$^-$–H), 817 (M$^-$+2–H); FABHRMS Calcd for C$_{31}$H$_{50}$O$_{14}$N$_2$BrP$_2$ (M$^-$–H): 815.1921, found: 815.1911.

Example 4: Synthesis of tetrakispivaloyloxymethyl 2-(5-methylpyridin-2-ylamino)ethylidene-1,1-bisphosphonate (3)

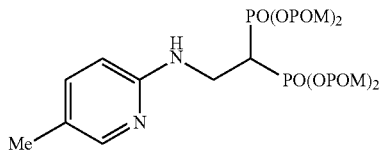

The title object compound (95%) was obtained by a method similar to that in Example 1.

$^1$H-NMR (400 MHz, CDCl$_3$) δ: 7.90-7.88 (1H, m), 7.22 (1H, dd, J=2.2, 8.3 Hz), 6.41 (1H, d, J=8.3 Hz), 5.79-5.67 (8H, m), 5.16 (1H, brt, J=6.6 Hz), 3.95 (2H, ddt, J=6.3, 6.6 Hz, $J_{HP}$=16.3 Hz), 3.07 (1H, tt, J=6.3 Hz, $J_{HP}$=23.8 Hz), 2.16 (3H, s), 1.22 (18H, s), 1.21 (18H, s); $^{13}$C-NMR (125 MHz, CDCl$_3$) δ: 176.77 (s), 176.74 (s), 155.3 (s), 147.2 (d), 138.4 (d), 122.2 (s), 108.5 (d), 82.1 (t, d: $J_{CP}$=6.0 Hz), 82.0 (t, d: $J_{CP}$=6.0 Hz), 38.6 (s), 38.0 (d, t: $J_{CP}$=133 Hz), 37.6 (t, br), 26.7 (q), 17.3 (q); IR (CHCl$_3$) cm$^{-1}$: 3689, 1751, 1604, 1506, 1279, 1138, 960; FABMS m/z 751 (M$^-$–H); FABHRMS Calcd for C$_{32}$H$_{53}$O$_{14}$N$_2$P$_2$(M$^-$–H): 751.2972, found: 751.2966.

Example 5: Synthesis of tetrakispivaloyloxymethyl 2-(5-bromopyridin-2-ylamino)ethylidene-1,1-bisphosphonate (4)

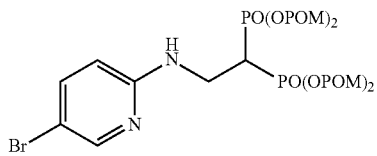

The title object compound (73%) was obtained by a method similar to that in Example 1.

$^1$H-NMR (400 MHz, CDCl$_3$) δ: 8.10 (1H, d, J=2.4 Hz), 7.44 (1H, dd, J=8.7, 2.4 Hz), 6.41 (1H, d, J=8.8 Hz), 5.76-5.67 (8H, m), 5.34 (1H, t, J=6.3 Hz), 3.94 (2H, ddt, J=6.1, 6.3 Hz, $J_{HP}$=16.5 Hz), 3.02 (1H, tt, J=6.1 Hz, $J_{HP}$=23.9 Hz), 1.22 (18H, s), 1.21 (18H, s); $^{13}$C-NMR (125 MHz, CDCl$_3$) δ: 176.7 (s), 176.6 (s), 155.8 (s), 148.2 (d), 139.3 (d), 110.5 (d), 107.7 (s), 82.0 (t, d: $J_{CP}$=6.0 Hz), 81.9 (t, d: $J_{CP}$=6.0 Hz), 38.5 (s), 37.8 (d, t: $J_{CP}$=133 Hz), 37.2 (t, br), 26.6 (q); IR (CHCl$_3$) cm$^{-1}$: 3691, 1751, 1595, 1481, 1280, 1138, 958; FABMS m/z 815 (M$^-$–H), 817 (M$^-$+2–H); FABHRMS Calcd for C$_{31}$H$_{50}$O$_{14}$N$_2$BrP$_2$ (M$^-$–H): 815.1921, found: 815.1933.

Example 6: Synthesis of tetrakispivaloyloxymethyl 2-(5-fluoropyridin-2-ylamino)ethylidene-1,1-bisphosphonate (5)

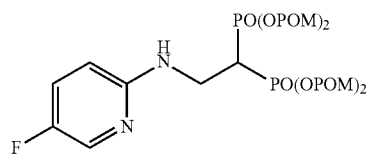

The title object compound (99%) was obtained by a method similar to that in Example 1.

$^1$H-NMR (400 MHz, CDCl$_3$) δ: 7.93 (1H, d, J=2.9 Hz), 7.18 (1H, ddd, J=2.9, 9.3 Hz, $J_{HF}$=8.0 Hz), 6.46 (1H, dd, J=9.3 Hz, $J_{HF}$=3.4 Hz), 5.76-5.67 (8H, m), 5.25 (1H, br), 3.93 (2H, ddt, J=6.1, 6.3 Hz, $J_{HP}$=16.3 Hz), 3.03 (1H, tt, J=6.1 Hz, $J_{HP}$=24.3 Hz), 1.22 (18H, s), 1.21 (18H, s); $^{13}$C-NMR (125 MHz, CDCl$_3$) δ: 176.8 (s), 176.7 (s), 153.8 (s), 153.7 (s, d: $J_{CF}$=242 Hz), 134.1 (d, d: $J_{CF}$=25 Hz), 125.1 (d, d: $J_{CF}$=22 Hz), 109.4 (d), 82.1 (t, d: $J_{CP}$=6.0 Hz), 82.0 (t, d: $J_{CP}$=6.0 Hz), 38.6 (s), 37.9 (d, t: $J_{CP}$=133 Hz), 37.7 (t, br), 26.7 (q); IR (CHCl$_3$) cm$^{-1}$: 3689, 1753, 1496, 1269, 1138, 960; FABMS m/z 755 (M$^-$–H); FABHRMS Calcd for C$_{31}$H$_{50}$O$_{14}$N$_2$FP$_2$ (M$^-$–H): 755.2722, found: 755.2709.

Example 7: Synthesis of tetrakispivaloyloxymethyl 2-(pyrimidin-2-ylamino)ethylidene-1,1-bisphosphonate (6)

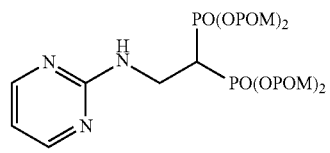

The title object compound (66%) was obtained by a method similar to that in Example 1.

$^1$H-NMR (400 MHz, CDCl$_3$) δ: 8.27 (2H, d, J=4.9 Hz), 6.56 (1H, t, J=4.9 Hz), 5.81 (1H, br), 5.76-5.69 (8H, m), 4.00 (2H, ddt, J=6.6, 6.8 Hz, $J_{HP}$=15.1 Hz), 3.16 (1H, tt, J=6.6 Hz, $J_{HP}$=23.7 Hz), 1.22 (18H, s), 1.22 (18H, s); $^{13}$C-NMR (125 MHz, CDCl$_3$) δ: 176.7 (s), 161.3 (s), 158.0 (d), 111.3 (d), 82.2 (t, d: $J_{CP}$=6.0 Hz), 82.0 (t, d: $J_{CP}$=6.0 Hz), 38.6 (s), 38.2 (d, t: $J_{CP}$=132 Hz), 37.4 (t, br), 26.7 (q); IR (CHCl$_3$)

cm⁻¹: 3735, 1749, 1277, 1136, 957; FABMS m/z 738 (M⁻–H); FABHRMS Calcd for $C_{30}H_{50}O_{14}N_3P_2$(M⁻–H): 738.2768, found: 738.2765.

Example 8: Synthesis of tetrakispivaloyloxymethyl 2-(3-benzyloxypyridin-2-ylamino)ethylidene-1,1-bisphosphonate (15)

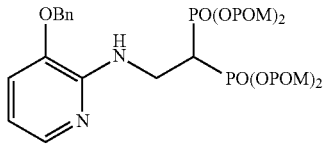

The title object compound (99%) was obtained by a method similar to that in Example 1.

¹H-NMR (400 MHz, CDCl₃) δ: 7.68 (1H, dd, J=1.2, 5.1 Hz), 7.42-7.27 (5H, m), 6.86 (1H, dd, J=1.2, 7.8 Hz), 6.49 (1H, dd, J=5.1, 7.8 Hz), 5.75-5.65 (9H, m), 5.08 (2H, s), 4.06 (2H, ddt, J=6.3, 6.6 Hz, $J_{HP}$=15.8 Hz), 3.27 (1H, tt, J=6.3 Hz, $J_{HP}$=23.3 Hz), 1.21 (18H, s), 1.19 (18H, s); ¹³C-NMR (125 MHz, CDCl₃) δ: 176.69 (s), 176.64 (s), 148.8 (s), 141.6 (s), 138.8 (d), 136.4 (s), 128.6 (d), 128.0 (d), 127.3 (d), 115.7 (d), 112.4 (d), 82.2 (t, d: $J_{CP}$=6.0 Hz), 82.0 (t, d: $J_{CP}$=6.0 Hz), 70.0 (t), 38.6 (s), 38.0 (d, t: $J_{CP}$=132 Hz), 37.0 (t, br), 26.77 (q), 26.75 (q); IR (CHCl₃) cm⁻¹: 3689, 1753, 1606, 1508, 1265, 1138, 960; FABMS m/z 843 (M⁻–H); FABHRMS Calcd for $C_{38}H_{57}O_{15}N_2P_2$ (M⁻–H): 843.3234, found: 843.3227.

Example 9: Synthesis of tetrakispivaloyloxymethyl 2-(4-methylpyridin-2-ylamino)ethylidene-1,1-bisphosphonate (16)

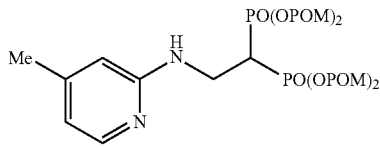

The title object compound (99%) was obtained by a method similar to that in Example 1.

¹H-NMR (400 MHz, CDCl₃) δ: 7.93 (1H, d, J=5.1 Hz), 6.43 (1H, d, J=5.1 Hz), 6.29 (1H, s), 5.77-5.67 (8H, m), 5.18 (1H, brt, J=6.3 Hz), 3.96 (2H, ddt, J=6.1, 6.3 Hz, $J_{HP}$=16.3 Hz), 3.07 (1H, tt, J=6.1 Hz, $J_{HP}$=23.6 Hz), 2.17 (3H, s), 1.22 (18H, s), 1.21 (18H, s); ¹³C-NMR (125 MHz, CDCl₃) δ: 176.71 (s), 176.69 (s), 157.3 (s), 148.3 (s), 147.1 (d), 115.1 (d), 108.9 (d), 82.1 (t, d: $J_{CP}$=6.0 Hz), 82.0 (t, d: $J_{CP}$=6.0 Hz), 38.6 (s), 38.1 (d, t: $J_{CP}$=132 Hz), 37.4 (t, br), 26.7 (q), 20.9 (q); IR (CHCl₃) cm⁻¹: 3689, 1753, 1616, 1481, 1271, 1138, 960; FABMS m/z 751 (M⁻–H); FABHRMS Calcd for $C_{32}H_{53}O_{14}N_2P_2$ (M⁻–H): 751.2972, found: 751.2963.

Example 10: Synthesis of tetrakispivaloyloxymethyl 2-(5-trifluoromethylpyridin-2-ylamino)ethylidene-1,1-bisphosphonate (17)

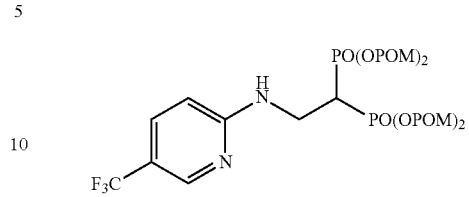

The title object compound (85%) was obtained by a method similar to that in Example 1.

¹H-NMR (400 MHz, CDCl₃) δ: 8.35-8.24 (1H, m), 7.55 (1H, dd, J=2.4, 8.5 Hz), 6.52 (1H, d, J=8.5 Hz), 5.76-5.68 (9H, m), 4.02 (2H, ddt, J=6.1, 6.3 Hz, $J_{HP}$=16.3 Hz), 3.02 (1H, tt, J=6.1 Hz, $J_{HP}$=23.7 Hz), 1.22 (18H, s), 1.21 (18H, s); ¹³C-NMR (125 MHz, CDCl₃) δ: 176.9 (s), 176.8 (s), 159.1 (s), 145.7 (d, q: $J_{CF}$=4.8 Hz), 133.9 (d, q: $J_{CF}$=3.6 Hz), 124.4 (s, q: $J_{CF}$=271 Hz), 116.0 (s, q: $J_{CF}$=32.4 Hz), 108.5 (d), 82.1 (t, d: $J_{CP}$=6.0 Hz), 82.0 (t, d: $J_{CP}$=6.0 Hz), 38.6 (s), 38.1 (d, t: $J_{CF}$=133 Hz), 37.0 (t, br), 26.7 (q); IR (CHCl₃) cm⁻: 3691, 1751, 1616, 1281, 1136, 958; FABMS m/z 805 (M⁻–H); FABHRMS Calcd for $C_{32}H_{50}O_{14}N_2F_3P_2$(M⁻–H): 805.2689, found: 805.2716.

Example 11: Synthesis of tetrakispivaloyloxymethyl 2-(5-chloropyridin-2-ylamino)ethylidene-1,1-bisphosphonate (18)

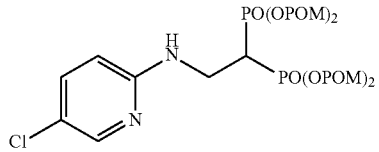

The title object compound (99%) was obtained by a method similar to that in Example 1.

¹H-NMR (400 MHz, CDCl₃) δ: 8.02 (1H, d, J=2.4 Hz), 7.33 (1H, dd, J=2.4, 8.8 Hz), 6.44 (1H, d, J=8.8 Hz), 5.76-5.67 (8H, m), 5.33 (1H, brt, J=6.3 Hz), 3.94 (2H, ddt, J=6.1, 6.3 Hz, $J_{HP}$=16.3 Hz), 3.02 (1H, tt, J=6.1 Hz, $J_{HP}$=23.9 Hz), 1.22 (18H, s), 1.21 (18H, s); ¹³C-NMR (500 MHz, CDCl₃) δ: 176.8 (s), 176.7 (s), 155.5 (s), 146.0 (d), 136.9 (d), 120.3 (s), 109.9 (d), 82.0 (t, d: $J_{CP}$=6.0 Hz), 81.9 (t, d: $J_{CP}$=6.0 Hz), 38.6 (s), 37.9 (d, t: $J_{CP}$=132 Hz), 37.3 (t, br), 26.7 (q); IR (CHCl₃) cm⁻¹: 3689, 1751, 1601, 1481, 1279, 1138, 960; FABMS m/z 771 (M³¹ –H), 773 (M⁻+2–H); FABHRMS Calcd for $C_{31}H_{50}O_{14}N_2ClP_2$ (M⁻–H): 771.2426, found: 771.2430.

Example 12: Synthesis of tetrakispivaloyloxymethyl 2-(5-phenylpyridin-2-ylamino)ethylidene-1,1-bisphosphonate (19)

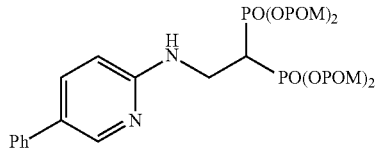

The title object compound (91%) was obtained by a method similar to that in Example 1.

$^1$H-NMR (400 MHz, CDCl$_3$) δ: 8.34 (1H, d, J=2.2 Hz), 7.64 (1H, dd, J=2.2, 8.5 Hz), 7.49 (2H, d, J=7.3 Hz), 7.41 (2H, t, J=7.3 Hz), 7.30 (1H, t, J=7.3 Hz), 6.56 (1H, d, J=8.5 Hz), 5.77-5.71 (8H, m), 5.35 (1H, br), 4.03 (2H, ddt, J=6.1, 6.5 Hz, J$_{HP}$=16.6 Hz), 3.09 (1H, tt, J=6.1 Hz, J$_{HP}$=23.7 Hz), 1.22 (18H, s), 1.21 (18H, s); $^{13}$C-NMR (125 MHz, CDCl$_3$) δ: 176.8 (s), 176.7 (s), 156.5 (s), 146.0 (d), 138.4 (s), 135.9 (d), 128.8 (d), 126.6 (d), 126.1 (d), 108.8 (d), 82.1 (t, d: J$_{CP}$=6.0 Hz), 82.0 (t, d: (T$_{CP}$=6.0 Hz), 38.6 (s), 38.1 (d, t: J$_{CP}$=132 Hz), 37.4 (t, br), 26.7 (q); IR (CHCl$_3$) cm$^{-1}$: 3689, 1751, 1277, 1138, 960; FABMS m/z 813 (M$^-$–H); FABHRMS Calcd for C$_{37}$H$_{55}$O$_{14}$N$_2$P$_2$(M$^-$–H): 813.3129, found: 817.3117.

Example 13: Synthesis of tetrakispivaloyloxymethyl 2-(6-methylpyridin-2-ylamino)ethylidene-1,1-bisphosphonate (20)

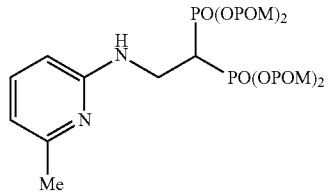

The title object compound (92%) was obtained by a method similar to that in Example 1.

$^1$H-NMR (400 MHz, CDCl$_3$) δ: 7.28 (1H, dd, J=7.3, 8.3 Hz), 6.44 (1H, d, J=7.3 Hz), 6.27 (1H, d, J=8.3 Hz), 5.78-5.67 (8H, m), 5.25 (1H, t, J=6.6 Hz), 3.97 (2H, ddt, J=6.1, 6.6 Hz, J$_{HP}$=16.1 Hz), 3.08 (1H, tt, J=6.1 Hz, J$_{HP}$=23.7 Hz), 2.34 (3H, s), 1.22 (18H, s), 1.21 (18H, s); $^{13}$C-NMR (125 MHz, CDCl$_3$) δ: 176.7 (s), 176.6 (s), 156.6 (s), 137.6 (s), 112.5 (d), 105.1 (d), 82.1 (t, d: J$_{CP}$=6.0 Hz), 82.0 (t, d: J$_{CP}$=6.0 Hz), 38.6 (s), 38.0 (d, t: J$_{CP}$=132 Hz), 37.4 (t, br), 26.7 (q), 24.0 (q); IR (CHCl$_3$) cm$^{-1}$: 3735, 1749, 1277, 1136, 958; FABMS m/z 751 (M$^-$–H); FABHRMS Calcd for C$_{32}$H$_{53}$O$_{14}$N$_2$P$_2$(M$^-$–H): 751.2972, found: 751.2963.

Example 14: Synthesis of tetrakispivaloyloxymethyl 2-(6-bromopyridin-2-ylamino)ethylidene-1,1-bisphosphonate (21)

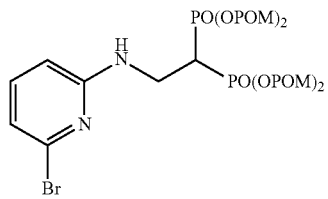

The title object compound (99%) was obtained by a method similar to that in Example 1.

$^1$H-NMR (400 MHz, CDCl$_3$) δ: 7.21 (1H, dd, J=7.6, 8.0 Hz), 6.74 (1H, d, J=7.6 Hz), 6.41 (1H, d, J=8.0 Hz), 5.79-5.69 (8H, m), 5.44 (1H, t, J=6.3 Hz), 3.94 (2H, ddt, J=6.1, 6.3 Hz, J$_{HP}$=16.3 Hz), 3.01 (1H, tt, J=6.1 Hz, J$_{HP}$=23.8 Hz), 1.23 (18H, s), 1.22 (18H, s); $^{13}$C-NMR (125 MHz, CDCl$_3$) δ: 176.82 (s), 176.76 (s), 157.3 (s), 140.1 (s), 139.1 (d), 116.4 (d), 107.1 (d), 82.2 (t, d: J$_{CP}$=6.0 Hz), 82.1 (t, d: J$_{CP}$=6.0 Hz), 38.6 (s), 37.9 (d, t: J$_{CP}$=132 Hz), 37.2 (t, br), 26.7 (q); IR (CHCl$_3$) cm$^{-1}$: 3689, 1751, 1599, 1279, 1136, 960; FABMS m/z 814 (M$^-$–2H), 816 (M$^-$+2-2H); FABHRMS Calcd for C$_{31}$H$_{50}$O$_{14}$N$_2$BrP$_2$(M$^-$–H): 815.1921, found: 815.1918.

Example 15: Synthesis of tetrakispivaloyloxymethyl 2-(5-octanylpyridin-2-ylamino)ethylidene-1,1-bisphosphonate (22)

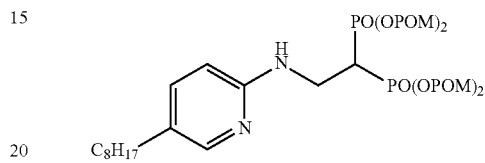

The title object compound (99%) was obtained by a method similar to that in Example 1.

$^1$H-NMR (400 MHz, CDCl$_3$) δ: 7.88 (1H, d, J=2.0 Hz), 7.25-7.21 (1H, m), 6.42 (1H, d, J=8.3 Hz), 5.77-5.67 (8H, m), 5.13 (1H, br), 3.95 (2H, ddt, J=6.1, 6.6 Hz, J$_{HP}$=16.3 Hz), 3.06 (1H, tt, J=6.1 Hz, J$_{HP}$=23.9 Hz), 2.43 (1H, t, J=7.3 Hz), 1.55-1.50 (2H, m), 1.37-1.15 (10H, m), 1.22 (18H, s), 1.21 (18H, s), 0.88 (3H, t, J=6.9 Hz); $^{13}$C-NMR (125 MHz, CDCl$_3$) δ: 176.9 (s), 176.8 (s), 136.7 (s), 127.4 (s), 125.9 (d), 124.4 (d), 108.5 (d), 82.2 (t, d: J$_{CP}$=6.0 Hz), 82.1 (t, d: J$_{CP}$=6.0 Hz), 38.7 (s), 38.2 (d, t: J$_{CP}$=132 Hz), 37.7 (t, br), 32.1 (t), 31.9 (t), 31.4 (t), 29.4 (t), 29.3 (t), 29.1 (t), 26.8 (q), 22.7 (t), 14.1 (q); IR (neat) cm$^{-1}$: 3413, 1757, 1481, 1279, 1138, 962; FABMS m/z 849 (M$^-$–H); FABHRMS Calcd for C$_{39}$H$_{67}$O$_{14}$N$_2$P$_2$(M$^-$–H): 849.4067, found: 849.4059.

Example 16: Synthesis of tetrakispivaloyloxymethyl 2-(3-octanylpyridin-2-ylamino)ethylidene-1,1-bisphosphonate (23)

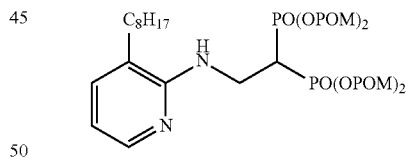

The title object compound (92%) was obtained by a method similar to that in Example 1.

$^1$H-NMR (400 MHz, CDCl$_3$) δ: 7.96 (1H, dd, J=1.7, 5.1 Hz), 7.20 (1H, dd, J=1.7, 7.1 Hz), 6.56 (1H, dd, J=5.1, 7.1 Hz), 5.77-5.67 (8H, m), 5.26 (1H, br), 4.04 (2H, ddt, J=6.1, 6.3 Hz, J$_{HP}$=16.3 Hz), 3.19 (1H, tt, J=6.1 Hz, J$_{HP}$=23.4 Hz), 2.40 (2H, t, J=7.6 Hz), 1.64-1.57 (2H, m), 1.38-1.10 (10H, m), 1.22 (18H, s), 1.20 (18H, s), 0.88 (3H, t, J=6.8 Hz); $^{13}$C-NMR (125 MHz, CDCl$_3$) δ: 176.69 (s), 176.67 (s), 155.1 (s), 144.9 (d), 135.5 (d), 121.8 (s), 113.3 (d), 82.1 (t, d: J$_{CP}$=6.0 Hz), 82.0 (t, d: J$_{CP}$=6.0 Hz), 38.6 (s), 37.8 (d, t: J$_{CP}$=132 Hz), 37.3 (t, br), 31.8 (t), 30.1 (t), 29.4 (t), 29.4 (t), 29.2 (t), 27.5 (t), 26.7 (q), 22.6 (t), 14.0 (q); IR (neat) cm$^{-1}$: 3411, 1757, 1597, 1481, 1277, 1136, 960; FABMS m/z 849 (M$^-$–H), 848 (M$^-$–2H); FABHRMS Calcd for C$_{39}$H$_{67}$O$_{14}$N$_2$P$_2$(M$^-$–H): 849.4067, found: 849.4065.

Example 17: Synthesis of tetrakispivaloyloxymethyl 2-(6-octanylpyridin-2-ylamino)ethylidene-1,1-bisphosphonate (24)

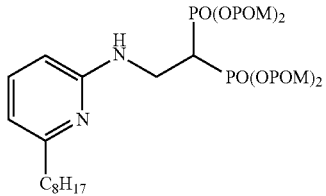

The title object compound (95%) was obtained by a method similar to that in Example 1.

$^1$H-NMR (400 MHz, CDCl$_3$) δ: 7.29 (1H, dd, J=7.1, 8.0 Hz), 6.44 (1H, d, J=7.1 Hz), 6.27 (1H, d, J=8.0 Hz), 5.77-5.67 (8H, m), 5.13 (1H, br), 3.97 (2H, ddt, J=6.1, 6.3 Hz, $J_{HP}$=16.1 Hz), 3.07 (1H, tt, J=6.1 Hz, $J_{HP}$=23.9 Hz), 2.57 (2H, t, J=7.6 Hz), 1.70-1.55 (2H, m), 1.33-1.10 (10H, m), 1.22 (18H, s), 1.21 (18H, s), 0.87 (3H, t, J=6.9 Hz); $^{13}$C-NMR (125 MHz, CDCl$_3$) δ: 176.8 (s), 176.7 (s), 160.9 (s), 156.7 (s), 137.4 (d), 112.1 (d), 105.4 (d), 82.1 (t, d: $J_{CP}$=6.0 Hz), 82.0 (t, d: $J_{CP}$=6.0 Hz), 38.6 (s), 38.1 (t), 38.0 (d, t: $J_{CP}$=132 Hz), 37.5 (t, br), 37.4 (t), 31.8 (t), 29.5 (t), 29.4 (t), 29.3 (t), 26.7 (q), 22.6 (t), 14.1 (q); IR (CHCl$_3$) cm$^{-1}$: 3735, 1751, 1458, 1279, 1136, 958; FABMS m/z 849 (M$^-$–H); FABHRMS Calcd for C$_{39}$H$_{67}$O$_{14}$N$_2$P$_2$(M$^-$–H): 849.4067, found: 849.4088.

Example 18: Synthesis of tetrakispivaloyloxymethyl 2-[3-(4-methoxyphenyl)pyridin-2-ylamino]ethylidene-1,1-bisphosphonate (25)

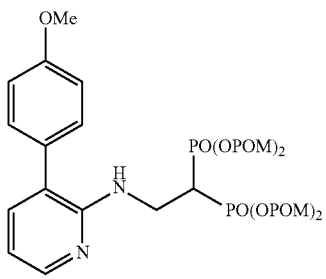

The title object compound (92%) was obtained by a method similar to that in Example 1.

$^1$H-NMR (400 MHz, CDCl$_3$) δ: 8.06 (1H, dd, J=2.0, 5.1 Hz), 7.35 (2H, d, J=8.3 Hz), 7.28-7.24 (1H, m), 6.98 (2H, d, J=8.3 Hz), 6.65 (1H, dd, J=5.1, 7.3 Hz), 5.72-5.62 (8H, m), 5.34 (1H, br), 3.99 (2H, ddt, J=6.1, 6.3 Hz, $J_{HP}$=15.6 Hz), 3.84 (3H, s), 3.32 (1H, tt, J=6.1 Hz, $J_{HP}$=23.2 Hz), 1.21-1.19 (36H, m); $^{13}$C-NMR (125 MHz, CDCl$_3$) δ: 176.64 (s), 176.56 (s), 159.1 (s), 154.3 (s), 146.4 (d), 137.1 (d), 130.0 (d), 129.5 (s), 122.5 (s), 114.4 (d), 113.4 (d), 82.1 (t, d: $J_{CP}$=6.0 Hz), 82.0 (t, d: $J_{CP}$=6.0 Hz), 38.60 (s), 38.58 (s), 37.8 (d, t: $J_{CP}$=132 Hz), 37.5 (t, br), 26.71 (q), 26.69 (q); IR (neat) cm$^{-1}$: 3447, 1755, 1483, 1279, 1138, 958; FABMS m/z 843 (M$^-$–H), 842 (M$^-$–2H); FABHRMS Calcd for C$_{38}$H$_{57}$O$_{15}$N$_2$P$_2$(M$^-$–H): 843.3235, found: 843.3231.

Example 19: Synthesis of tetrakispivaloyloxymethyl 2-[3-(4-fluorophenyl)pyridin-2-ylamino]ethylidene-1,1-bisphosphonate (26)

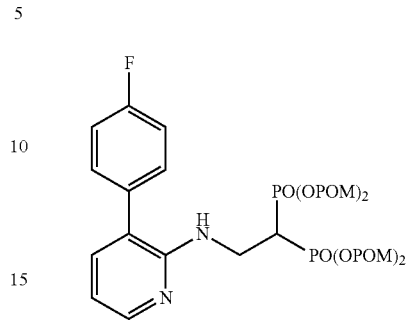

The title object compound (91%) was obtained by a method similar to that in Example 1.

$^1$H-NMR (400 MHz, CDCl$_3$) δ: 8.10 (1H, dd, J=1.7, 4.9 Hz), 7.41 (2H, dd, J=8.5 Hz, $J_{HF}$=5.3 Hz), 7.26 (1H, dd, J=1.7, 7.3 Hz), 7.18-7.11 (2H, m), 6.67 (1H, dd, J=4.9, 7.3 Hz), 5.72-5.62 (8H, m), 5.31 (1H, t, J=6.1 Hz), 3.99 (2H, ddt, J=6.1, 6.3 Hz, $J_{HP}$=16.1 Hz), 3.28 (1H, tt, J=6.3 Hz, $J_{HP}$=23.6 Hz), 1.21 (18H, s), 1.19 (18H, s); $^{13}$C-NMR (125 MHz, CDCl$_3$) δ: 176.7 (s), 176.6 (s), 162.3 (s, d: $J_{CF}$=247 Hz), 154.1 (s), 146.9 (d), 137.2 (d), 133.3 (s, d: $J_{CF}$=3.6 Hz), 130.6 (d, d: $J_{CF}$=8.4 Hz), 121.8 (s), 116.0 (d, d: $J_{CF}$=21.6 Hz), 113.4 (d), 82.1 (t, d: $J_{CP}$=6.0 Hz), 82.0 (t, d: $J_{CP}$=6.0 Hz), 38.60 (s), 38.58 (s), 37.7 (d, t: $J_{CP}$=132 Hz), 37.4 (t, br), 26.70 (q), 26.68 (q); IR (neat) cm$^{-1}$: 3444, 1755, 1504, 1277, 1138, 958; FABMS m/z 831 (M$^-$–H), 830 (M$^-$–2H); FABHRMS Calcd for C$_{37}$H$_{54}$O$_{14}$N$_2$FP$_2$(M$^-$–H): 831.3035, found: 831.3032.

Example 20: Synthesis of tetrakispivaloyloxymethyl 2-(3-hydroxypyridin-2-ylamino)ethylidene-1,1-bisphosphonate (27)

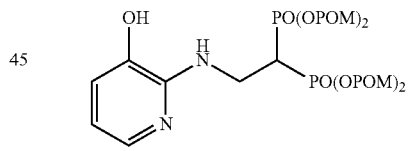

To a solution of tetrakispivaloyloxymethyl 2-(3-benzyloxypyridin-2-ylamino) ethylidene-1,1-bisphosphonate (compound 15, 253 mg, 0.30 mmol) in ethyl acetate (15 ml) was added 10% Pd/C (62 mg, 0.058 mmol) under a hydrogen atmosphere, and the mixture was stirred at room temperature for 1.5 hr. The obtained mixture was filtered and concentrated under reduced pressure to give a crude product. This was purified by silica gel column chromatography (ethyl acetate) to give the title object compound (196 mg; 87%).

$^1$H-NMR (400 MHz, CDCl$_3$) δ: 7.64 (1H, dd, J=1.5, 5.1 Hz), 6.93 (1H, dd, J=1.5, 7.6 Hz), 6.46 (1H, dd, J=5.1, 7.6 Hz), 5.78-5.65 (8H, m), 5.57 (1H, br), 4.11-4.00 (2H, m), 3.31 (1H, tt, J=6.1 Hz, $J_{HP}$=23.9 Hz), 1.22 (18H, s), 1.20 (18H, s); IR (CHCl$_3$) cm$^{-1}$: 3735, 1749, 1277, 1136, 958; FABMS m/z 752 (M$^-$–2H); FABHRMS Calcd for C$_{31}$H$_{51}$O$_{15}$N$_2$P$_2$(M$^-$–H): 753.2765, found: 753.2750.

Example 21: Synthesis of tetrakispivaloyloxymethyl 2-(4-bromopyridin-2-ylamino)ethylidene-1,1-bisphosphonate (28)

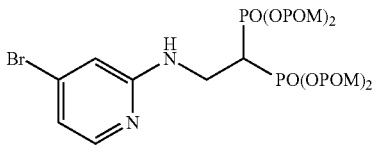

The title object compound (95%) was obtained by a method similar to that in Example 1.

$^1$H-NMR (400 MHz, CDCl$_3$) δ: 7.89 (1H, d, J=5.6 Hz), 6.73-6.70 (1H, m), 6.69-6.66 (1H, m), 5.77-5.68 (8H, m), 5.57 (1H, t, J=6.3 Hz), 3.96 (2H, ddt, J=5.8, 6.3 Hz, J$_{HP}$=16.3 Hz), 3.03 (1H, tt, J=5.8 Hz, J$_{HP}$=23.9 Hz), 1.23-1.20 (36H, m); $^{13}$C-NMR (125 MHz, CDCl$_3$) δ: 176.9 (s), 176.8 (s), 158.0 (s), 148.6 (d), 132.9 (s), 116.7 (d), 111.7 (d), 82.1 (t, d: J$_{CP}$=6.0 Hz), 82.0 (t, d: J$_u$=6.0 Hz), 38.6 (s), 38.0 (d, t: J$_{CP}$=132 Hz), 37.2 (t, br), 26.7 (q); IR (CHCl$_3$) cm$^{-1}$: 3421, 1753, 1276, 1136, 958; FABMS m/z 814 (M$^-$−2H), 816 (M$^-$+2−2H); FABHR MS Calcd for C$_{31}$H$_{50}$O$_{14}$N$_2$BrP$_2$ (M$^-$−H): 815.1921, found: 815.1915.

Example 22: Synthesis of tetrakispivaloyloxymethyl 2-(2-bromopyridin-4-ylamino)ethylidene-1,1-bisphosphonate (29)

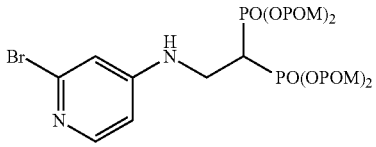

The title object compound (93%) was obtained by a method similar to that in Example 1.

$^1$H-NMR (400 MHz, CDCl$_3$) δ: 7.96 (1H, d, J=5.9 Hz), 6.71 (1H, d, J=2.0 Hz), 6.48 (1H, dd, J=2.0, 5.5 Hz), 5.75-5.66 (8H, m), 5.34 (1H, br), 3.71 (2H, ddt, J=5.8, 6.3 Hz, J$_{HP}$=16.8 Hz), 2.82 (1H, tt, J=5.8 Hz, J$_{HP}$=24.2 Hz), 1.23 (18H, s) 1.22 (18H, s); $^{13}$C-NMR (125 MHz, CDCl$_3$) δ: 177.0 (s), 176.9 (s), 153.8 (s), 149.9 (d), 142.9 (d), 110.7 (d), 107.5 (d), 82.2 (t, d: J$_{CP}$=4.8 Hz), 38.7 (s), 38.3 (t, br), 37.8 (d, t: J$_{CP}$=133 Hz), 26.7 (q); IR (neat) cm$^{-1}$: 3332, 1755, 1597, 1273, 1138, 962; FABMS m/z 814 (M$^-$−2H), 816 (M$^-$+2−2H); FABHRMS Calcd for C$_{31}$H$_{50}$O$_{14}$N$_2$BrP$_2$ (M$^-$−H): 815.1921, found: 815.1931.

Example 23: Synthesis of tetrakispivaloyloxymethyl 2-(quinolin-2-ylamino)ethylidene-1,1-bisphosphonate (30)

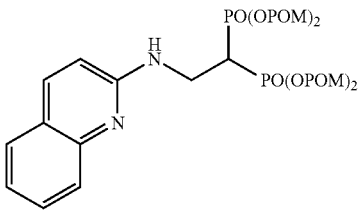

The title object compound (90%) was obtained by a method similar to that in Example 1.

$^1$H-NMR (400 MHz, CDCl$_3$) δ: 7.79 (1H, d, J=8.8 Hz), 7.69 (1H, d, J=8.5 Hz), 7.57 (1H, d, J=8.0 Hz), 7.51 (1H, ddd, J=1.2, 7.0, 8.5 Hz), 7.21 (1H, ddd, J=1.2, 7.0, 8.0 Hz), 6.69 (1H, d, J=8.8 Hz), 5.80-5.67 (8H, m), 5.59 (1H, br), 4.16 (2H, ddt, J=5.9, 6.1 Hz, J$_{HP}$=16.1 Hz), 3.27 (1H, tt, J=6.1 Hz, J$_{HP}$=23.4 Hz), 1.21 (18H, s), 1.19 (18H, s); $^{13}$C-NMR (125 MHz, CDCl$_3$) δ: 176.9 (s), 176.8 (s), 155.4 (s), 147.6 (s), 137.0 (d), 129.2 (d), 127.2 (d), 126.7 (d), 123.6 (s), 122.3 (d), 112.7 (d), 82.1 (t, d: J$_{CP}$=6.0 Hz), 82.0 (t, d: J$_{CP}$=6.0 Hz), 38.6 (s), 37.8 (d, t: J$_{CP}$=133 Hz), 37.0 (t, br), 26.7 (q); IR (CHCl$_3$) cm$^{-1}$: 3735, 1749, 1279, 1136, 960; FABMS m/z 787 (M$^-$−H), 786 (M$^-$−2H); FABHRMS Calcd for C$_{35}$H$_{53}$O$_{14}$N$_2$P$_2$(M$^-$−H): 787.2972, found: 787.3005.

Example 24: Synthesis of tetrakispivaloyloxymethyl 2-(7-azaindol-1-yl)ethylidene-1,1-bisphosphonate (31)

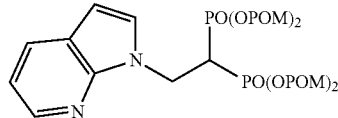

The title object compound (92%) was obtained by a method similar to that in Example 1.

$^1$H-NMR (400 MHz, CDCl$_3$) δ: 8.25 (1H, dd, J=1.5, 4.9 Hz), 7.86 (1H, dd, J=1.5, 7.8 Hz), 7.04 (1H, dd, J=4.9, 7.8 Hz), 6.39 (1H, d, J=3.7 Hz), 5.67-5.56 (9H, m), 4.85-4.76 (2H, m), 3.88 (1H, tt, J=7.3 Hz, J$_{HP}$=23.4 Hz), 1.20 (36H, s); $^{13}$C-NMR (125 MHz, CDCl$_3$) δ: 176.63 (s), 176.59 (s), 147.4 (s), 142.7 (d), 129.3 (d), 128.7 (d), 120.8 (s), 116.0 (d), 99.6 (d), 82.3 (t, d: J$_{CP}$=6.0 Hz), 82.0 (t, d: J$_{CP}$=6.0 Hz), 41.4 (t, br), 38.62 (s), 38.60 (s), 38.4 (d, t: J$_{CP}$=133 Hz), 26.7 (q); IR (CHCl$_3$) cm$^{-1}$: 1753, 1275, 1136, 958; FABMS m/z 761 (M$^-$−H), 760 (M$^-$−2H); FABHRMS Calcd for C$_{33}$H$_{51}$O$_{14}$N$_2$P$_2$(M$^-$−H): 761.2815, found: 761.2783.

Example 25: Synthesis of tetrakispivaloyloxymethyl 2-(pyrazol-3-ylamino)ethylidene-1,1-bisphosphonate (32)

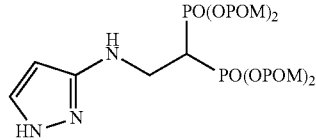

The title object compound (92%) was obtained by a method similar to that in Example 1.

$^1$H-NMR (400 MHz, CDCl$_3$) δ: 7.18 (1H, dd, J=2.2, 4.4 Hz), 5.76-5.46 (9H, m), 5.51 (1H, dd, J=2.2, 4.4 Hz), 4.44 (2H, dt, J=6.6 Hz, J$_{HP}$=13.9 Hz), 3.43 (1H, tt, J=6.6 Hz, J$_{HP}$=23.6 Hz), 1.26-1.21 (36H, m); $^{13}$C-NMR (125 MHz, CDCl$_3$) δ: 176.7 (s), 176.6 (s), 155.1 (s), 132.1 (d), 93.0 (d), 82.3 (t, d: J$_{CP}$=6.0 Hz), 82.0 (t, d: J$_{CP}$=6.0 Hz), 46.9 (t, br), 39.4 (d, t: J$_{CP}$=133 Hz), 38.6 (s), 26.7 (q); IR (neat) cm$^{-1}$: 3354, 2976, 1757, 1483, 1277, 1138, 962; FABMS m/z 726 (M$^-$−H); FABHRMS Calcd for C$_{29}$H$_{50}$O$_{14}$N$_3$P$_2$(M$^-$−H): 726.2768, found: 726.2751.

Example 26: Synthesis of tetrakispivaloyloxymethyl 2-(4-methylthiazol-2-ylamino)ethylidene-1,1-bisphosphonate (33)

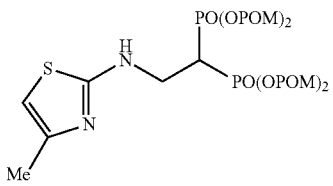

The title object compound (57%) was obtained by a method similar to that in Example 1.

$^1$H-NMR (400 MHz, CDCl$_3$) δ: 6.05 (1H, q, J=1.0 Hz), 5.77-5.69 (9H, m), 3.90 (2H, dt, J=5.8 Hz, J$_{HP}$=16.6 Hz), 3.09 (1H, tt, J=5.8 Hz, J$_{HP}$=23.7 Hz), 2.20 (3H, d, J=1.0 Hz), 1.23 (18H, s) 1.22 (18H, s); $^{13}$C-NMR (125 MHz, CDCl$_3$) δ: 176.85 (s), 176.81 (s), 167.4 (s), 148.8 (s), 101.7 (d), 82.2 (t, d: J$_{CP}$=6.0 Hz), 82.1 (t, d: J$_{CP}$=6.0 Hz), 40.7 (t, br), 38.7 (s). 38.0 (d, t: J$_{CP}$=133 Hz), 26.8 (q), 17.3 (q); IR (CHCl$_3$) cm$^{-1}$: 3735, 1749, 1279, 1136, 958; FABMS m/z 757 (M$^-$−H), 756 (M$^-$−2H); FABHRMS Calcd for C$_{30}$H$_{51}$O$_{14}$N$_2$P$_2$S (M$^-$−H): 757.2536, found: 757.2531.

Example 27: Synthesis of tetrakispivaloyloxymethyl 2-(5-methylthiazol-2-ylamino)ethylidene-1,1-bisphosphonate (34)

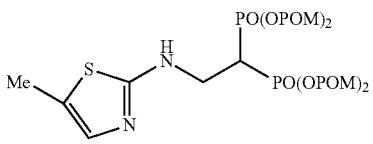

The title object compound (99%) was obtained by a method similar to that in Example 1.

$^1$H-NMR (400 MHz, CDCl$_3$) δ: 6.72 (1H, q, J=1.5 Hz), 5.76-5.65 (9H, m), 3.89 (2H, dt, J=6.1 Hz, J$_{HP}$=16.6 Hz), 3.11 (1H, tt, J=6.1 Hz, J$_{HP}$=23.9 Hz), 2.26 (3H, d, J=1.5 Hz), 1.23 (18H, s), 1.22 (18H, s); $^{13}$C-NMR (125 MHz, CDCl$_3$) δ: 176.80 (s), 176.76 (s), 166.7 (s), 135.2 (d), 122.1 (s), 82.2 (t, d: J$_{CP}$=6.0 Hz), 82.1 (t, d: J$_{CP}$=6.0 Hz), 40.5 (t, br), 38.7 (s), 38.0 (d, t: J$_{CP}$=133 Hz), 26.7 (q), 11.8 (q); IR (neat) cm$^{-1}$: 3319, 1755, 1481, 1279, 1138, 960; FABMS m/z 757 (M$^-$−H); FABHRMS Calcd for C$_{30}$H$_{51}$O$_{14}$N$_2$P$_2$S (M$^-$−H): 757.2536, found: 757.2529.

Example 28: Synthesis of tetrakispivaloyloxymethyl 2-(4-phenylthiazol-2-ylamino)ethylidene-1,1-bisphosphonate (35)

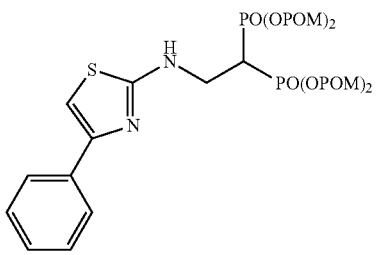

The title object compound (88%) was obtained by a method similar to that in Example 1.

$^1$H-NMR (400 MHz, CDCl$_3$) δ: 7.83-7.80 (2H, m), 7.39-7.34 (2H, m), 7.29-7.24 (1H, m), 6.72 (1H, s), 5.91 (1H, br), 5.79-5.67 (8H, m), 4.10-3.96 (2H, m), 3.21 (1H, tt, J=6.1 Hz, J$_{HP}$=23.6 Hz). 1.22 (18H, s), 1.21 (18H, s); $^{13}$C-NMR (125 MHz, CDCl$_3$) δ: 176.9 (s), 176.8 (s), 167.1 (s), 151.2 (s), 134.7 (s), 128.4 (d), 127.5 (d), 126.0 (d), 101.7 (d), 82.2 (t, d: J$_{CP}$=6.0 Hz), 82.1 (t, d: J$_c$p=6.0 Hz), 40.6 (t, br), 38.7 (s), 37.9 (d, t: J$_{CP}$=133 Hz), 26.8 (q); IR (CHCl$_3$) cm$^{-1}$: 2979, 1753, 1544, 1481, 1273, 1138, 960; FABMS m/z 819 (M$^-$−H); FABHRMS Calcd for C$_{35}$H$_{53}$O$_{14}$N$_2$P$_2$S (M$^-$−H): 819.2693, found: 819.2711.

Example 29: Synthesis of tetrakispivaloyloxymethyl 2-(isoxazol-3-ylamino)ethylidene-1,1-bisphosphonate (36)

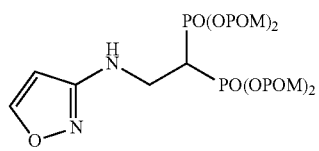

The title object compound (99%) was obtained by a method similar to that in Example 1.

$^1$H-NMR (400 MHz, CDCl$_3$) δ: 8.03 (1H, d, J=1.7 Hz), 5.90 (1H, d, J=1.7 Hz), 5.75-5.68 (8H, m), 4.97 (1H, t, J=6.5 Hz), 3.80 (2H, ddt, J=5.9, 6.5 Hz, J$_{HP}$=16.8 Hz), 3.08 (1H, tt, J=5.9 Hz, J$_{HP}$=23.9 Hz), 1.23 (18H, s), 1.22 (18H, s); $^{13}$C-NMR (125 MHz, CDCl$_3$) δ: 176.9 (s), 176.8 (s), 162.8 (s), 157.9 (d), 96.5 (d), 82.2 (t, d: J$_{CP}$=6.0 Hz), 82.1 (t, d: J$_{CP}$=6.0 Hz), 39.6 (t, br), 38.6 (s), 37.6 (d, t: J$_{CP}$=133 Hz), 26.7 (q); IR (CHCl$_3$) cm$^{-1}$: 3735, 1749, 1541, 1279, 1136, 958; FABMS m/z 727 (M$^-$−H); FABHRMS Calcd for C$_{29}$H$_{49}$O$_{15}$N$_2$P$_2$(M$^-$−H): 727.2608, found: 727.2602.

Example 30: Synthesis of tetrakispivaloyloxymethyl 2-(5-methylisoxazol-3-ylamino)ethylidene-1,1-bisphosphonate (37)

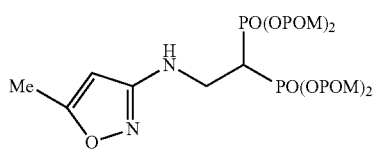

The title object compound (99%) was obtained by a method similar to that in Example 1.

$^1$H-NMR (400 MHz, CDCl$_3$) δ: 5.75-5.69 (8H, m), 5.54 (1H, s), 4.81 (1H, t, J=6.6 Hz), 3.75 (2H, ddt, J=5.9, 6.6 Hz, J$_{HP}$=17.1 Hz), 3.07 (1H, tt, J=5.9 Hz, J$_{HP}$=23.9 Hz), 2.27 (3H, s), 1.23 (18H, s), 1.22 (18H, s); $^{13}$C-NMR (125 MHz, CDCl$_3$) δ: 176.82 (s), 176.79 (s), 168.7 (s), 163.6 (s), 93.5 (d), 82.2 (t, d: J$_{CP}$=6.0 Hz), 82.1 (t, d: J$_{CP}$=6.0 Hz), 39.4 (t, br), 38.6 (s), 37.8 (d, t: J$_{CP}$=133 Hz), 26.7 (q), 12.4 (q); IR (CHCl$_3$) cm$^{-1}$: 3735, 1751, 1541, 1277, 1136, 958; FABMS

Example 31: Synthesis of tetrakispivaloyloxymethyl 2-(1,3,4-thiadiazol-2-ylamino)ethylidene-1,1-bisphosphonate (38)

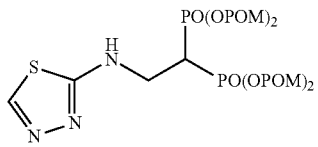

The title object compound (88%) was obtained by a method similar to that in Example 1.

$^1$H-NMR (400 MHz, CDCl$_3$) δ: 8.41 (1H, s), 6.19 (1H, br), 5.76-5.65 (8H, m), 4.10-3.97 (2H, m), 3.16 (1H, tt, J=6.1 Hz, J$_{HP}$=23.9 Hz), 1.23 (18H, s), 1.22 (18H, s); $^{13}$C-NMR (125 MHz, CDCl$_3$) δ: 177.0 (s), 176.9 (s), 167.8 (s), 142.6 (d), 82.3 (t, d: J$_{CP}$=6.0 Hz), 82.2 (t, d: J$_{CP}$=6.0 Hz), 41.1 (t, br), 38.7 (s), 37.7 (d, t: J$_{CP}$=133 Hz), 26.7 (q); IR (CHCl$_3$) cm$^{-1}$: 3735, 1749, 1541, 1279, 1136, 958; FABMS m/z 744 (M$^-$-H); FABHRMS Calcd for C$_{28}$H$_{48}$O$_{14}$N$_3$P$_2$S: 744.2332, found: 744.2353.

Example 32: Synthesis of tetrakispivaloyloxymethyl 2-(pyrimidin-4-ylamino)ethylidene-1,1-bisphosphonate (39)

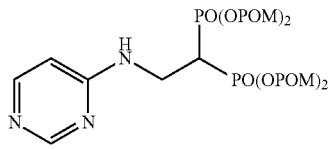

The title object compound (72%) was obtained by a method similar to that in Example 1.

$^1$H-NMR (400 MHz, CDCl$_3$) δ: 8.57 (1H, s), 8.15 (1H, d, J=6.1 Hz), 6.45 (1H, d, J=6.1 Hz), 5.80 (1H, br), 5.76-5.67 (8H, m), 4.01 (2H, ddt, J=5.9, 6.1 Hz, J$_{HP}$=16.6 Hz), 2.99 (1H, tt, J=6.1 Hz, J$_{HP}$=23.6 Hz), 1.23 (18H, s), 1.22 (18H, s); IR (neat) cm$^{-1}$: 3319, 1755, 1603, 1277, 1138, 960; FABMS m/z 738 (M$^-$-H); FABHRMS Calcd for C$_{30}$H$_{50}$O$_{14}$N$_3$P$_2$(M$^{31}$-H): 738.2768, found: 738.2805.

Example 33: Synthesis of tetrakisacetyloxymethyl 2-(pyridin-2-ylamino)ethylidene-1,1-bisphosphonate (42)

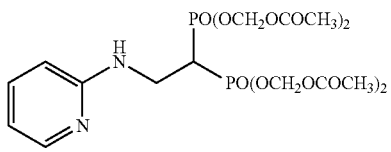

The title object compound was obtained by a method similar to that in Example 1.

$^1$H-NMR (400 MHz, CDCl$_3$) δ: 8.09 (1H, dd, J=2.0, 5.1 Hz), 7.39 (1H, ddd, J=2.0, 7.1, 8.3 Hz), 6.59 (1H, dd, J=5.1, 7.1 Hz), 6.47 (1H, d, J=8.3 Hz), 5.75-5.66 (8H, m), 5.21 (1H, t, J=6.3 Hz), 4.00 (2H, ddt, J=6.1, 6.3 Hz, J$_{HP}$=16.3 Hz), 3.14 (1H, tt, J=6.1 Hz, J$_{HP}$=23.7 Hz), 2.13 (12H, s); $^{13}$C-NMR (125 MHz, CDCl$_3$) δ: 169.4 (s), 169.3 (s), 157.1 (s), 147.5 (s), 137.4 (d), 113.5 (d), 108.9 (d), 81.8 (t, d: J$_{CP}$=6.0 Hz), 81.7 (t, d: (J$_{CP}$=6.0 Hz), 37.9 (d, t: J$_{CP}$=133 Hz), 37.2 (t, t: J$_{CP}$=3.6 Hz), 20.6 (q); IR (neat) cm$^{-1}$: 3413, 1768, 1371, 1213, 1014; FABMS m/z 569 (M$^-$-H); FAB-HRMS Calcd for C$_{19}$H$_{27}$O$_{14}$N$_2$P$_2$(M$^-$-H): 569.0937, found: 569.0939.

Synthesis of 1,1-bisphosphonic Acid n-BuOM Ester and n-HepOM Ester n-BuOM form and n-HepOM form were also synthesized under the same conditions as those for POM form.

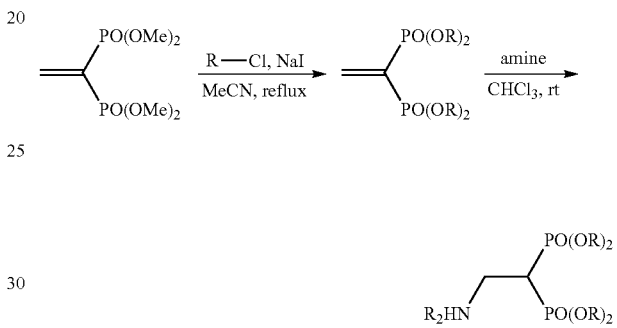

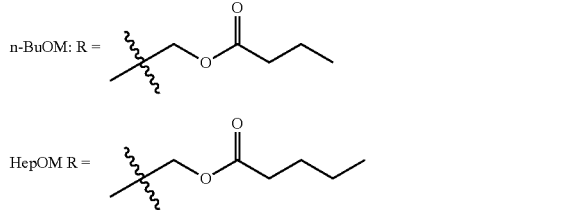

Example 34: Synthesis of tetrakis-normal-butyloxymethyl 2-(thiazol-2-ylamino)ethylidene-1,1-bisphosphonate (43)

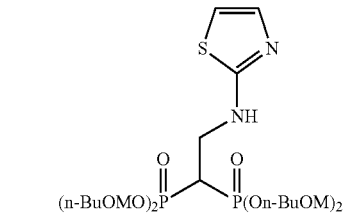

$^1$H-NMR (400 MHz, CDCl$_3$) δ: 7.10 (1H, d, J=3.5 Hz), 6.51 (1H, d, J=3.5 Hz), 5.75-5.69 (8H, m), 3.95 (2H, dt, J=6.0, J$_{HP}$=16.5 Hz), 3.13 (1H, tt, J=6.2 Hz, J$_{HP}$=23.6 Hz), 2.39-2.34 (8H, m), 1.73-1.61 (8H, m), 0.95 (12H, t, J=7.0 Hz).

Example 35: Synthesis of tetrakis-normal-butyloxymethyl 2-(pyrimidin-2-ylamino)ethylidene-1,1-bisphosphonate (44)

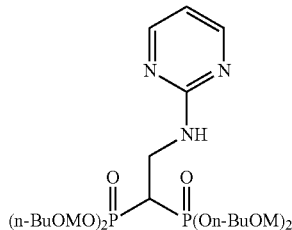

$^1$H-NMR (400 MHz, CDCl$_3$) δ: 8.28 (2H, d, J=4.5 Hz), 6.57 (1H, t, J=4.5 Hz), 5.78-5.67 (8H, m), 4.08-3.93 (2H, m), 3.19 (1H, tt, J=6.5 Hz, J$_{HP}$=24.0 Hz), 2.39-2.34 (8H, m), 1.73-1.61 (8H, m), 0.96 (12H, t, J=7.5 Hz).

Example 36: Synthesis of tetrakis-normal-butyloxymethyl 2-(1-methyl-1H-tetrazol-5-ylamino)ethylidene-1,1-bisphosphonate (45)

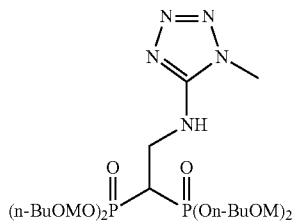

$^1$H-NMR (400 MHz, CDCl$_3$) δ: 5.78-5.63 (8H, m), 5.44 (1H, t, J=6.5 Hz), 4.04-3.89 (2H, m), 3.79 (s, 3H), 3.15 (1H, tt, J=6.0 Hz, J$_{HP}$=23.5 Hz), 2.43-2.34 (8H, m), 1.73-1.59 (8H, m), 0.99-0.93 (12H, m).

Example 37: Synthesis of tetrakis-normal-butyloxymethyl 2-(4-(2-ethoxy-2-oxoethyl)thiazol-2-ylamino)ethylidene-1,1-bisphosphonate (46)

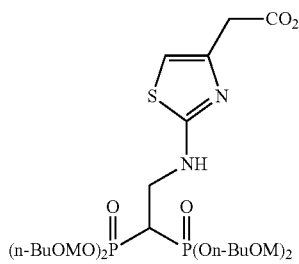

$^1$H-NMR (400 MHz, CDCl$_3$) δ: 6.36 (1H, s), 5.88 (1H, brs), 5.77-5.66 (8H, m), 4.17 (1H, q, J=7.0 Hz), 3.89 (2H, dt, J=5.5 Hz, J=17.0 Hz), 3.57 (2H, s), 3.11 (1H, tt, J=6.0 Hz, J$_{HP}$=24.0 Hz), 2.39-2.34 (8H, m), 1.73-1.61 (8H, m), 1.27 (3H, t, J=7.0 Hz), 0.96 (12H, t, J=7.5 Hz).

Example 38: Synthesis of tetrakis-normal-butyloxymethyl 2-phenylaminoethylidene-1,1-bisphosphonate (47)

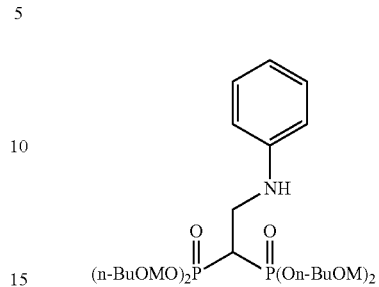

$^1$H-NMR (400 MHz, CDCl$_3$) δ: 7.21-7.15 (2H, m), 6.77-6.64 (3H, m), 5.76-5.66 (8H, m), 4.56 (1H, t, J=7.1 Hz), 3.84-3.68 (2H, m), 2.92 (1H, tt, J=5.5 Hz, J$_{HP}$=24.0 Hz), 2.37-2.31 (8H, m), 1.72-1.59 (8H, m), 1.27 (3H, t, J=7.0 Hz), 0.98-0.92 (12H, t, m).

Example 39: Synthesis of tetrakis-normal-heptyloxymethyl 2-(pyrimidin-2-ylamino)ethylidene-1,1-bisphosphonate (48)

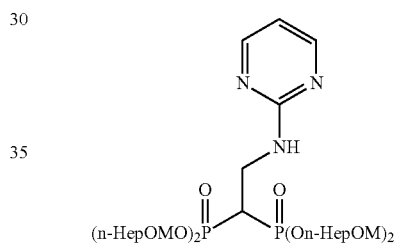

$^1$H-NMR (400 MHz, CDCl$_3$) δ: 8.28 (2H, d, J=5.0 Hz), 6.57 (1H, t, J=5.0 Hz), 5.82 (1H, t, J=6.5 Hz), 5.76-5.66 (8H, m), 4.07-3.93 (2H, m), 3.19 (1H, tt, J=6.5 Hz, J$_{HP}$=23.5 Hz), 2.40-2.35 (8H, m), 1.67-1.58 (8H, m), 1.36-1.22 (24H, m), 0.90-0.86 (12H, m).

Example 40: Synthesis of tetrakis-normal-heptyloxymethyl 2-(thiazol-2-ylamino)ethylidene-1,1-bisphosphonate (49)

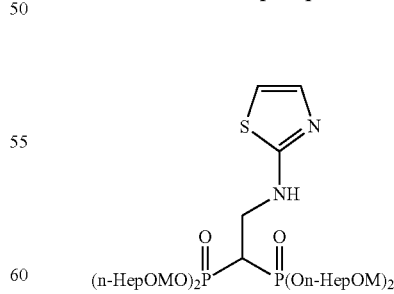

$^1$H-NMR (400 MHz, CDCl$_3$) δ: 7.10 (1H, d, J=3.5 Hz), 6.51 (1H, d, J=3.5 Hz), 5.86 (1H, brs), 5.74-5.68 (8H, m), 4.01-3.87 (2H, m), 3.12 (2H, dt, J=6.0, J$_{HP}$=23.5 Hz), 2.40-2.35 (8H, m), 1.67-1.58 (8H, m), 1.36-1.29 (24H, m), 0.90-0.86 (12H, m).

Example 41: Synthesis of tetrakispivaloyloxymethyl 2-phenylaminoethylidene-1,1-bisphosphonate (50)

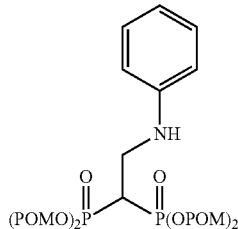

$^1$H-NMR (400 MHz, CDCl$_3$) δ: 7.21-7.15 (2H, m), 6.76-6.64 (3H, m), 5.77-5.67 (8H, m), 3.76 (2H, dt, J=5.5 Hz, J$_{HP}$=16.5 Hz), 2.90 (1H, tt, J=5.5 Hz, J$_{HP}$=24.0 Hz), 1.23 (18H, s). 1.21 (18H, s)

Synthesis of 1,1-bisphosphonic Acid

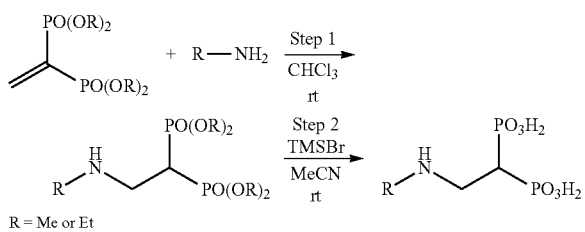

R = Me or Et

Comparative Example 1: Synthesis of 2-(methylpyridin-2-ylamino)ethylidene-1,1-bisphosphonic Acid (10)

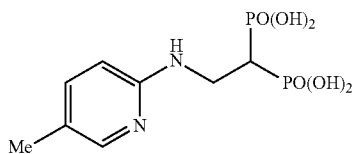

To a solution of tetraethylvinylidene-1,1-bisphosphonate (150 mg, 0.50 mmol) in chloroform (2 ml) was added 2-amino-5-methylpyridine (108 mg, 1.0 mmol) and the mixture was stirred at room temperature for 1 hr. The obtained mixture was concentrated under reduced pressure to give a crude product. This was purified by silica gel column chromatography (methanol/chloroform=10%) to give tetraethyl 2-aminoethylidene 1,1-bisphosphonate (171 mg; 99%).

The obtained tetraethyl 2-aminoethylidene 1,1-bisphosphonate (102 mg, 0.25 mmol) was dissolved in acetonitrile, and treated with TMSBr (0.20 ml, 1.5 mmol). The obtained mixture was stirred at room temperature for 4 hr. The mixture was concentrated under reduced pressure to give a crude product. This was purified by recrystallization from acetone-water to give title object compound (55 mg, 74%).

$^1$H-NMR (400 MHz, D$_2$O) δ: 7.71 (1H, dd, J=1.8, 9.3 Hz), 7.53 (1H, br), 6.91 (1H, d, J=9.3 Hz), 3.75 (2H, dt, J=5.9 Hz, J$_{HP}$=15.4 Hz), 2.41 (1H, tt, J=5.9 Hz, J$_{HP}$=22.4 Hz), 2.12 (3H, s); IR (KBr) cm$^{-1}$: 3303, 1668, 926; FABMS m/z 297 (M$^+$+H); FABHRMS Calcd for C$_8$H$_{15}$O$_6$N$_2$P$_2$(M$^+$+H): 297.0405, found: 297.0401.

Comparative Example 2: Synthesis of 2-(3-methylpyridin-2-ylamino)ethylidene-1,1-bisphosphonic Acid (8)

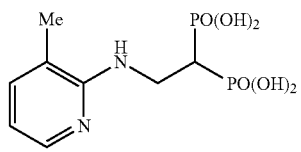

The title object compound was obtained by a method m similar to that in Comparative Example 1.

$^1$H-NMR (400 MHz, D$_2$O) δ: 7.61 (1H, d, J=6.8 Hz), 7.57 (1H, d, J=6.8 Hz), 6.73 (1H, t, J=6.8 Hz), 3.79 (2H, dt, J=5.6 Hz, J$_{HP}$=15.6 Hz), 2.47 (1H, tt, J=5.6 Hz, J$_{HP}$=22.2 Hz), 2.10 (3H, s); IR (KBr) cm$^{-1}$: 3348, 1643, 912; FABMS m/z 297 (M$^+$+H); FABHRMS Calcd for C$_8$H$_{15}$O$_6$N$_2$P$_2$(M$^+$+H): 297.0405, found: 297.0410.

Comparative Example 3: Synthesis of 2-(3-bromopyridin-2-ylamino)ethylidene-1,1-bisphosphonic Acid (9)

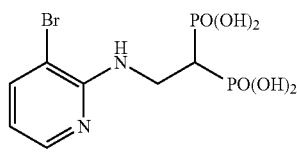

The title object compound was obtained by a method similar to that in Comparative Example 1.

$^1$H-NMR (400 MHz, D$_2$O) δ: 8.15-8.10 (1H, m), 7.75 (1H, d, J=6.3 Hz), 6.74 (1H, t, J=6.3 Hz), 3.87-3.75 (2H, m), 2.48 (1H, tt, J=5.8 Hz, J$_{HP}$=21.6 Hz); IR (KBr) cm$^{-1}$: 3340, 1639, 987; FABMS m/z 361 (M$^+$+H), 363 (M$^+$+2+H); FABHRMS Calcd for C$_7$H$_{12}$O$_6$N$_2$BrP$_2$(M$^+$+H): 360.9354, found: 360.9354.

Comparative Example 4: Synthesis of 2-(5-bromopyridin-2-ylamino)ethylidene-1,1-bisphosphonic Acid (11)

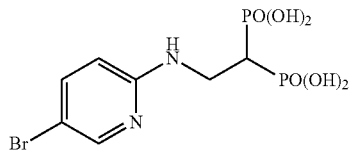

The title object compound was obtained by a method similar to that in Comparative Example 1.

97% (Step 1), 74% (Step 2); $^1$H-NMR (400 MHz, D$_2$O) δ: 7.92-7.86 (2H, m), 6.93 (1H, d, J=9.5 Hz), 3.76 (2H, dt, J=5.6 Hz, J$_{HP}$=15.1 Hz), 2.39 (1H, tt, J=5.6 Hz, J$_{HP}$=22.2

Hz); IR (KBr) cm$^{-1}$: 3292, 1662, 1161, 918; FABMS m/z 361 (M$^+$+H), 363 (M$^+$+2+H); FABHRMS Calcd for C$_7$H$_{12}$O$_6$N$_2$BrP$_2$(M$^+$+H): 360.9354, found: 360.9335.

Comparative Example 5: Synthesis of 2-(5-fluoro-pyridin-2-ylamino)ethylidene-1,1-bisphosphonic Acid (12)

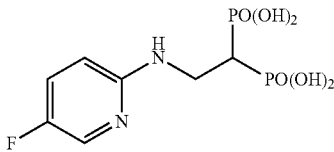

The title object compound was obtained by a method similar to that in Comparative Example 1.

95% (Step 1), 74% (Step 2); $^1$H-NMR (400 MHz, D$_2$O) δ: 7.84-7.74 (2H, m), 7.03 (1H, dd, J=4.3, 9.9 Hz), 3.77 (2H, dt, J=5.6 Hz, J$_{HP}$=15.4 Hz), 2.41 (1H, tt, J=5.6 Hz, J$_{HP}$=22.4 Hz); IR (KBr) cm$^{-1}$: 3282, 1651, 1554, 928; FABMS m/z 301 (M$^+$+H); FABHRMS Calcd for C$_7$H$_{12}$O$_6$N$_2$FP$_2$(M$^+$+H): 301.0155, found: 301.0154.

Comparative Example 6: Synthesis of 2-(pyrimidin-2-ylamino)ethylidene-1,1-bisphosphonic Acid (13)

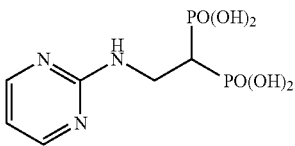

The title object compound was obtained by a method similar to that in Comparative Example 1.

87% (Step 1), 96% (Step 2); $^1$H-NMR (400 MHz, D$_2$O) δ: 8.44 (2H, br), 6.90 (1H, t, J=5.4 Hz), 3.89 (2H, dt, J=6.1 Hz, J$_{HP}$=15.1 Hz), 2.52 (1H, tt, J=6.1 Hz, J$_{HP}$=22.2 Hz); IR (KBr) cm$^{-1}$: 3334, 1657, 991; FABMS m/z 284 (M$^+$+H); FABHRMS Calcd for C$_6$H$_{12}$O$_6$N$_3$P$_2$(M$^+$+H): 284.0201, found: 284.0215.

Comparative Example 7: Synthesis of 2-(thiazol-2-ylamino)ethylidene-1,1-bisphosphonic Acid (14)

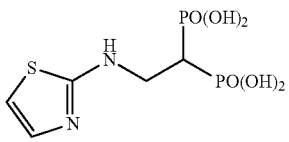

The title object compound was obtained by a method similar to that in Comparative Example 1.

93% (Step 1), 73% (Step 2); $^1$H-NMR (400 MHz, D$_2$O) δ: 7.08 (1H, d, J=4.4 Hz), 6.75 (1H, d, J=4.4 Hz), 3.75 (2H, dt, J=6.1 Hz, J$_{HP}$=15.1 Hz), 2.50 (1H, tt, J=6.1 Hz, J$_{HP}$=22.4 Hz); IR (KBr) cm$^{-1}$: 3271, 1620, 999; FABMS m/z 289 (M$^+$+H); FABHRMS Calcd for C$_5$H$_{11}$O$_6$N$_2$P$_2$S (M$^+$+H): 288.9813, found: 288.9812.

EXPERIMENTAL EXAMPLE

In the Experimental Example, the following cells were used. The number after the name of the cell indicates the source of supply.
[Source of supply]
(1) American Type Culture Collection
(2) Health Science Research Resources Bank
(3) RIKEN BioResource Center
(4) supplied by Kyoto University, Dr. Kazuhiro Iwai
(5) supplied by Tokyo Women's Medical University, Dr. Hirohito Kobayashi
(6) supplied by Kyoto University, Dr. Hidenori Tanaka
(7) supplied by Kyoto University, Dr. Junya Toguchida
(8) supplied by Tokyo Women's Medical University, Dr. Atsushi Aruga
B-cell lymphoma-derived C1R cells (C1R)(1)
Burkitt lymphoma-derived RAMOS-RA1 cells (RAMOS-RA1)(2)
Burkitt lymphoma-derived Raji cells (Raji)(2)
Burkitt lymphoma-derived Daudi cells (Daudi)(2)
T lymphoma-derived J.RT3-T3.5 cells (J.RT3-T3.5)(1)
T lymphoma-derived MOLT-3 cells (MOLT-3)(2)
T lymphoma-derived MOLT-4 cells (MOLT-4)(2)
T lymphoma-derived PEER cells (PEER)(2)
monocyte tumor-derived HL60 cells (HL60)(2)
monocyte tumor derived from NOMO-1 cells (NOMO-1)(2)
monocyte tumor-derived SCC-3 cells (SCC-3)(2)
monocyte tumor-derived THP-1 cells (THP-1)(2)
monocyte tumor-derived U937 cells (U937)(2)
monocyte tumor-derived P31/FUJ cells (P31/FUJ)(2)
erythroblast tumor-derived K562 cells (K562)(2)
breast cancer-derived HMC-1-8 cells (HMC-1-8)(2)
breast cancer-derived MCF-7 cells (MCF-7)(2)
breast cancer-derived MDA-MB-231 cells (MDA-MB-231)(1)
breast cancer-derived MRK-nu-1 cells (MRK-nu-1)(2)
breast cancer-derived SK-BR-3 cells (SK-BR-3)(1)
breast cancer-derived T-47D cells (T-47D)(1)
breast cancer-derived YMB-1-E cells (YMB-1-E)(2)
renal cancer-derived 786-0 cells (786-0)(1)
renal cancer-derived 786-0W cells (786-0W)(4)
renal cancer-derived A-704 cells (A-704)(1)
renal cancer-derived ACHN cells (ACHN)(1)
renal cancer-derived Caki-1 cells (Caki-1)(2)
renal cancer-derived UOK111 cells (UOK111)(5)
renal cancer-derived U0K121 cells (UOK121)(5)
renal cancer-derived VMRC-RCW cells (VMRC-RCW)(2)
renal cancer-derived VMRC-RCZ cells (VMRC-RCZ)(2)
bladder cancer-derived EJ-1 cells (EJ-1)(2)
bladder cancer-derived T24 cells (T24)(2)
gallbladder cancer-derived TGBC1TKB cells (TGBC1TKB)(3)
gallbladder cancer-derived TGBC2TKB cells (TGBC2TKB)(3)
gallbladder cancer-derived TGBC24TKB cells (TGBC24TKB)(3)
biliary tract cancer-derived HuCCT1 cells (HuCCT1)(2)
biliary tract cancer-derived MZChA2 cells (MZChA2)(6)
biliary tract cancer-derived TFK-1 cells (TFK-1)(6)
gastric cancer-derived ACS cells (ACS)(6)
gastric cancer-derived AGS cells (AGS)(6)
gastric cancer-derived GCIY cells (GCIY)(3)
gastric cancer-derived KATOIII cells (KATOIII)(2)
gastric cancer-derived MKN1 cells (MKN1)(2)
gastric cancer-derived MKN28 cells (MKN28)(2)
gastric cancer-derived MKN74 cells (MKN74)(2)

pancreatic cancer-derived AsPC-1 cells (AsPC-1)(1)
pancreatic cancer-derived BxPC-3 cells (BxPC-3)(1)
pancreatic cancer-derived KP4-1 cells (KP4-1)(3)
pancreatic cancer-derived KP4-2 cells (KP4-2)(3)
pancreatic cancer-derived KP4-3 cells (KP4-3)(3)
pancreatic cancer-derived MIAPaCa-2 cells (MIAPaCa-2) (2)
pancreatic cancer-derived PANC-1 cells (PANC-1)(3)
pancreatic cancer-derived PK-1 cells (PK-1)(3)
pancreatic cancer-derived PK-8 cells (PK-8)(3)
pancreatic cancer-derived PK-9 cells (PK-9)(6)
pancreatic cancer-derived T3M4 cells (T3M4)(6)
osteosarcoma-derived HOS cells (HOS)(2)
osteosarcoma-derived HuO cells (HuO)(7)
osteosarcoma-derived MG-63 cells (MG-63)(2)
osteosarcoma-derived OST cells (OST)(7)
osteosarcoma-derived SaOS-2 cells (SaOS-2)(3)
osteosarcoma-derived TAKAO cells (TAKAO) (7)
large intestine cancer-derived Colo320 cells (Colo320)(2)
large intestine cancer-derived CW2 cells (CW2)(3)
large intestine cancer-derived DLD-1 cells (DLD-1)(2)
malignant melanoma-derived C32TG cells (C32TG)(2)
malignant melanoma-derived G-361 cells (G-361)(2)
lung cancer-derived LK-2 cells (LK-2)(2)
lung cancer-derived SBC-2 cells (SBC-2)(2)
liver cancer-derived hu2 cells (hu2)(8)
osteoclast-like giant cells の GCT-IZ cells (GCT-IZ) (7)
prostate cancer-derived PC-3 cells (PC-3)(2)
fibroblastoma-derived HT-1080 cells (HT-1080)(2)

Experimental Example 1 (FIG. 1)

The direct antitumor action of bisphosphonic acid POM ester and bisphosphonic acid was studied by comparison using U937. First, U937 was cultured in RPMI1640 medium supplemented with 10% calf serum at 37° C. under 5% $CO_2$ atmosphere while maintaining log phase. The cells were recovered, and centrifuged at 1,700 rpm, 4° C. for 5 min. The supernatant was removed, and suspended in RPMI1640 medium supplemented with 10% calf serum to 500 cells/50 µl. On the other hand, 10 mM stock solution of bisphosphonic acid ester derivative was serially diluted 2-fold from 200 µM. In addition, 10 mM stock solution of bisphosphonic acid was serially diluted 2-fold from 2 mM. Then, the U937 suspension (50 µl, 500 cells) and the compound solution (50 µl) were added to a flat-bottomed 96 well plate and cultured at 37° C. under 5% $CO_2$ atmosphere for 4 days. Then, 100 µl of CellTiterGlo solution was added, and the mixture was pipetted 10 strokes, and transferred to a 96 well OptiPlate. After standing at room temperature for 10 min, the luminescence was measured by a luminometer.

As a typical example, as a combination of bisphosphonic acid POM ester and bisphosphonic acid having the same side chain, FIG. 1A (compounds 3 and 10), FIG. 1B (compounds 4 and 11), FIG. 1C (compounds 6 and 13), and FIG. 1D (compounds 7 and 14) were used.

In each FIG., -●- shows the results of a bisphosphonic acid POM ester derivative, and -○- shows the results of bisphosphonic acid.

As is clear from FIG. 1, bisphosphonic acid POM ester showed a higher activity than bisphosphonic acid in compounds having any side chain.

Experimental Example 2 (Table 1)

The direct antitumor action of bisphosphonic acid POM ester and bisphosphonic acid was studied by comparison using U937. In that case, for quantitative examination, the concentration of a compound that inhibits cell proliferation to half was calculated as $IC_{50}$, and a direct antitumor effect was studied from the value thereof by comparison. First, U937 was cultured in RPMI1640 medium supplemented with 10% calf serum at 37° C. under 5% $CO_2$ atmosphere while maintaining log phase. The cells were recovered, and centrifuged at 1,700 rpm, 4° C. for 5 min. The supernatant was removed, and suspended in RPMI1640 medium supplemented with 10% calf serum to 500 cells/50 µl. On the other hand, 10 mM stock solution of bisphosphonic acid ester derivative was serially diluted 2-fold from 200 µM. In addition, 10 mM stock solution of bisphosphonic acid was serially diluted 2-fold from 2 mM. Then, the U937 suspension (50 µl, 500 cells) and the compound solution (50 µl) were added to a flat-bottomed 96 well plate and cultured at 37° C. under 5% $CO_2$ atmosphere for 4 days. Then, 100 µl of CellTiterGlo solution was added, and the mixture was pipetted 10 strokes, and transferred to a 96 well OptiPlate. After standing at room temperature for 10 min, the luminescence was measured by a luminometer and $IC_{50}$ was calculated.

As a typical example, as a combination of bisphosphonic acid POM ester and bisphosphonic acid having the same side chain, compounds 1 and 8, compounds 2 and 9, compounds 3 and 10, compounds 4 and 11, compounds 5 and 12, compounds 6 and 13, and compounds 7 and 14 are summarized in Table 1.

TABLE 1

Comparison of POM esters and acid forms of N-BP in U937 cell growth inhibition

| POM:H | $IC_{50}$ (µM) | Ratio |
|---|---|---|
| 1:8 | 5.3:980 | 1:185 |
| 2:9 | 0.68:1,100 | 1:1,618 |
| 3:10 | 5.6:29 | 1:5 |
| 4:11 | 3.6:200 | 1:56 |
| 5:12 | 5.3:68 | 1:13 |
| 6:13 | 2.4:150 | 1:63 |
| 7:14 | 0.28:26 | 1:100 |

As shown in Table 1, bisphosphonic acid POM esters exhibited a higher activity than bisphosphonic acid in compounds having any side chain. That is, the activity increased 5-fold to 1618-fold and the activity increased several dozen times on average by forming a prodrug of bisphosphonic acid to be POM ester.

Figure 2:
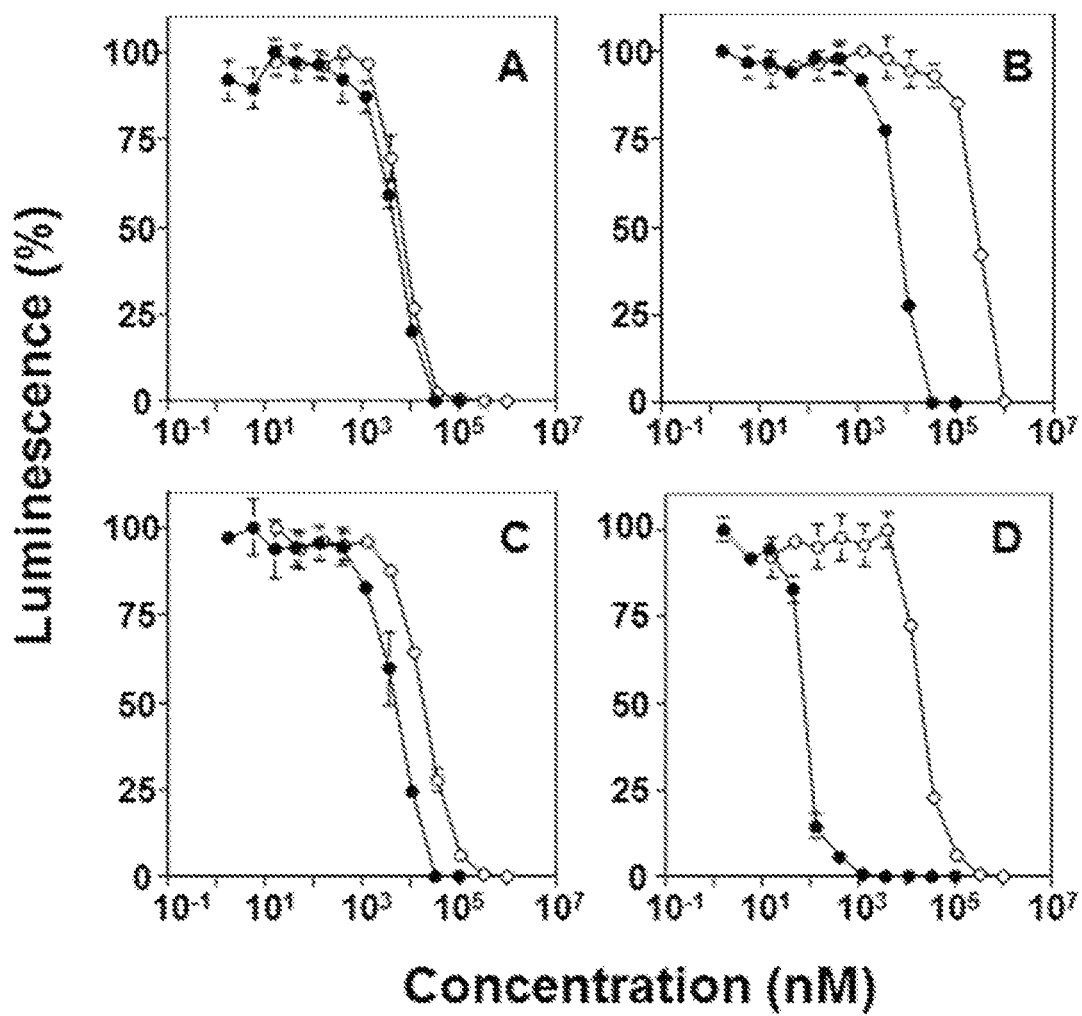
FIG. 2 is a graph showing the results of comparison study of the direct antitumor action of bisphosphonic acid POM ester derivatives (compounds 3, 4, 5, 6) and bisphosphonic acids corresponding thereto (compounds 10, 11, 12, 13) by using bladder cancer-derived EJ-1 cells.

Experimental Example 3 (FIG. 2)

The direct antitumor action of bisphosphonic acid POM ester derivatives and bisphosphonic acids was studied by comparison using EJ-1. It was performed in the same manner as in Experimental Example 1 except that EJ-1 was used as the cell to be used. For recovery of the cells, a conventional EDTA trypsin treatment was performed.

As a typical example, as a combination of bisphosphonic acid POM ester and bisphosphonic acid having the same side chain, FIG. 2A (compounds 3 and 10), FIG. 2B (compounds 4 and 11), FIG. 2C (compounds 5 and 12), and FIG. 2D (compounds 6 and 13) were used.

In each FIG., -●- shows the results of a bisphosphonic acid POM ester derivative, and -○- shows the results of bisphosphonic acid.

As is clear from FIG. 2, bisphosphonic acid POM ester showed a higher activity than bisphosphonic acid in compounds having any side chain.

Experimental Example 4 (Table 2)

The direct antitumor action of bisphosphonic acid POM esters and bisphosphonic acids was studied by comparison using EJ-1. It was performed in the same manner as in Experimental Example 2 except that EJ-1 was used as the cell to be used. For recovery of the cells, a conventional EDTA trypsin treatment was performed.

As a typical example, as a combination of bisphosphonic acid POM ester and bisphosphonic acid having the same side chain, compounds 1 and 8, compounds 2 and 9, compounds 3 and 10, compounds 4 and 11, compounds 5 and 12, compounds 6 and 13, and compounds 7 and 14 are summarized in Table 2.

TABLE 2

Comparison of EJ-1 growth inhibitory effects between by POM esters and acid forms of nitrogen-containing bisphosphonates

| POM:H | $IC_{50}$ (μM) | Ratio |
|---|---|---|
| 1:8 | 11:13 | 1:1.2 |
| 2:9 | 2.3:970 | 1:422 |
| 3:10 | 5.4:7.9 | 1:1.5 |
| 4:11 | 7.8:290 | 1:37 |
| 5:12 | 4.8:260 | 1:54 |
| 6:13 | 0.09:23 | 1:256 |
| 7:14 | 0.026:3.7 | 1:142 |

As shown in Table 2, bisphosphonic acid POM esters exhibited a higher activity than bisphosphonic acids in compounds having any side chain. That is, the activity increased 1.2-fold to 422-fold and the activity increased several dozen times on average by forming a prodrug of bisphosphonic acid to be POM ester.

Experimental Example 5 (Table 3)

The direct antitumor action of various bisphosphonic acid POM esters was studied by comparison using U937 and EJ-1. The measurement was performed according to Experimental Example 2 and Experimental Example 4.

As the bisphosphonic acid POM ester derivatives, compounds 1-7 and 15-39 were used, and compound 42 was used as other bisphosphonic acid ester derivative. The results are summarized in Table 3.

TABLE 3

| U937 growth inhibition by POM esters of nitrogen-containing bisphosphonates | | EJ-1 growth inhibition by POM esters of nitrogen-containing bisphosphonates | |
|---|---|---|---|
| Compound | $IC_{50}$ (μM) | Compound | $IC_{50}$ (μM) |
| 7 | 0.26 | 7 | 0.026 |
| 39 | 0.65 | 39 | 0.059 |
| 2 | 0.68 | 6 | 0.09 |
| 35 | 1.1 | 34 | 1.1 |
| 31 | 2.2 | 31 | 1.7 |
| 6 | 2.4 | 2 | 2.3 |
| 34 | 2.5 | 35 | 3.5 |
| 17 | 2.6 | 22 | 3.7 |
| 24 | 3.0 | 33 | 4.2 |
| 18 | 3.3 | 17 | 4.3 |

TABLE 3-continued

| U937 growth inhibition by POM esters of nitrogen-containing bisphosphonates | | EJ-1 growth inhibition by POM esters of nitrogen-containing bisphosphonates | |
|---|---|---|---|
| Compound | $IC_{50}$ (μM) | Compound | $IC_{50}$ (μM) |
| 22 | 3.4 | 23 | 4.5 |
| 23 | 3.5 | 18 | 4.8 |
| 4 | 3.6 | 3 | 5.4 |
| 33 | 5.0 | 5 | 5.7 |
| 1 | 5.3 | 28 | 6.0 |
| 5 | 5.3 | 24 | 6.3 |
| 3 | 5.6 | 4 | 7.8 |
| 21 | 6.1 | 38 | 8.5 |
| 25 | 6.2 | 26 | 8.7 |
| 32 | 6.3 | 25 | 8.8 |
| 29 | 6.6 | 21 | 9.0 |
| 30 | 6.6 | 19 | 9.5 |
| 19 | 6.7 | 30 | 10 |
| 16 | 6.8 | 1 | 11 |
| 20 | 6.9 | 29 | 12 |
| 26 | 7.0 | 32 | 12 |
| 15 | 7.1 | 27 | 13 |
| 28 | 7.1 | 16 | 15 |
| 36 | 7.9 | 36 | 15 |
| 37 | 7.9 | 15 | 16 |
| 27 | 8.9 | 20 | 16 |
| 38 | 11 | 37 | 16 |
| 42 | 17 | 42 | 16 |

As shown in Table 3, in both U937 and EJ-1, compounds 2, 6, 7, 31, 34, 35, 39 exhibited a high activity, and compounds 7 and 39 showed a particularly high activity.

Figure 3:
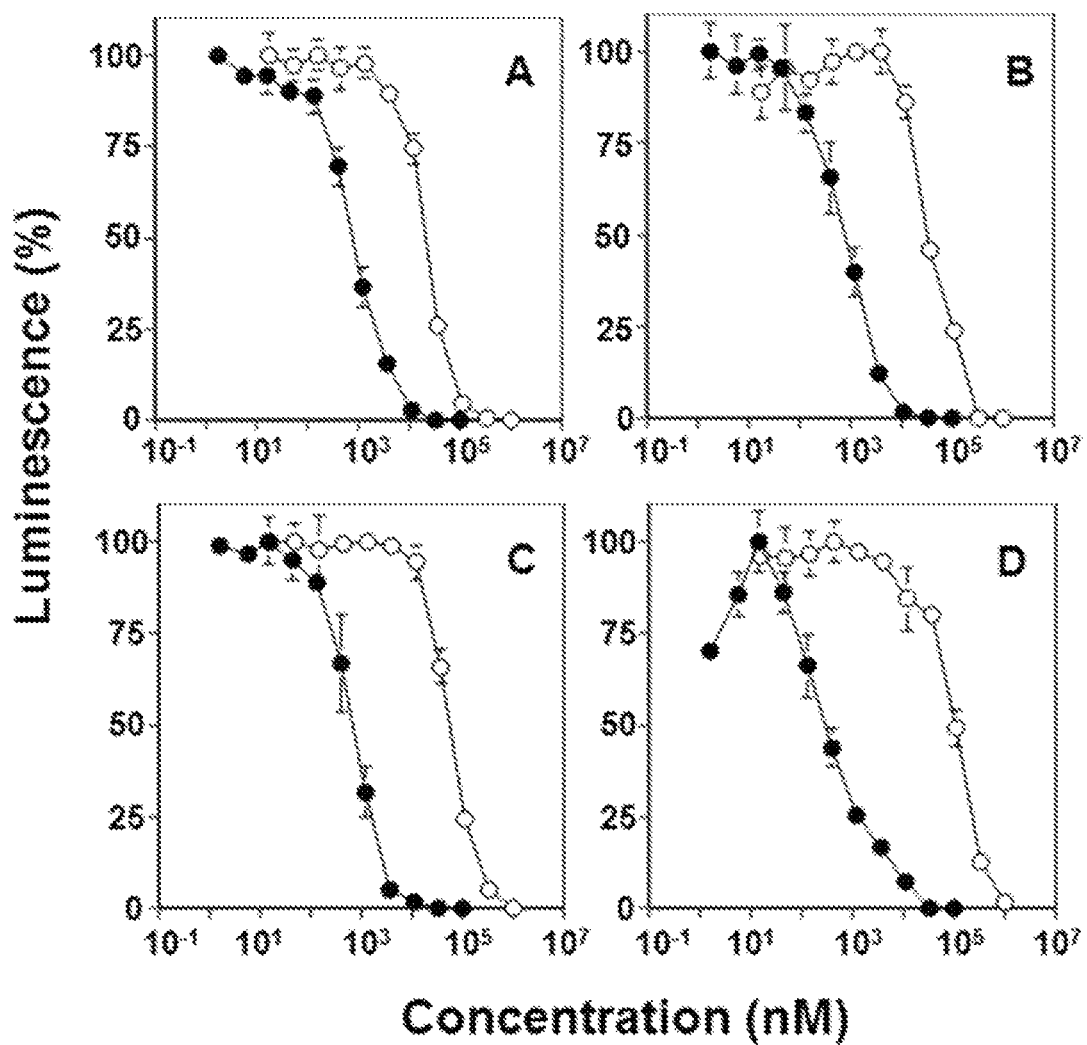
FIG. 3 is a graph showing the results of study using various carcinoma cells, which verify that compound 7, which is a bisphosphonic acid POM ester derivative, has a high, direct antitumor action. As a comparison target, compound 14, which is bisphosphonic acid having the same side chain, was used.

Experimental Example 6 (FIG. 3)

From the results of the above-mentioned Experimental Examples, a high direct antitumor action of compound 7, which is a bisphosphonic acid POM ester derivative, was confirmed in U937 and EJ-1, the level of the direct antitumor activity was examined in various carcinoma cells. In this case, to study activity promoting action of POM esterification, the antitumor action of compound 14, which is bisphosphonic acid having the same side chain, was simultaneously studied by comparison in various tumor cells. First, 786-0, LK-2, OST, PK-1 were cultured in RPMI1640 medium supplemented with 10% calf serum at 37° C. under 5% $CO_2$ atmosphere while maintaining log phase. The cells were recovered by a conventional EDTA trypsin treatment, and centrifuged at 1,700 rpm, 4° C. for 5 min. The supernatant was removed, and suspended in RPMI1640 medium supplemented with 10% calf serum to 500 cells/50 μl. On the other hand, 10 mM stock solution of compound 7 which is a bisphosphonic acid POM ester derivative was serially diluted 2-fold from 200 μM. In addition, 10 mM stock solution of compound 14 which is bisphosphonic acid was serially diluted 2-fold from 2 mM. Then, the cell suspension (50 μl, 500 cells) and the compound solution (50 μl) were added to a flat-bottomed 96 well plate and cultured at 37° C. under 5% $CO_2$ atmosphere for 4 days. Then, 100 μl of CellTiterGlo solution was added, and the mixture was pipetted 10 strokes, and transferred to a 96 well OptiPlate. After standing at room temperature for 10 min, the luminescence was measured by a luminometer.

FIG. 3A shows the results of renal cancer-derived 786-0, FIG. 3B shows the results of lung cancer-derived LK-2, FIG. 3C shows the results of osteosarcoma-derived OST, FIG. 3D shows the results of pancreatic cancer-derived PK-1. The results of compound 7 are shown by -●-, and the results of compound 14 are shown by -○-. As is clear from FIG. 3, bisphosphonic acid POM ester derivative showed a higher activity than bisphosphonic acid. Therefrom it was clarified that POM esterification remarkably increases the antitumor activity of bisphosphonic acid.

Experimental Example 7 (Table 4)

To quantitatively study an action of compound 7, which is a bisphosphonic acid POM ester derivative, on various tumor cell lines, the concentration of a compound that inhibits cell proliferation to half was calculated as $IC_{50}$, and a direct antitumor effect was studied from the value thereof. In this case, to study effect of POM esterification, compound 14, which is bisphosphonic acid having the same side chain, was simultaneously studied. First, EJ-1, 786-0, MKN1, OST, PC-3, PK-1, LK-2, G-361, TFK-1, MRK-nu-1 were cultured in RPMI1640 medium supplemented with 10% calf serum at 37° C. under 5% $CO_2$ atmosphere while maintaining log phase. The cells were recovered by a conventional EDTA trypsin treatment, and centrifuged at 1,700 rpm, 4° C. for 5 min. The supernatant was removed, and suspended in RPMI1640 medium supplemented with 10% calf serum to 500 cells/50 μl. On the other hand, 10 mM stock solution of compound 7 which is a bisphosphonic acid POM ester derivative was serially diluted 2-fold from 200 pM. In addition, 10 mM stock solution of compound 14 which is bisphosphonic acid was serially diluted 2-fold from 2 mM. Then, the cell suspension (50 μl, 500 cells) and the compound solution (50 μl) were added to a flat-bottomed 96 well plate and cultured at 37° C. under 5% $CO_2$ atmosphere for 4 days. Then, 100 μl of CellTiterGlo solution was added, and the mixture was pipetted 10 strokes, and transferred to a 96 well OptiPlate. After standing at room temperature for 10 min, the luminescence was measured by a luminometer and $IC_{50}$ value was calculated.

TABLE 4

Comparison of tumor growth inhibitory effects between POM esters and acid forms of nitrogen-containing bisphosphonates

| Tumor cell | Origin | POM:H | $IC_{50}$ (μM) | Ratio |
|---|---|---|---|---|
| EJ-1 | Bladder cancer | 7:14 | 0.026:3.7 | 1:142 |
| 786-0 | Renal cell carcinoma | 7:14 | 0.88:25 | 1:28 |
| MKN1 | Gastric cancer | 7:14 | 1.2:100 | 1:83 |
| OST | Osteosarcoma | 7:14 | 0.81:66 | 1:81 |
| PC-3 | Prostate cancer | 7:14 | 0.22:100 | 1:455 |
| PK-1 | Pancreatic cancer | 7:14 | 0.34:110 | 1:324 |
| LK-2 | Lung cancer | 7:14 | 0.80:35 | 1:44 |
| G-361 | Melanoma | 7:14 | 0.12:20 | 1:167 |
| TFK-1 | Cholangiocarcinoma | 7:14 | 0.10:30 | 1:300 |
| MRK-nu-1 | Mammary carcinoma | 7:14 | 0.74:210 | 1:284 |

As is clear from Table 4, bisphosphonic acid POM ester derivative showed several dozen to several hundred times higher activity than bisphosphonic acid. Therefrom it was clarified that POM esterification remarkably increases the antitumor activity of bisphosphonic acid.

Figure 4:
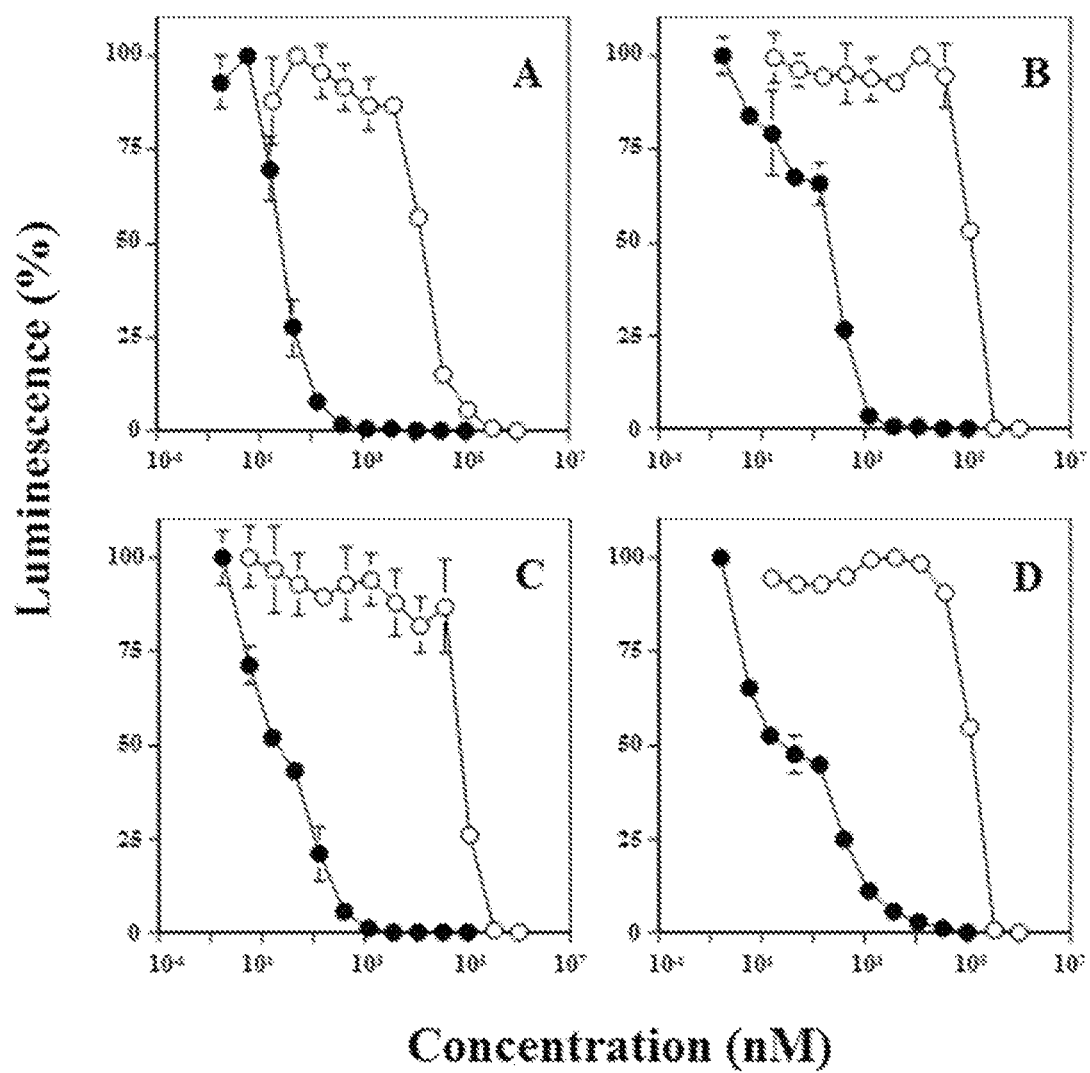
FIG. 4 is a graph showing the results of study using hematologic tumor cells, which verify that compound 7, which is a bisphosphonic acid POM ester derivative, has a high, direct antitumor action. As a comparison target, compound 14, which is bisphosphonic acid having the same side chain, was used.

Experimental Example 8 (FIG. 4)

The level of the direct antitumor activity of compound 7, which is a bisphosphonic acid POM ester derivative, on various hematologic tumor-derived lymphoma and myeloidic leukemia cells was examined. In this case, to study activity promoting action of POM esterification, the antitumor action of compound 14, which is bisphosphonic acid having the same side chain, was simultaneously studied by comparison in various tumor cells. First, K562, MOLT-4, PEER, THP-1 were cultured in RPMI1640 medium supplemented with 10% calf serum at 37° C. under 5% $CO_2$ atmosphere while maintaining log phase. The cells were recovered, and centrifuged at 1,700 rpm, 4° C. for 5 min. The supernatant was removed, and suspended in RPMI1640 medium supplemented with 10% calf serum to 500 cells/50 μl. On the other hand, 10 mM stock solution of compound 7 which is a bisphosphonic acid POM ester derivative was serially diluted 2-fold from 200 μM. In addition, 10 mM stock solution of compound 14 which is bisphosphonic acid was serially diluted 2-fold from 2 mM. Then, the cell suspension (50 μl, 500 cells) and the compound solution (50 μl) were added to a flat-bottomed 96 well plate and cultured at 37° C. under 5% $CO_2$ atmosphere for 4 days. Then, 100 μl of CellTiterGlo solution was added, and the mixture was pipetted 10 strokes, and transferred to a 96 well OptiPlate. After standing at room temperature for 10 min, the luminescence was measured by a luminometer.

FIG. 4A shows K562, FIG. 4B shows MOLT-4, FIG. 4C shows PEER, and FIG. 4D shows THP-1. The results of compound 7 are shown by -●-, and the results of compound 14 are shown by -○-. As is clear from FIG. 4, bisphosphonic acid POM ester derivative showed a higher activity than bisphosphonic acid in any hematologic tumor cells. Therefrom it was clarified that POM esterification remarkably increases the antitumor activity of bisphosphonic acid.

Experimental Example 9 (Table 5)

To quantitatively study an action of compound 7, which is a bisphosphonic acid POM ester derivative, on various hematologic tumor-derived lymphoma and myeloidic leukemia cells, the concentration of a compound that inhibits cell proliferation to half was calculated as $IC_{50}$, and a direct antitumor effect was studied from the value thereof. In this case, to study activity promoting action of POM esterification, the antitumor action of compound 14, which is bisphosphonic acid having the same side chain, was simultaneously studied by comparison in various tumor cells. First, MOLT-4, THP-1, SCC-3, PEER, RAMOS-RA1, C1R, MOLT-3, Raji, U937, K562, Daudi were cultured in RPMI1640 medium supplemented with 10% calf serum at 37° C. under 5% $CO_2$ atmosphere while maintaining log phase. The cells were recovered, and centrifuged at 1,700 rpm, 4° C. for 5 min. The supernatant was removed, and suspended in RPMI1640 medium supplemented with 10% calf serum to 500 cells/50 μl. On the other hand, 10 mM stock solution of compound 7 which is a bisphosphonic acid POM ester derivative was serially diluted 2-fold from 200 μM. In addition, 10 mM stock solution of compound 14 which is bisphosphonic acid was serially diluted 2-fold from 2 mM. Then, the cell suspension (50 μl, 500 cells) and the compound solution (50 μl) were added to a flat-bottomed 96 well plate and cultured at 37° C. under 5% $CO_2$ atmosphere for 4 days. Then, 100 μl of CellTiterGlo solution was added, and the mixture was pipetted 10 strokes, and transferred to a 96 well OptiPlate. After standing at room temperature for 10 min, the luminescence was measured by a luminometer and $IC_{50}$ value was calculated.

TABLE 5

Comparison of tumor growth inhibitory effects between POM esters and acid forms of nitrogen-containing bisphosphonates

| Tumor cell | Origin | POM:H | IC$_{50}$ (μM) | Ratio |
|---|---|---|---|---|
| MOLT-4 | Acute lymphoblastic leukemia | 7:14 | 0.16:120 | 1:750 |
| THP-1 | Acute monocytic leukemia | 7:14 | 0.035:130 | 1:3714 |
| SCC-3 | Non-Hodgkin's lymphoma | 7:14 | 0.18:66 | 1:367 |
| PEER | T cell acute lymphocytic leukemia | 7:14 | 0.023:82 | 1:3565 |
| PAMOS-RA1 | Burkitt's lymphoma | 7:14 | 0.11:75 | 1:682 |
| C1R | B cell lymphoma | 7:14 | 0.078:79 | 1:1013 |
| MOLT-3 | Acute lymphoblastic leukemia | 7:14 | 0.13:180 | 1:1385 |
| Raji | Burkitt's lymphoma | 7:14 | 0.27:120 | 1:444 |
| U937 | Histiocytic lymphoma | 7:14 | 0.26:26 | 1:100 |
| K562 | Erythromcytoma | 7:14 | 0.029:16 | 1:552 |
| Daudi | Burkitt's lymphoma | 7:14 | 0.43:76 | 1:177 |

As is clear from Table 5, bisphosphonic acid POM ester derivative showed several hundred to several thousand times higher activity than bisphosphonic acid. Therefrom it was clarified that POM esterification remarkably increases the antitumor activity of bisphosphonic acid. In addition, it was clarified that the effect of POM esterification is remarkable in hematologic tumor cells.

Figure 5:
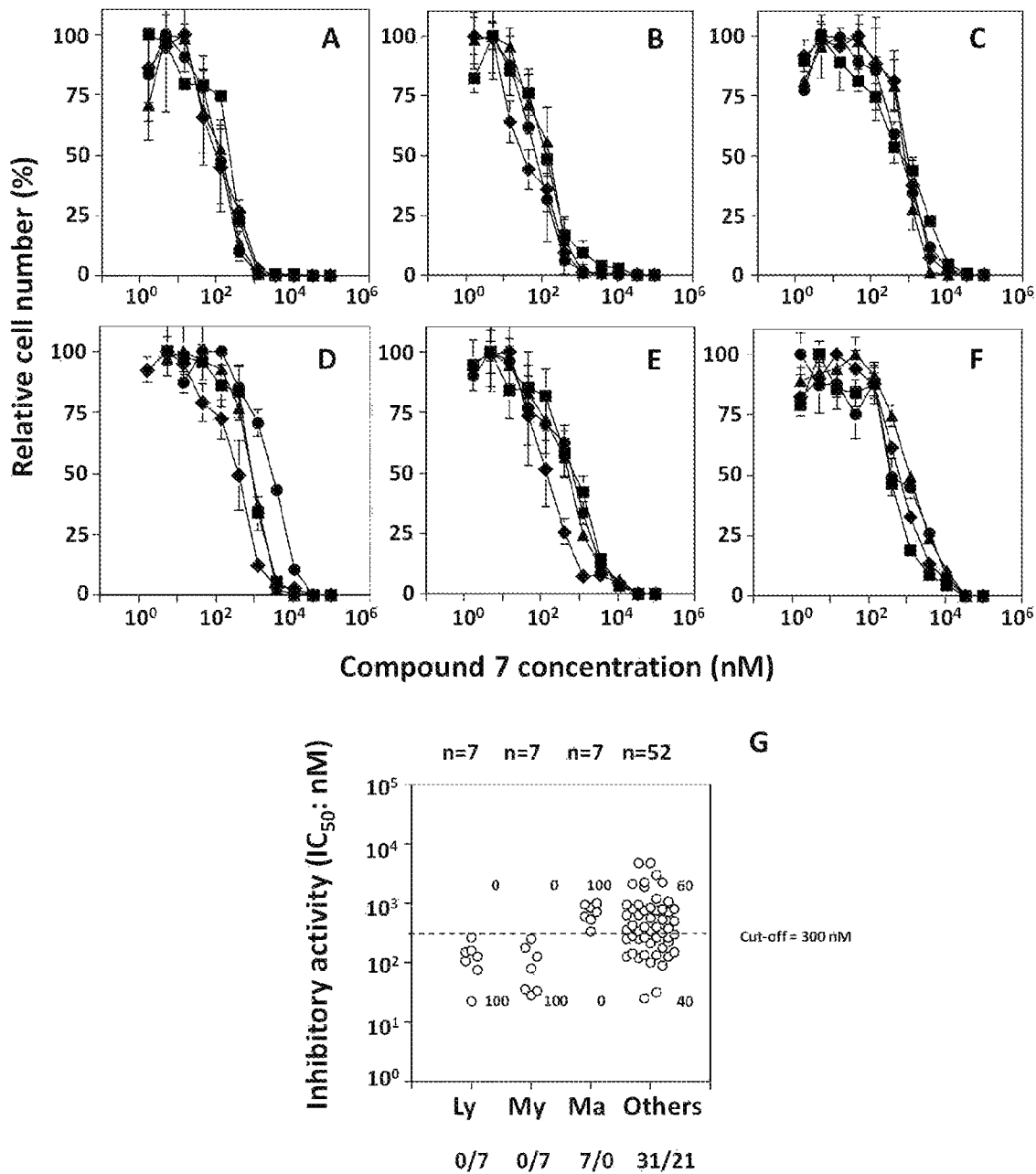
FIG. 5 is a graph showing the results of study of direct tumor cytotoxicity of compound 7, which is a bisphosphonic acid POM ester derivative, against various tumor cell lines. FIG. A shows the results against lymphomatous tumor cells (MOLT-3, J.RT3-T3.5, Raji, RAMOS-RA1). FIG. B shows the results against myeloid line tumor cells (HL60, SCC-3, P31/FUJ, NOMO-1). FIG. C shows the results against breast cancer-derived tumor cells (YMB-1-E, HMC-1-8, MCF-7, MDA-MB-231). FIG. D shows the results against renal cancer-derived tumor cells (VMRC-RCW, UOK121, Caki-1, A-704). FIG. E shows the results against pancreatic cancer-derived tumor cells (KP4-1, KP4-2, KP4-3, MiaPaCa-2). FIG. F shows the results against other cancer-derived tumor cells (TGBC24TKB, MKN1, Colo320, TAKAO). FIG. G shows the results of quantitative study of the action on total 73 kinds of tumor cell lines that underwent a similar test.

Experimental Example 10 (FIG. 5)

From the results of the above-mentioned Experimental Examples, a higher direct antitumor activity of the bisphosphonic acid POM ester derivative than that of bisphosphonic acid, which is a conventional acid, was confirmed in hematologic tumor cells and a part of solid tumor-derived cell line. Therefore, direct tumor cytotoxicity of compound 7, which is a bisphosphonic acid POM ester derivative, against more number of tumor cell lines was studied. To quantitatively study an action on RAMOS-RA1, Raji, J.RT3-T3.5, MOLT-3, HL60, NOMO-1, SCC-3, P31/FUJ, HMC-1-8, MCF-7, MDA-MB-231, YMB-1-E, A-704, Caki-1, UOK121, VMRC-RCW, TGBC24TKB, MKN1, KP4-1, KP4-2, KP4-3, MIAPaCa-2, TAKAO, Colo320, the concentration of a compound that inhibits cell proliferation to half was calculated as IC$_{50}$, and a direct antitumor effect was studied from the value thereof. The above-mentioned cells were cultured in RPMI1640 medium supplemented with 10% calf serum at 37° C. under 5% CO$_2$ atmosphere while maintaining log phase. The cells were recovered, and centrifuged at 1,700 rpm, 4° C. for 5 min. The supernatant was removed, and suspended in RPMI1640 medium supplemented with 10% calf serum to 500 cells/50 μl. On the other hand, 10 mM stock solution of compound 7, which is a bisphosphonic acid POM ester derivative, was serially diluted 2-fold from 200 μM. In addition, 10 mM stock solution of compound 14, which is bisphosphonic acid, was serially diluted 2-fold from 2 mM. Then, the cell suspension (50 μl, 500 cells) and the compound solution (50 μl) were added to a flat-bottomed 96 well plate and cultured at 37° C. under 5% CO$_2$ atmosphere for 4 days. Then, 100 μl of CellTiterGlo solution was added, and the mixture was pipetted 10 strokes, and transferred to a 96 well OptiPlate. After standing at room temperature for 10 min, the luminescence was measured by a luminometer and IC$_{50}$ value was calculated.

FIG. 5A shows the results of lymphomatous tumor cells.
-●-MOLT-3、-▲-J. RT3-T3.5、
-■-Raji、-♦-RAMOS-RA1
FIG. 5B shows the results of myeloidic tumor cells.
-●-HL60、-▲-SCC-3、-■-P31/FUJ、-♦-NOMO-1
FIG. 5C shows the results of breast cancer-derived tumor cells.
-●-YMB-1-E、-▲-HMC-1-8、
-■-MCF-7、-♦-MDA-MB-231
FIG. 5D shows the results of renal cancer-derived tumor cells.
-●-VMRC-RCW、-▲-UOK121、
-■-Caki-1、-♦-A-704
FIG. 5E shows the results of pancreatic cancer-derived tumor cells.
-●-KP4-1、-▲-KP4-2、
-■-KP4-3、-♦-MiaPaCa-2
FIG. 5F shows the results of other cancer-derived tumor cells.
-●- gallbladder cancer-derived TGBC1TKB cells,
-▲- gastric cancer-derived MKN1 cells
-■- large intestine cancer-derived Colo320 cells
-♦- osteosarcoma-derived TAKAO cells From these results, compound 7, which is a bisphosphonic acid POM ester derivative, showed direct cytotoxicity against all the studied tumor cells.

Then, based in the results of FIG. 5A to FIG. 5F, a similar test was performed for a total of 73 kinds of tumor cell lines shown below and, to quantitatively study the action thereon, the concentration of a compound that inhibits cell proliferation to half was calculated as IC$_{50}$ and a direct antitumor effect was studied from the value thereof. Those values were plotted in FIG. 5G. The tumor cells studied were as follows. C1R, RAMOS-RA1, Raji, J.RT3-T3.5, MOLT-3, MOLT-4, PEER (hereinafter lymphomatous tumor cells: Ly), HL60, NOMO-1, SCC-3, THP-1, U937, P31/FUJ, K562 (hereinafter myeloidic tumor cells: My), HMC-1-8, MCF-7, MDA-MB-231, MRK-nu-1, SK-BR-3, T-47D, YMB-1-E (hereinafter breast cancer-derived tumor cells: Ma), 786-0, 786-0W, A-704, ACHN, Caki-1, UOK111, UOK121, VMRC-RCW, VMRC-RCZ, EJ-1, T24, TGBC1TKB, TGBC2TKB, TGBC24TKB, HuCCT1, MZChA2, TFK-1, ACS, AGS, GCIY, KATOIII, MKN1, MKN28, MKN74, AsPC-1, BxPC-3, KP4-1, KP4-2, KP4-3, MIAPaCa-2, PANC-1, PK-1, PK-8, PK-9, T3M4, HOS, HuO, MG-63, OST, SaOS-2, TAKAO, Colo320, CW2, DLD-1, C32TG, G-361, LK-2, SBC-2, hu2, GCT-IZ, PC-3, HT-1080 (hereinafter other tumor cells: Others).

From these results, it was clarified that lymphocytic tumor cells and myeloidic tumor cells showed high sensitivity to bisphosphonic acid POM ester derivative.

Figure 6:
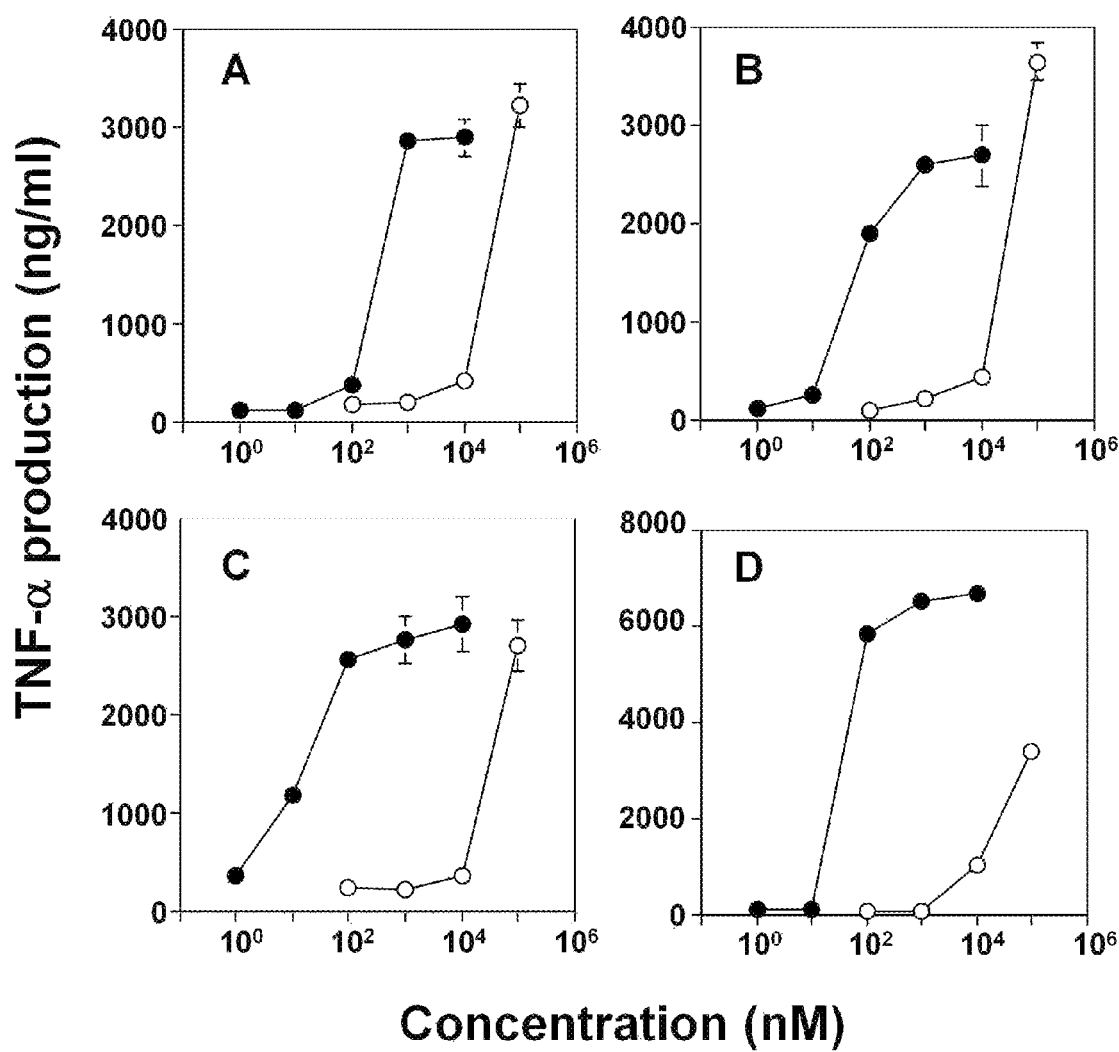
FIG. 6 is a graph showing the results of comparison study of the indirect antitumor action of bisphosphonic acid POM ester derivatives (compounds 3, 5, 6, 7) and bisphosphonic acids corresponding thereto (compounds 10, 12, 13, 14) by using bladder cancer-derived EJ-1 cells.

Experimental Example 11 (FIG. 6)

The indirect antitumor action of bisphosphonic acid POM esters and bisphosphonic acids was studied by comparison using EJ-1. In principle, EJ-1 is treated with a compound, washed, and reacted with γδ T cells, and the cytotoxic ability is studied by comparison, by quantifying TNF-α produced by γδ T cells during cell disordering. TNF-α is generally used as an index of γδ T cell induction ability and/or proliferative capacity, and γδ T cells are considered to be induced and/or proliferated in proportion to the TNF-α amount (Journal of Immunology, 154, 5986-5994 (1995)). Since the produced TNF-α is what is called a tumor necrosis factor, it is considered to have an action to lower proliferation of cancer cells or induce cell death.

First, EJ-1 was cultured in RPMI1640 medium supplemented with 10% calf serum at 37° C. under 5% $CO_2$ atmosphere while maintaining log phase. The cells were recovered, and centrifuged at 1,700 rpm, 4° C. for 5 min. The supernatant was removed, suspended in RPMI1640 medium supplemented with 10% calf serum to $1 \times 10^6$ cells/500 μl, and dispensed to a 15 ml conical tube by 500 μl. These conical tubes were centrifuged at 1,700 rpm, 4° C. for 5 min, and the supernatant was removed. Thereto was added a solution (500 μl) of compounds 3, 5, 6, 7, which are bisphosphonic acid POM ester derivatives, obtained by serially diluting 10 mM stock solution 10-fold from 20 μM, or a solution (500 μl) of bisphosphonic acid 10, 12, 13, 14 compound obtained by serially diluting 10-fold from 200 μM, and the cells were suspended well. These conical tubes were stood at 37° C. for 4 hr, and the cells were washed 3 times with 5 ml of culture medium. To these cells was added 500 μl of medium, and the cells were suspended well. Then, compound-treated EJ-1 cell suspension (100 μl, $2 \times 10^5$ cells) and γδ T cell suspension (100 μl, $2 \times 10^5$ cells) prepared to $1 \times 10^6$ cells/500 μl were added to a round-bottomed 96 well plate, and cells were cultured at 37° C. under 5% $CO_2$ atmosphere for 16 hr. The cell culture medium was suspended well, and the plate was centrifuged at 1,700 rpm, 4° C. for 2 min and the culture supernatant (150 μl) was taken and placed in another round-bottomed 96 well plate. The plate was frozen at −80° C. overnight, left standing at room temperature for 1 hr, stirred well and 100 μl thereof was subjected to ELISA of TNF-α. The content of TNF-α was calculated from the analytical curve of TNF-α. These were performed in triplicate, and a graph showing bisphosphonic acid POM ester derivative and the corresponding bisphosphonic acid as one pair was plotted. FIG. 6A shows a combination of compounds 3:10, FIG. 6B shows a combination of compounds 5:12, FIG. 6C shows a combination of compounds 6:13, and FIG. 6D shows a combination of compounds 7:14. The results of bisphosphonic acid POM ester derivative are shown by -●-, and the results of bisphosphonic acid are shown by -○-. As is clear from FIG. 6, bisphosphonic acid POM ester showed a higher TNF-α production induction ability than bisphosphonic acid in compounds having any side chain, that is, it was clarified that it shows high indirect cytotoxic ability.

Experimental Example 12 (Table 6)

The indirect antitumor action of bisphosphonic acid POM esters and bisphosphonic acids was quantitatively studied by comparison using EJ-1. First, EJ-1 was cultured in RPMI1640 medium supplemented with 10% calf serum at 37° C. under 5% $CO_2$ atmosphere while maintaining log phase. The cells were recovered, and centrifuged at 1,700 rpm, 4° C. for 5 min. The supernatant was removed, suspended in RPMI1640 medium supplemented with 10% calf serum to $1 \times 10^6$ cells/500 μl, and dispensed to a 15 ml conical tube by 500 μl. These conical tubes were centrifuged at 1,700 rpm, 4° C. for 5 min, and the supernatant was removed. Thereto was added a solution (500 μl) of a bisphosphonic acid POM ester derivative obtained by serially diluting 10 mM stock solution 10-fold from 20 μM, or a bisphosphonic acid solution (500 μl) serially diluted 10-fold from 200 μM was added, and the cells were suspended well. These conical tubes were stood at 37° C. for 4 hr, and the cells were washed 3 times with 5 ml of culture medium. To these cells was added 500 μl of medium, and the cells were suspended well. Then, compound-treated EJ-1 cell suspension (100 μl, $2 \times 10^5$ cells) and γδ T cell suspension (100 μl, $2 \times 10^5$ cells) prepared to $1 \times 10^6$ cells/500 μl were added to a round-bottomed 96 well plate, and cells were cultured at 37° C. under 5% $CO_2$ atmosphere for 16 hr. The cell culture medium was suspended well, and the plate was centrifuged at 1,700 rpm, 4° C. for 2 min and the culture supernatant (150 μl) was taken and placed in another round-bottomed 96 well plate. The plate was frozen at −80° C. overnight, left standing at room temperature for 1 hr, stirred well and 100 μl thereof was subjected to ELISA of TNF-α. The content of TNF-α was calculated from the analytical curve of TNF-α. These were performed in triplicate, and a half of the concentration of compounds 1-7, which are bisphosphonic acid POM ester derivatives, and compounds 8-14, which are bisphosphonic acids, necessary for producing the maximum amount of TNF-α from γδ T cells was calculated as TNF-$α_{50}$, and summarized in Table 6. As is clear from Table 6, bisphosphonic acid POM ester derivatives showed 140 to 1,100 times higher TNF-α induction activity as compared to the corresponding bisphosphonic acid.

TABLE 6

Effect of POM esters and acid forms of nitrogen-containing bisphosphonates on TNF-α production from γδ T cells stimulated by EJ-1

| POM:H | TNF-$α_{50}$ (nM) | Ratio |
|---|---|---|
| 1:8 | 550:>100,000 | 1:>180 |
| 2:9 | 4,500:>100,000 | 1:>20 |
| 3:10 | 480:48,000 | 1:100 |
| 4:11 | 700:>100,000 | 1:>140 |
| 5:12 | 69:49,000 | 1:710 |
| 6:13 | 80:48,000 | 1:600 |
| 7:14 | 60:68,000 | 1:1,100 |

Experimental Example 13 (Table 7)

From the results of the above-mentioned Experimental Example, it was clarified that the bisphosphonic acid POM ester derivative is superior in the indirect antitumor action to the corresponding bisphosphonic acid. Therefore, the TNF-$α_{50}$ value of various bisphosphonic acid POM ester derivatives was calculated. First, EJ-1 was cultured in RPMI1640 medium supplemented with 10% calf serum at 37° C. under 5% $CO_2$ atmosphere while maintaining log phase. The cells were recovered, and centrifuged at 1,700 rpm, 4° C. for 5 min. The supernatant was removed, suspended in RPMI1640 medium supplemented with 10% calf serum to $1 \times 10^6$ cells/500 μl, and dispensed to a 15 ml conical tube by 500 μl. These conical tubes were centrifuged at 1,700 rpm, 4° C. for 5 min, and the supernatant was removed. Thereto was added a solution (500 μl) of compounds 1-7 and 15-39, which are bisphosphonic acid POM ester derivatives, and compound 42, which is other bisphosphonic acid ester derivative, obtained by serially diluting 10 mM stock solution 10-fold from 20 μM, and the cells were suspended well. These conical tubes were stood at 37° C. for 4 hr, and the cells were washed 3 times with 5 ml of culture medium. To these cells was added 500 μl of medium, and the cells were suspended well. Then, compound-treated EJ-1 cell suspension (100 μl, 2×10⁵ cells) and γδ T cell suspension (100 μl, 2×10⁵ cells) prepared to 1×10⁶ cells/500 μl were added to a round-bottomed 96 well plate, and cells were cultured at 37° C. under 5% $CO_2$ atmosphere for 16 hr. The cell culture medium was suspended well, and the plate was centrifuged at 1,700 rpm, 4° C. for 2 min and the culture supernatant (150 μl) was taken and placed in another round-bottomed 96 well plate. The plate was frozen at −80° C. overnight, left standing at room temperature for 1 hr, stirred well and 100 μl thereof was subjected to ELISA of TNF-α. The content of TNF-α was calculated from the analytical curve of TNF-α. These were performed in triplicate, and a half of the concentration of bisphosphonic acid POM ester derivative, necessary for producing the maximum amount of TNF-α from γδ T cells was calculated as TNF-$α_{50}$, and summarized in Table 7. As is clear from Table 7, of the bisphosphonic acid POM ester derivatives, compounds 7, 39, 34, 5, 6 showed high activity.

TABLE 7

TNF-α production by γδ T cells in response to EJ-1 cells pretreated with POM of nitrogen-containing bisphosphonates

| Compound | TNF-$α_{50}$ (nM) |
|---|---|
| 7 | 60 |
| 39 | 62 |
| 34 | 63 |
| 5 | 69 |
| 6 | 80 |
| 18 | 380 |
| 3 | 480 |
| 1 | 550 |
| 4 | 700 |
| 31 | 1,600 |
| 38 | 1,900 |
| 23 | 3,400 |
| 33 | 3,600 |
| 20 | 3,700 |
| 32 | 4,400 |
| 2 | 4,500 |
| 27 | 4,600 |
| 22 | 4,800 |
| 16 | 5,100 |
| 28 | 6,500 |
| 42 | 7,100 |
| 36 | 8,000 |
| 15 | >10,000 |
| 17 | >10,000 |
| 19 | >10,000 |
| 21 | >10,000 |
| 24 | >10,000 |
| 25 | >10,000 |
| 26 | >10,000 |
| 29 | >10,000 |
| 30 | >10,000 |
| 35 | >10,000 |
| 37 | >10,000 |

Figure 7:
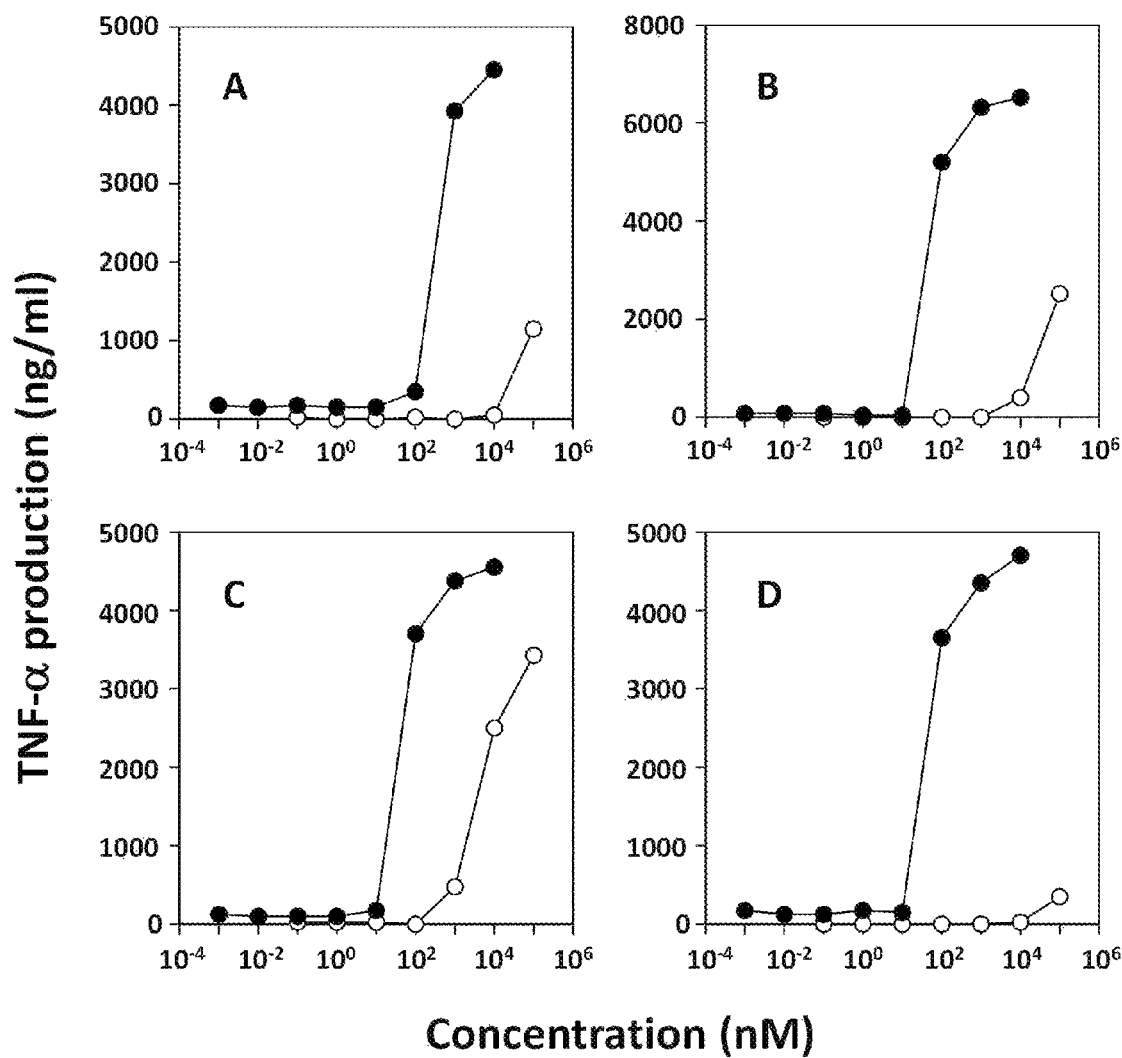
FIG. 7 is a graph showing the results of study using various carcinoma cells, which verify that compound 7, which is a bisphosphonic acid POM ester derivative, has a high TNF-α production induction ability. As a comparison target, compound 14, which is bisphosphonic acid having the same side chain, was used.

Experimental Example 14 (FIG. 7)

From the results of the above-mentioned Experimental Example, of the bisphosphonic acid POM ester derivatives, since the activity of compound 7 was high, the TNF-α production induction ability of this compound was studied using tumor cells other than EJ-1. In this case, to study effectiveness of POM esterification, using compound 14, which is the corresponding bisphosphonic acid, as a control to be the comparison target. First, gastric cancer-derived MKN1, prostate cancer-derived PC-3, malignant melanoma-derived G-361, biliary cancer-derived TFK-1 were cultured in RPMI1640 medium supplemented with 10% calf serum at 37° C. under 5% $CO_2$ atmosphere while maintaining log phase. Respective cells were recovered, and centrifuged at 1,700 rpm, 4° C. for 5 min. The supernatant was removed, suspended in RPMI1640 medium supplemented with 10% calf serum to 1×10⁶ cells/500 μl, and dispensed to a 15 ml conical tube by 500 μl. These conical tubes were centrifuged at 1,700 rpm, 4° C. for 5 min, and the supernatant was removed. Thereto was added a solution (500 μl) of compound 7 obtained by serially diluting 10 mM stock solution 10-fold from 20 μM, or a solution (500 μl) of compound 14 obtained by serially diluting 10 mM stock solution 10-fold from 200 μM, and the cells were suspended well. These conical tubes were stood at 37° C. for 4 hr, and the cells were washed 3 times with 5 ml of culture medium. To these cells was added 500 μl of medium, and the cells were suspended well. Then, compound-treated tumor cell suspension (100 μl, 2×10⁵ cells) and γδ T cell suspension (100 μl, 2×10⁵ cells) prepared to 1×10⁶ cells/500 μl were added to a round-bottomed 96 well plate, and cells were cultured at 37° C. under 5% $CO_2$ atmosphere for 16 hr. The cell culture medium was suspended well, and the plate was centrifuged at 1,700 rpm, 4° C. for 2 min and the culture supernatant (150 μl) was taken and placed in another round-bottomed 96 well plate. The plate was frozen at −80° C. overnight, left standing at room temperature for 1 hr, stirred well and 100 μl thereof was subjected to ELISA of TNF-α. The content of TNF-α was calculated from the analytical curve of TNF-α. These were performed in triplicate, and bisphosphonic acid POM ester derivative (compound 7) and bisphosphonic acid (compound 14) are summarized in Table 7. Relating to compounds 7 and 14, FIG. 7A shows the results of MKN1, FIG. 7B shows the results of PC-3, FIG. 7C shows the results of G-361, and FIG. 7D shows the results of TFK-1. The results of bisphosphonic acid POM ester derivative are shown by -●-, and the results of bisphosphonic acid are shown by -○-. As is clear from FIG. 7, it was clarified that the TNF-α production induction ability becomes high by POM esterification in any tumor cells.

Experimental Example 15 (Table 8)

Since the above-mentioned results of Experimental Example confirm that the activity of bisphosphonic acids becomes high by POM esterification in various tumor cells, the TNF-α production induction ability of more number of tumor cells was quantitatively studied. Various tumor cells described in Table 8 were cultured in RPMI1640 medium supplemented with 10% calf serum at 37° C. under 5% $CO_2$ atmosphere while maintaining log phase. Respective cells were recovered, and centrifuged at 1,700 rpm, 4° C. for 5 min. The supernatant was removed, suspended in RPMI1640 medium supplemented with 10% calf serum to 1×10⁶ cells/500 μl, and dispensed to a 15 ml conical tube by 500 μl. These conical tubes were centrifuged at 1,700 rpm, 4° C. for 5 min, and the supernatant was removed. Thereto was added a solution (500 μl) of compound 7 obtained by serially diluting 10 mM stock solution 10-fold from 20 μM, or a solution (500 μl) of compound 14 obtained by serially diluting 10 mM stock solution 10-fold from 200 μM, and the cells were suspended well. These conical tubes were stood at 37° C. for 4 hr, and the cells were washed 3 times with 5 ml of culture medium. To these cells was added 500 μl of medium, and the cells were suspended well. Then, compound-treated tumor cell suspension (100 μl, 2×10⁵ cells) and γδ T cell suspension (100 μl, 2×10⁵ cells) prepared to $1\times10^6$ cells/500 μl were added to a round-bottomed 96 well plate, and cells were cultured at 37° C. under 5% $CO_2$ atmosphere for 16 hr. The cell culture medium was suspended well, and the plate was centrifuged at 1,700 rpm, 4° C. for 2 min and the culture supernatant (150 μl) was taken and placed in another round-bottomed 96 well plate. The plate was frozen at −80° C. overnight, left standing at room temperature for 1 hr, stirred well and 100 μl thereof was subjected to ELISA of TNF-α. The content of TNF-α was calculated from the analytical curve of TNF-α. These were performed in triplicate, and TNF-$α_{50}$ of bisphosphonic acid POM ester derivative (compound 7) and bisphosphonic acid (compound 14) was calculated and summarized in Table 8. As is clear from Table 8, it was clarified that the TNF-α production induction ability becomes high by POM esterification in any tumor cells.

TABLE 8

Effect of POM protection of a nitrogen-containing bisphosphonate on TNF-α production from γδ T cells stimulated by EJ-1

| Tumor cell | Origin | POM:H | TNF-$α_{50}$ (nM) | Ratio |
|---|---|---|---|---|
| 786-0 | Renal cell carcinoma | 7:14 | 65:>100,000 | 1:>1,500 |
| MKN1 | Gastric cancer | 7:14 | 560:89,000 | 1:160 |
| OST | Osteosarcoma | 7:14 | 600:>100,000 | 1:>170 |
| PC-3 | Prostate cancer | 7:14 | 65:77,000 | 1:1,200 |
| PK1 | Pancreatic cancer | 7:14 | 450:>100,000 | 1:>200 |
| LK-2 | Lung cancer | 7:14 | 97:>100,000 | 1:>1,000 |
| G-361 | Melanoma | 7:14 | 63:5,100 | 1:81 |
| TFK-1 | Cholangio- carcinoma | 7:14 | 66:>100,000 | 1:>1,500 |
| U937 | Histiocytic lymphoma | 7:14 | 60:>100,000 | 1:>1,700 |
| K562 | Erythrocytoma | 7:14 | 80:>100,000 | 1:>1,300 |
| C1R | B cell lymphoma | 7:14 | 530:>100,000 | 1:>190 |
| SCC-3 | Non-Hodgkin's lymphoma | 7:14 | 81:>100,000 | 1:>1,200 |
| MOLT-4 | Acute lymphoblastic leukemia | 7:14 | 59:>100,000 | 1:>1,700 |
| PEER | T cell acute lymphocytic leukemia | 7:14 | 83:>100,000 | 1:>1,200 |
| MOLT-3 | Acute lymphoblastic leukemia | 7:14 | 66:>100,000 | 1:>1,500 |
| THP-1 | Acute monocytic leukemia | 7:14 | 300:>100,000 | 1:>330 |
| Raji | Burkitt's lymphoma | 7:14 | 53:>100,000 | 1:>1,900 |
| RAMOS-RA1 | Burkitt's lymphoma | 7:14 | 140:>100,000 | 1:>700 |
| HMC-1-8 | Mammary carcinoma | 7:14 | 920:>100,000 | 1:>110 |
| YMB-1-E | Mammary carcinoma | 7:14 | 630:>100,000 | 1:>160 |
| MRK-nu-1 | Mammary carcinoma | 7:14 | 180:>100,000 | 1:>560 |

Figure 8:
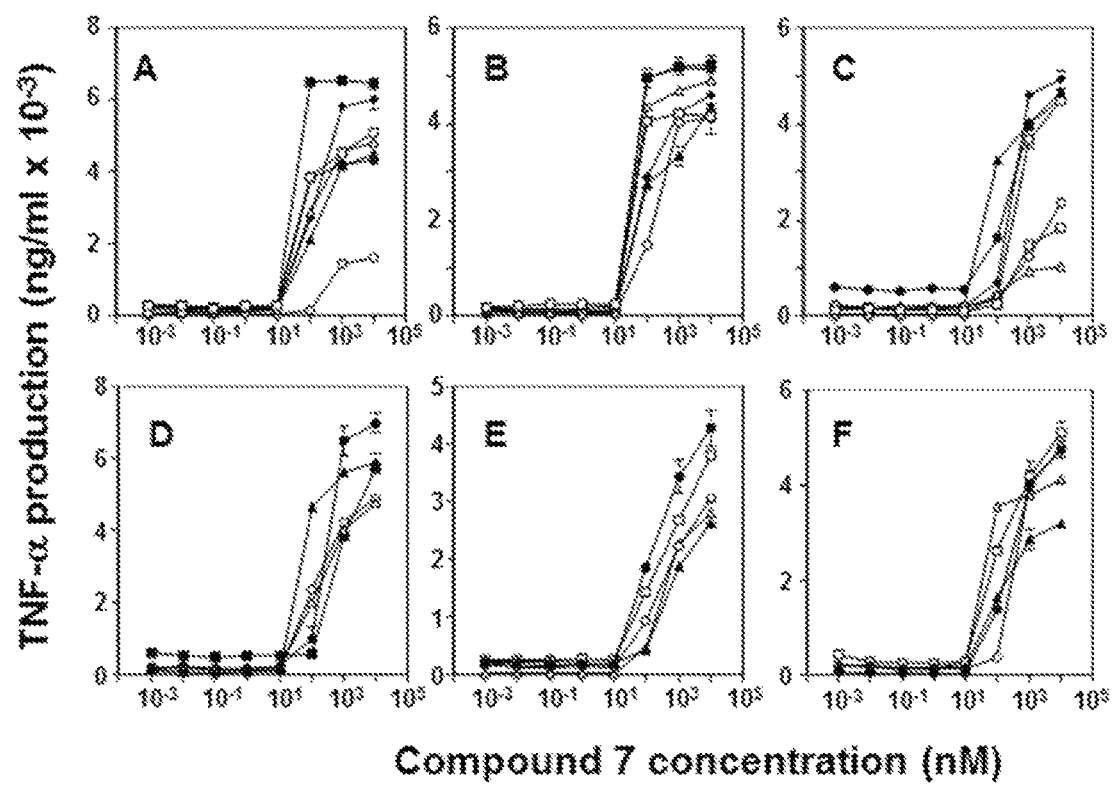
FIG. 8 is a graph showing the results of study of TNF-α production induction ability of compound 7, which is a bisphosphonic acid POM ester derivative, in various tumor cell lines. FIG. A shows the results in lymphomatous tumor cells (MOLT-3, PEER, C2R, J.RT3-T3.5, Raji, RAMOS-RA1, MOLT-4). FIG. B shows the results in myeloidic tumor cells (HL60, U937, THP-1, SCC-3, P31/FUJ, K562, NOMO-1). FIG. C shows the results in breast cancer-derived tumor cells (YMB-1-E, MRK-nu-1, HMC-1-8, MCF-7, MDA-MB-231, T-47D, SK-BR-3). FIG. D shows the results in renal cancer-derived tumor cells (786-0, VMRC-RCZ, UOK121, Caki-1, A-704). FIG. E shows the results in pancreatic cancer-derived tumor cells (BxPC-3, KP4-1, KP4-2, KP4-3, MiaPaCa-2). FIG. F shows the results in other cancer-derived tumor cells (TGBC24TKB, ACS, MG-63, LK-2, C32TG). FIG. G shows the results of quantitative study of the action on many kinds of tumor cell lines that underwent a similar test.
Figure 8:
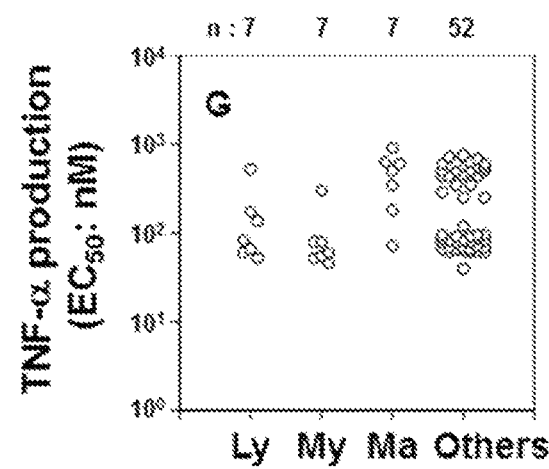

Experimental Example 16 (FIG. 8)

From the results of the above-mentioned Experimental Example, it was clarified that compound 7, which is a bisphosphonic acid POM ester derivative, has high TNF-α production induction ability. Therefore, TNF-α production induction ability of compound 7 was studied in more number of tumor cell lines. First, using MOLT-3, PEER, C1R, J.RT3-T3.5, Raji, RAMOS-RA1, MOLT-4, HL60, U937, THP-1, SCC-3, P31/FUJ, K562, NOM0-1, YMB-1-E, MRK-nu-1, HMC-1-8, MCF-7, MDA-MB-231, T-47D, SK-BR-3, 786-0, VMRC-RCZ, UOK121, Caki-1, A-704, BxPC-3, KP4-1, KP4-2, KP4-3, MiaPaCa-2, TGBC24TKB, ACS, MG-63, LK-2, C32TG, these cells were cultured in RPMI1640 medium supplemented with 10% calf serum at 37° C. under 5% $CO_2$ atmosphere while maintaining log phase. Respective cells were recovered, and centrifuged at 1,700 rpm, 4° C. for 5 min. The supernatant was removed, suspended in RPMI1640 medium supplemented with 10% calf serum to $1\times10^6$ cells/500 μl, and dispensed to a 15 ml conical tube by 500 μl. These conical tubes were centrifuged at 1,700 rpm, 4° C. for 5 min, and the supernatant was removed. Thereto was added a solution (500 μl) of compound 7 obtained by serially diluting 10 mM stock solution 10-fold from 20 μM, and the cells were suspended well. These conical tubes were stood at 37° C. for 4 hr, and the cells were washed 3 times with 5 ml of culture medium. To these cells was added 500 μl of medium, and the cells were suspended well. Then, compound-treated tumor cell suspension (100 μl, $2\times10^5$ cells) and γδ T cell suspension (100 μl, $2\times10^5$ cells) prepared to $1\times10^6$ cells/500 μl were added to a round-bottomed 96 well plate, and cells were cultured at 37° C. under 5% $CO_2$ atmosphere for 16 hr. The cell culture medium was suspended well, and the plate was centrifuged at 1,700 rpm, 4° C. for 2 min and the culture supernatant (150 μl) was taken and placed in another round-bottomed 96 well plate. The plate was frozen at −80° C. overnight, left standing at room temperature for 1 hr, stirred well and 100 μl thereof was subjected to ELISA of TNF-α. The content of TNF-α was calculated from the analytical curve of TNF-α. These were performed in triplicate, and summarized in FIG. 8.

FIG. 8A shows the results of lymphomatous tumor cells. -●-MOLT-3、-▲-PEER、-■-C1R、-◆-J. RT3.5、 -○-Raji、-△-RAMOS-RA1、-□-MOLT-4

FIG. 8B shows the results of myeloidic tumor cells. -●-HL60 、-▲-U937、-■-THP-1、-◆-SCC-3、 -○-P31/FUJ、-△-K562、-□-NOMO-1

FIG. 8C shows the results of breast cancer-derived tumor cells.
-●-YMB-1-E、-▲-MRK-nu-1、-■-HMC-1-8、 -◆-MCF-7、-○-MDA-MB-231、-△-T-47D、 -□-SK-BR-3

FIG. 8D shows the results of renal cancer-derived tumor cells.
-●-786-0、-▲-VMRC-RCZ、-■-UOK121、 -○-Caki-1、-△-A-704

FIG. 8E shows the results of pancreatic cancer-derived tumor cells.
-●-BxPC-3、-▲-KP4-1、-○-KP4-2、 -△-KP4-3、-□-MiaPaCa-2、

FIG. 8F shows the results of other cancer-derived tumor cells.
-●-TGBC24TKB、-▲-ACS、-○-MG-63、 -△-LK-2、-□-C32TG From these results, the treatment with compound 7 enabled efficient induction of TNF-α production from γδ T cells in any cell line. To quantitatively study the above-mentioned TNF-α production induction ability, various tumor cell lines were treated with compound 7, reacted with γδ T cells, the produced TNF-α amount was measured, and TNF-$α_{50}$ value thereof was calculated. The tumor cells studied were as follows.
C1R, RAMOS-RA1, Raji, J.RT3-T3.5, MOLT-3, MOLT-4, PEER (hereinafter lymphomatous tumor cells: Ly), HL60, NOMO-1, SCC-3, THP-1, U937, P31/FUJ, K562 (hereinafter myeloidic tumor cells: My), HMC-1-8, MCF-7, MDA- MB-231, MRK-nu-1, SK-BR-3, T-47D, YMB-1-E (hereinafter breast cancer-derived tumor cells: Ma), 786-0, 786-0W, A-704, ACHN, Caki-1, UOK111, UOK121, VMRC-RCW, VMRC-RCZ, EJ-1, T24, TGBC1TKB, TGBC2TKB, TGBC24TKB, HuCCT1, MZChA2, TFK-1, ACS, AGS, GCIY, KATOIII, MKN1, MKN28, MKN74, AsPC-1, BxPC-3, KP4-1, KP4-2, KP4-3, MIAPaCa-2, PANC-1, PK-1, PK-8, PK-9, T3M4, HOS, HuO, MG-63, OST, SaOS-2, TAKAO, Colo320, CW2, DLD-1, C32TG, G-361, LK-2, SBC-2, hu2, GCT-IZ, PC-3, HT-1080 (hereinafter other tumor cells: Others).

Using these tumor cells, a similar test was performed, and TNF-$\alpha_{50}$ value was calculated. The results are shown in FIG. 8G. From these results, it was clarified that lymphoma-derived tumor cells and myeloidic tumor cells show a high activity. That is, it was clarified that the indirect antitumor disordering potency of bisphosphonic acid POM ester derivative is efficiently exhibited in lymphoma-derived tumor cells and myeloidic tumor cells.

Figure 9:
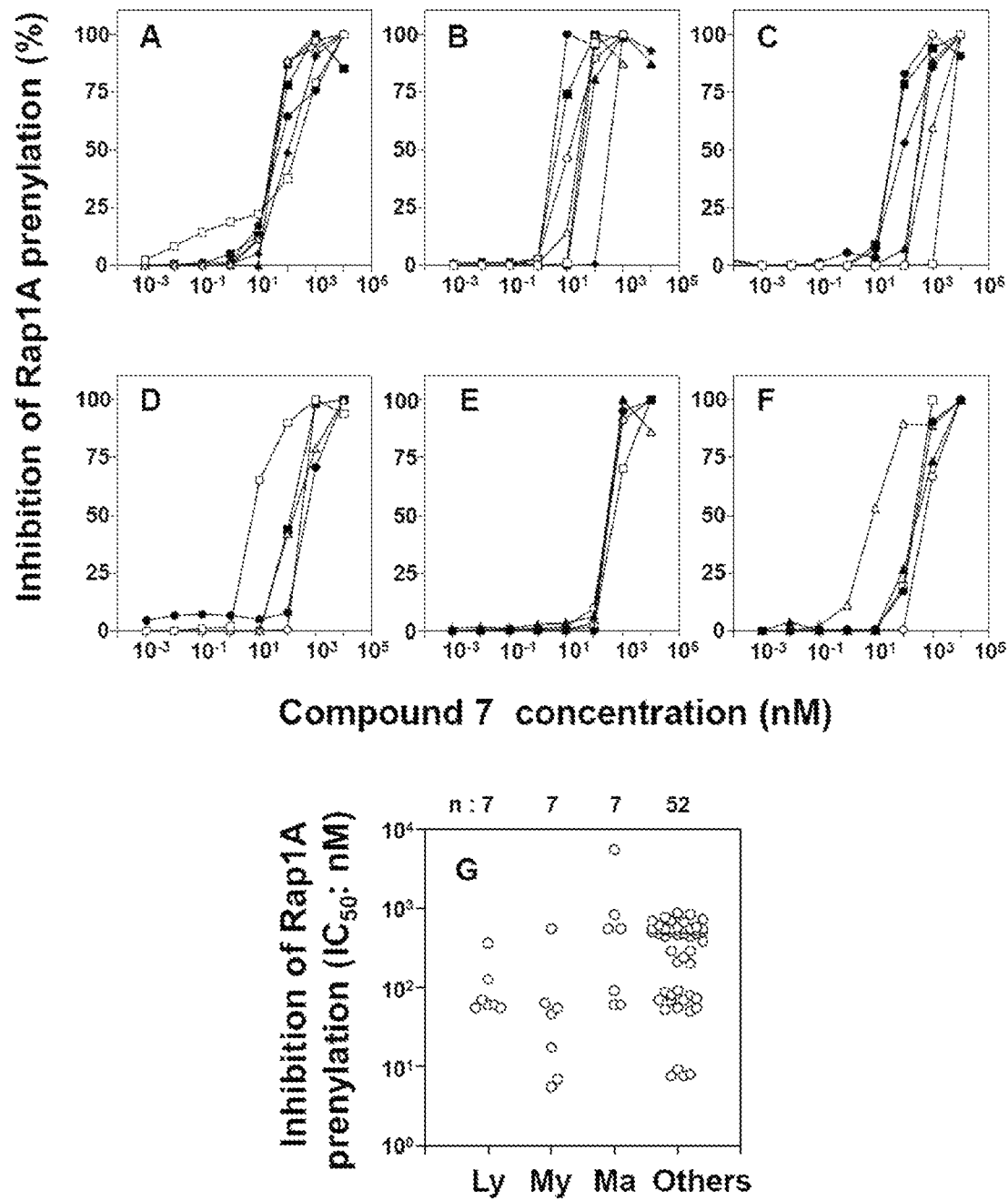
FIG. 9 is a graph showing the results of study of Rap1A geranylgeranylation inhibitory activity of compound 7, which is a bisphosphonic acid POM ester derivative, in various tumor cell lines. FIG. A shows the results in lymphomatous tumor cells (MOLT-3, PEER, C1R, J.RT3-T3.5, Raji, RAMOS-RA1, MOLT-4). FIG. B shows the results in myeloidic tumor cells (HL60, U937, THP-1, SCC-3, P31/FUJ, K562, NOMO-1). FIG. C shows the results in breast cancer-derived tumor cells (YMB-1-E, MRK-nu-1, HMC-1-8, MCF-7, MDA-MB-231, T-47D, SK-BR-3). FIG. D shows the results in renal cancer-derived tumor cells (786-0, VMRC-RCZ, UOK121, Caki-1, A-704). FIG. E shows the results in pancreatic cancer-derived tumor cells (BxPC-3, KP4-1, KP4-2, KP4-3, MiaPaCa-2). FIG. F shows the results in other cancer-derived tumor cells (TGBC24TKB, ACS, MG-63, LK-2, EJ-1). FIG. G shows the results of quantitative study of the action on many kinds of tumor cell lines that underwent a similar test.

Experimental Example 17 (FIG. 9)

From the above-mentioned results of Experimental Example, high indirect cytotoxic ability of bisphosphonic acid POM ester derivative, particularly compound 7, was confirmed. The mechanism thereof is considered to be the following. That is, bisphosphonic acid POM ester derivative is efficiently transferred into the cell, catalyzed by esterase, POM group is deprotected, and converted to the corresponding bisphosphonic acid. Then, the bisphosphonic acid inhibits farnesyl diphosphate synthase, increases intracellular concentration of isopentenyl diphosphate, γδ T cells detects same via butyrophilin 3A1 and affects the tumor cells.

To verify this mechanism, whether the farnesyl diphosphate synthase is inhibited in the cell needs to be confirmed. If farnesyl diphosphate synthase is inhibited, intracellular concentration of geranylgeranyl diphosphate decreases, and geranylgeranylation of Rap1A small G protein is inhibited. The inhibitory effect thereof is clarified by quantifying the inhibition of geranylgeranylation of Rap1A. Therefore, tumor cell is reacted with compound 7, which is a bisphosphonic acid POM ester derivative, and the amount of non-geranylgeranylated Rap1A was examined by the Western blotting method. As the tumor cells, MOLT-3, PEER, C1R, J.RT3-T3.5, Raji, RAMOS-RA1, MOLT-4, HL60, U937, THP-1, SCC-3, P31/FUJ, K562, NOMO-1, YMB-1-E, MRK-nu-1, HMC-1-8, MCF-7, MDA-MB-231, T-47D, SK-BR-3, 786-0, VMRC-RCZ, UOK121, Caki-1, A-704, BxPC-3, KP4-1, KP4-2, KP4-3, MiaPaCa-2, TGBC24TKB, ACS, MG-63, LK-2, EJ-1 were used. These cells were cultured in 90 ml of RPMI1640 medium supplemented with 10% calf serum at 37° C. under 5% $CO_2$ atmosphere while maintaining log phase and using a 225 $cm^2$ flask. Thereto was added 10 mM stock solution of compound 7 to a final concentration of 10 µM, 1 µM, 100 nM, 10 nM, 1 nM, 100 pM, 10 pM, 1 pM. These flasks were cultured at 37° C. under 5% $CO_2$ atmosphere for 16 hr. Non-adherent cells were left unattended, and adherent cells were recovered using EDTA/trypsin solution. The recovered cells were centrifuged at 1,700 rpm, 4° C. for 5 min. The supernatant was removed, and suspended in cell lysis solution (100 µl) composed of 1% NP-40, 0.1% SDS, 0.5% sodium deoxycholate. The suspension was transferred to a 1.5 ml microtube, and centrifuged at 15,000 rpm, 4° C. for 10 min. The supernatant was placed in a different microtube, and a staining solution containing 6.7 M urea, 5% sodium deoxycholate, 100 mM Tris-HCl buffer pH 7.4, 0.25% bromophenol blue, 50 mM DTT was added to make the protein amount 5 mg/ml. The sample was added by 15 µg per lane to 15% polyacrylamide gel, and electrophoresed at 120 mA/h. The protein in the developed gel was transcribed on a polyscreen PVDF membrane, and treated with an anti-Rap1A monoclonal antibody (×500 dilution). The membrane was washed with 5% skim milk, treated with a secondary antibody (×5000 dilution) conjugated to peroxidase, and further washed with 5% skim milk. Thereto was added a chemical chromogenic substrate, and the signal was printed on hyperfilm of Amersham. The thus-obtained signal was subjected to image processing analysis, and the signal was converted into numerical value. The results thereof are shown in FIG. 9A-FIG. 9F.

FIG. 9A shows the results of lymphomatous tumor cells. -●-MOLT-3、-▲-PEER-、-■-C1R、-♦-J. RT3-T3.5、-○-Raji、-Δ-RAMOS-RA1、-□-MOLT-4

FIG. 9B shows the results of myeloidic tumor cells. -●-HL60、-▲-U937、-■-THP-1、-♦-SCC-3、-○-P31/FUJ、-Δ-K562、-□-NOMO-1

FIG. 9C shows the results of breast cancer-derived tumor cells. -●-YMB-1-E、-▲-MRK-nu-1、-■-HMC-1-8、-♦-MCF-7、-○-MDA-MB-231、-Δ-T-47D、-□-SK-BR-3

FIG. 9D shows the results of renal cancer-derived tumor cells. -●-786-0、-▲-VMRC-RCZ、-■-UOK121、-○-Caki-1、-Δ-A-704

FIG. 9E shows the results of pancreatic cancer-derived tumor cells. -●-BxPC-3、-▲-KP4-1、-○-KP4-2、-Δ-KP4-3、-□-MiaPaCa-2、

FIG. 9F shows the results of other cancer-derived tumor cells. -●-TGBC24TKB、-▲-ACS、-○-MG-63、-Δ-LK-2、-□-EJ-1

From these results, it was clarified that compound 7 inhibits efficiently, in any tumor cells, farnesyl diphosphate synthase which is present in the cells. To quantitatively analyze the inhibitory efficiency thereof, the concentration of a compound that inhibits geranylgeranylation of Rap1A by half was calculated as $EC_{50}$ value and studied by comparison. The results are shown in FIG. 9G. The tumor cells studied were as follows.

C1R, RAMOS-RA1, Raji, J.RT3-T3.5, MOLT-3, MOLT-4, PEER (hereinafter lymphomatous tumor cells: Ly), HL60, NOMO-1, SCC-3, THP-1, U937, P31/FUJ, K562 (hereinafter myeloidic tumor cells: My), HMC-1-8, MCF-7, MDA-MB-231, MRK-nu-1, SK-BR-3, T-47D, YMB-1-E (hereinafter breast cancer-derived tumor cells: Ma), 786-0, 786-0W, A-704, ACHN, Caki-1, UOK111, UOK121, VMRC-RCW, VMRC-RCZ, EJ-1, T24, TGBC1TKB, TGBC2TKB, TGBC24TKB, HuCCT1, MZChA2, TFK-1, ACS, AGS, GCIY, KATOIII, MKN1, MKN28, MKN74, AsPC-1, BxPC-3, KP4-1, KP4-2, KP4-3, MIAPaCa-2, PANC-1, PK-1, PK-8, PK-9, T3M4, HOS, HuO, MG-63, OST, SaOS-2, TAKAO, Colo320, CW2, DLD-1, C32TG, G-361, LK-2, SBC-2, hut2, GCT-IZ, PC-3, HT-1080 (hereinafter other tumor cells: Others).

From these results, it was clarified that compound 7 shows a high farnesyl diphosphate synthase inhibitory action in lymphatic tumor cells and myeloidic tumor cells.

Figure 10:
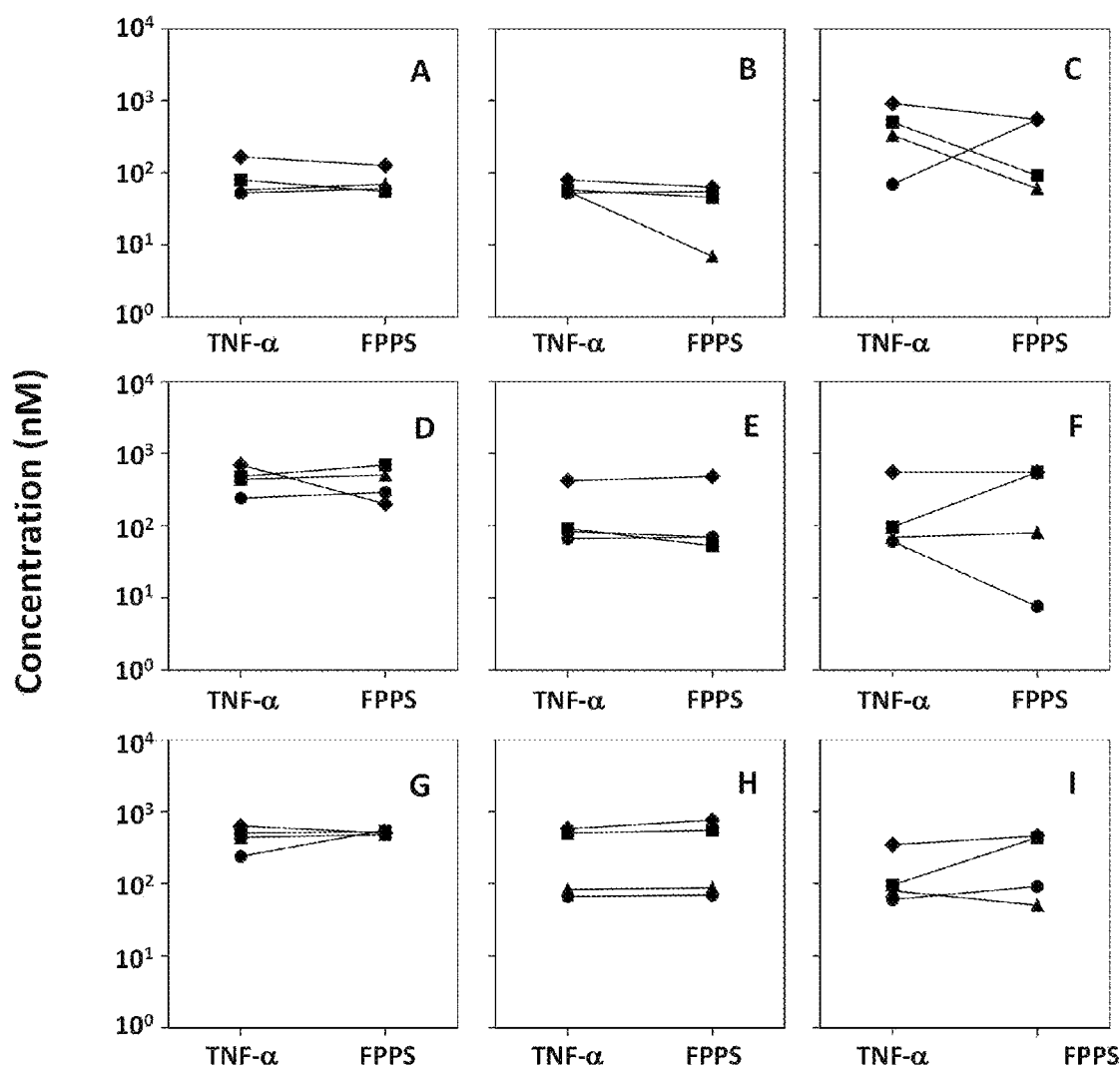
FIG. 10 is a graph showing the measurement results of TNF-$\alpha_{50}$ value as an indirect tumor cytotoxicity action of compound 7, which is a bisphosphonic acid POM ester derivative, on various tumor cell lines and $EC_{50}$ value thereof as a farnesyl diphosphate synthase inhibitory action. FIG. A shows the results on lymphomatous tumor cells (Raji, MOLT-4, PEER, J.RT3-T3.5), FIG. B shows the results on myeloidic tumor cells (HL60, U937, K562, THP-1), FIG. C shows the results on breast cancer-derived tumor cells (T-47D, SK-BR-3, MCF-7, HMC-1-8), FIG. D shows the results on renal cancer-derived tumor cells (VMRC-RCZ, VMRC-RCW, U0K121, A-704), FIG. E shows the results on biliary cancer-derived tumor cells (HuCCT1, TGBC2TKB, TGBC1TKB, TGBC24TKB), FIG. F shows the results on gastric cancer-derived tumor cells (KATOIII, GCIY, ACS, MKN1), FIG. G shows the results on pancreatic cancer-derived tumor cells (BxPC-3, PK-1, KP4-2, KP4-1), FIG. H shows the results on osteosarcoma cell-derived tumor cells (HOS, SaOS2, TAKAO, MG-63), and FIG. I shows the results on other malignant tumor-derived tumor cells (G-361, HT1080, LK-2, Colo320).

Experimental Example 18 (FIG. 10)

The correlation between the indirect tumor cytotoxicity action of compound 7 and the farnesyl diphosphate synthase inhibitory action was studied. To be specific, TNF-$\alpha_{50}$ value as an indirect tumor cytotoxicity action on various tumor cells is compared with $EC_{50}$ value as a farnesyl diphosphate synthase inhibitory action, and summarized in FIG. 10A-FIG. 10I.

FIG. 10A shows the results of lymphomatous tumor cells.

-●-Raji、-▲-MOLT-4、-■-PEER、-♦-J. RT3-T3.5

FIG. 10B shows the results of myeloidic tumor cells.

-●-HL60、-▲-U937、-■-K562、-♦-THP-1

FIG. 10C shows the results of breast cancer-derived tumor cells.

-●-T-47D、-▲-SK-BR-3、-■-MCF-7、-♦-HMC-1-8

FIG. 10D shows the results of renal cancer-derived tumor cells.

-●-VMRC-RCZ、-▲-VMRC-RCW、-■-UOK121、-♦-A-704

FIG. 10E shows the results of biliary cancer-derived tumor cells.

-●-HuCCT1、-▲-TGBC2TKB、-■-TGBC1TKB、-♦-TGBC24TKB

FIG. 10F shows the results of gastric cancer-derived tumor cells.

-●-KATOIII、-▲-GCIY、-■-ACS、-♦-MKN1

FIG. 10G shows the results of pancreatic cancer-derived tumor cells.

-●-BxPC-3、-▲-PK-1、-■-KP4-2、-♦-KP4-1

FIG. 10H shows the results of osteosarcoma cell-derived tumor cells.

-●-HOS、-▲-SaOS2、-■-TAKAO、-♦-MG-63

FIG. 10I shows the results of other malignant tumor-derived tumor cells.

-●-G-361、-▲-HT1080、-■-LK-2、-♦-Colo320

TNF-$\alpha_{50}$ value and $EC_{50}$ value were compared in each case.

As is clear from FIG. 10, in any tumor cell line, TNF-$\alpha_{50}$ value and $EC_{50}$ value are almost the same, from which it is strongly suggested that compound 7 enters into a cell, is converted by esterase into an active bisphosphonic acid, which inhibits farnesyl diphosphate synthase, and an increase in the intracellular concentration of the resulting isopentenyl diphosphate is detected by γδ T cells via butyrophilin 3A1 and tumor cytotoxicity is exhibited.

Figure 11:
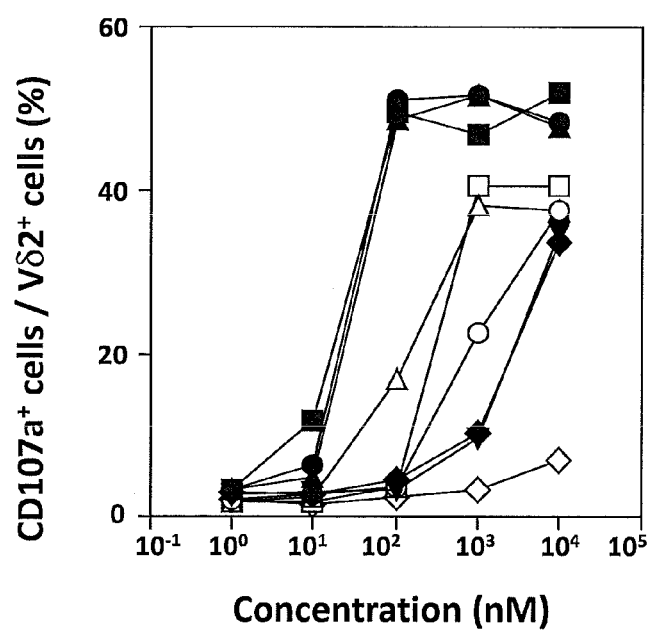
FIG. 11 is a graph showing the results of study of tumor cytotoxicity induction ability of bisphosphonic acid ester derivatives (compounds 43-50) such as BuOM and the like different from POM. The tumor cytotoxicity induction action was evaluated by measuring the ratio of CD107a positive cells in Vδ2 positive cells.

Experimental Example 19 (FIG. 11)

Then, not only the bisphosphonic acid POM ester derivatives but also different ester derivatives such as BuOM and the like were studied for the tumor cytotoxicity induction action. As the bisphosphonic acid ester derivative, compounds 43-50 were used. First, U937 was cultured in RPMI1640 medium supplemented with 10% calf serum at 37° C. under 5% $CO_2$ atmosphere while maintaining log phase. Respective cells were recovered, and centrifuged at 1,700 rpm, 4° C. for 5 min. The supernatant was removed, suspended in RPMI1640 medium supplemented with 10% calf serum to 2×10$^5$ cells/200 μl, and dispensed to a round-bottomed 96 well plate by 200 μl. The plate was centrifuged at 1,700 rpm, 4° C. for 2 min, and the supernatant was removed. Then, various compounds were prepared at 10 μM, 1 μM, 100 nM, 10 nM, 1 nM and added to the cells by 200 μl each. The plate was incubated at 37° C. under 5% $CO_2$ atmosphere for 2 hr, and wash 5 times with 200 μl of medium. Then, γδ T cells prepared to 2×10$^5$ cells/50 μl were added by 50 μl. Furthermore, 5 μl of PE-labeled anti-CD107a monoclonal antibody was added. The plate was incubated at 37° C. under 5% $CO_2$ atmosphere for 2 hr and, after ice-cooling, 2 μl of FITC-labeled anti-Vδ2 antibody was added. After ice-cooling for 15 min, the cells were washed with 200 μl of PBS added with 2% calf fetal serum, and analyzed by a flow cytometer. The ratio of CD107a positive cells in Vδ2 positive cells was plotted in FIG. 11. In FIG. 11, each symbol shows the following.

-●- compound 7, -▲- compound 43, -■- compound 44, -♦- compound 45, -▼- compound 46, -○- compound 47, -Δ- compound 48, -□- compound 49, -◇- compound 50

From these results, it was shown that various bisphosphonic acid ester derivatives show tumor cytotoxicity.

Figure 12:
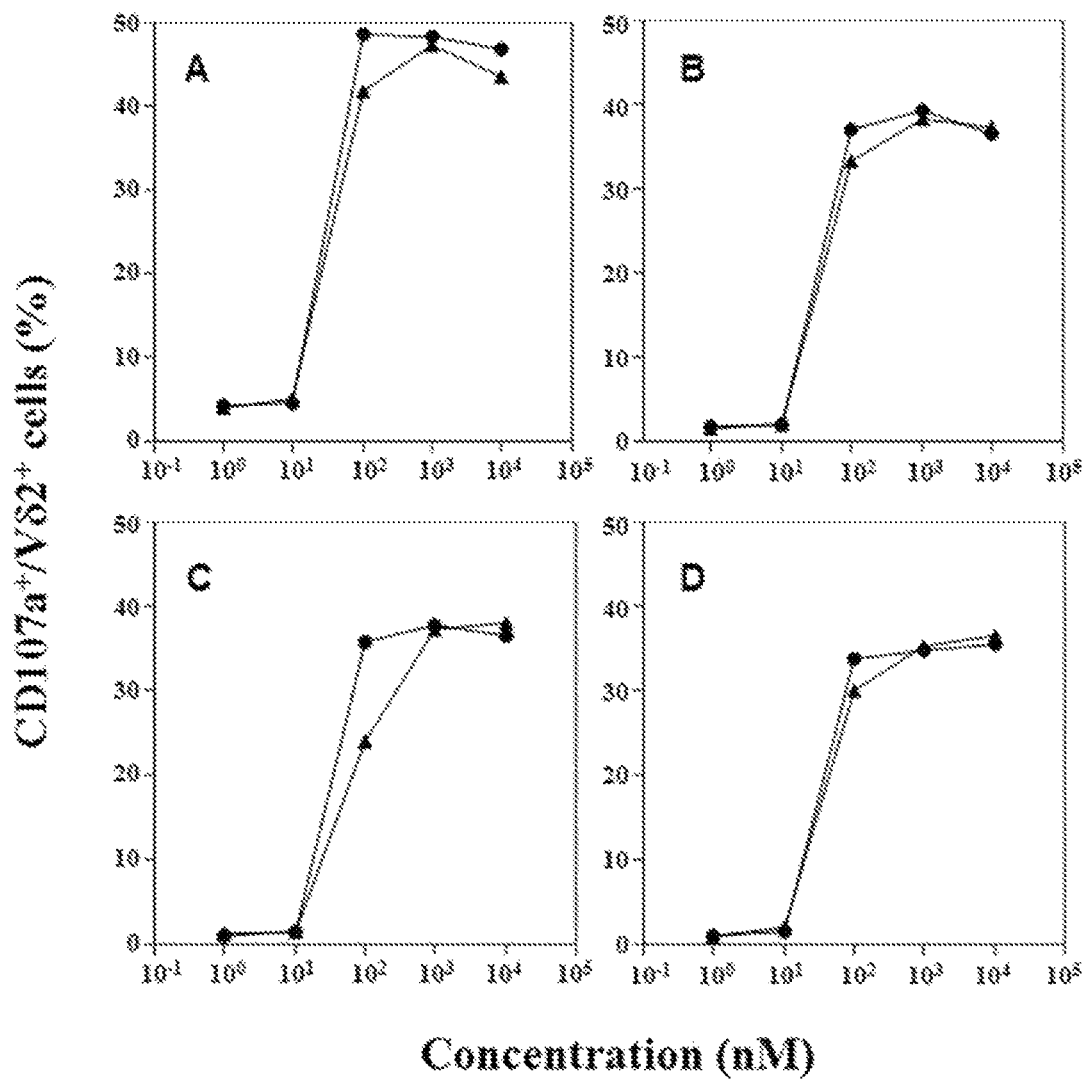
FIG. 12 shows the study of indirect cytotoxic induction ability of compound 7 and compound 44, which are bisphosphonic acid ester derivatives, in HTLV-1 virus infected cells. The cytotoxicity induction action was evaluated by measuring the ratio of CD107a positive cells in Vδ2 positive cells. As the HTLV-1 infected cells, TL-Su, HCT-1, HCT-4, and HCT-5 were used.

Experimental Example 20 (FIG. 12)

Then, compounds 7 and 44 as bisphosphonic acid ester derivatives were studied for an indirect cytotoxicity induction ability against HTLV-1 virus infected cells. First, TL-Su, HCT-1, HCT-4, HCT-5 (each obtained from Dr. Tatsufumi Nakamura, First Department of Internal Medicine Nagasaki University) as HTLV-1-infected cells were cultured in RPMI1640 medium supplemented with 10% calf serum in the presence of 100 U/ml IL-2 at 37° C. under 5% $CO_2$ atmosphere while maintaining log phase. Respective cells were recovered, and centrifuged at 1,700 rpm, 4° C. for 5 min. The supernatant was removed, suspended in RPMI1640 medium supplemented with 10% calf serum to 2×10$^5$ cells/200 μl, and dispensed to a round-bottomed 96 well plate by 200 μl. The plate was centrifuged at 1,700 rpm, 4° C. for 2 min, and the supernatant was removed. Then, various compounds were prepared at 10 μM, 1 μM, 100 nM, 10 nM, 1 nM and added to the cells by 200 μl each. The plate was incubated at 37° C. under 5% $CO_2$ atmosphere for 2 hr, and wash 5 times with 200 μl of medium. Then, γδ T cells prepared to 2×10$^5$ cells/50 μl were added by 50 μl. Furthermore, 5 μl of PE-labeled anti-CD107a monoclonal antibody was added. The plate was incubated at 37° C. under 5% $CO_2$ atmosphere for 2 hr and, after ice-cooling, 2 μl of FITC-labeled anti-Vδ2 antibody was added. After ice-cooling for 15 min, the cells were washed with 200 μl of PBS added with 2% calf fetal serum, and analyzed by a flow cytometer. The ratio of CD107a positive cells in Vδ2 positive cells was plotted in FIG. 12. As the HTLV-1-infected cells, TL-Su (FIG. 12A), HCT-1 (FIG. 12B), HCT-4 (FIG. 12C) and HCT-5 (FIG. 12D) were each used. In FIG. 12, each symbol shows the following.

-●- compound 7, -▲- compound 44

As is clear from FIG. 12, it was confirmed that POM ester derivative and BuOM ester derivative of bisphosphonic acid have an action to induce indirect cytotoxicity against virus infected cells such as HTLV-1-infected cells and the like.

Figure 13:
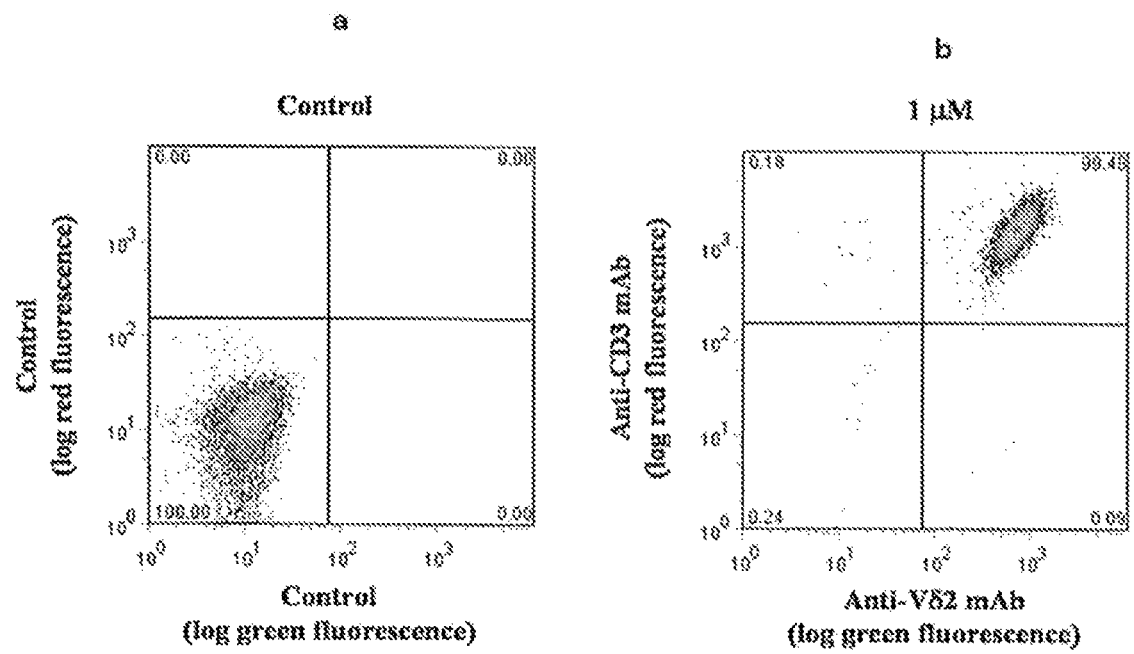
FIG. 13 shows induction ratio of γδ T cells in normal adult-derived peripheral blood mononuclear cells when compound 7, which is a bisphosphonic acid POM ester derivative, was used.

Experimental Example 21 (FIG. 13)

Measurement of Induction Ratio in γδ T Cells

Mononuclear cells were obtained by the specific gravity centrifugation method from the peripheral blood of a healthy adult. The obtained mononuclear cells were suspended in Yssel medium at 1.8×10$^6$ cells/ml, and seeded by 1.5 ml in each well of a 24-well plate. Compound 7 was added to each well at a concentration of 1 μM, and cultured at 37° C. under 5% $CO_2$ atmosphere. After one day of culture, IL-2 was added at a concentration of 100 IU/ml, and the cells were cultured in the presence of 100 IU/ml IL-2 thereafter up to day 6, and cultured in the presence of 30 IU/ml IL-2 from day 7. After 14 days of culture, the cells were recovered, and cell surface molecule was analyzed by flow cytometry using labeled anti-CD3 antibody and labeled anti-Vδ2 antibody. As a control, an antibody having the same isotype as anti-CD3 antibody and anti-Vδ2 antibody but irrelevant thereto was used. The ratio (%) of γδ T cells having the Vδ2 region in CD3 cells was determined.

The results thereof are shown in FIG. 13. The ratio of the cells having the Vδ2 region increased in the presence of compound 7, and induction of γδ T cells was confirmed. Almost all cells (99.8%) were γδ T cells at 1 μM, it was found that γδ T cells were specifically induced and/or proliferated.

Figure 14:
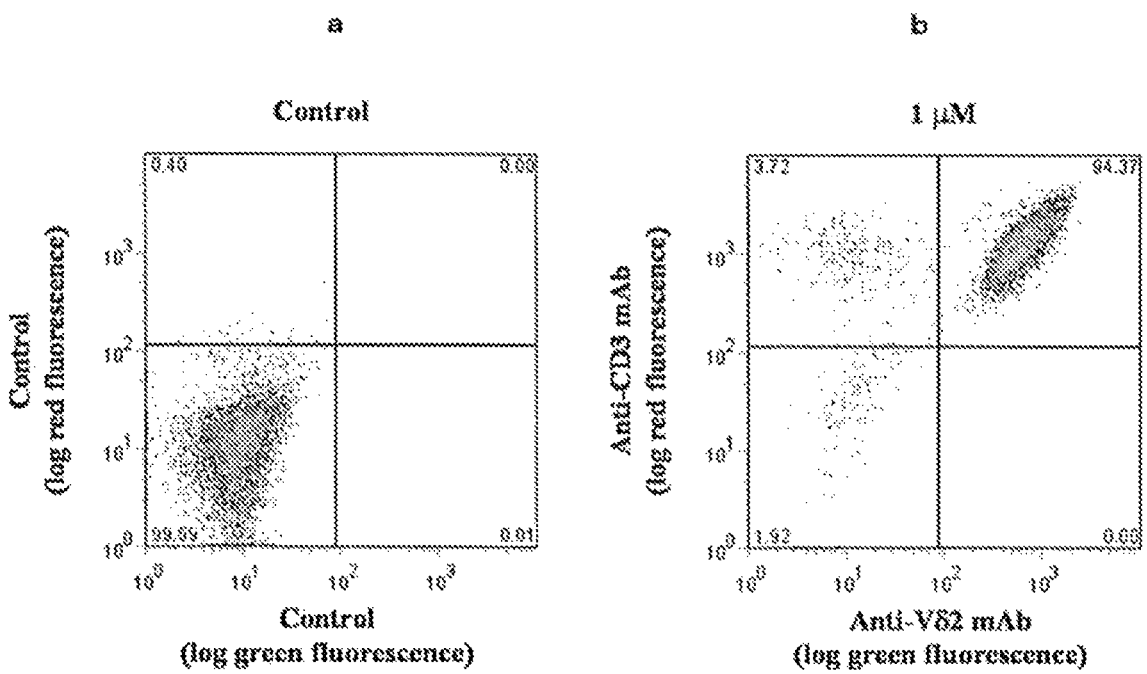
FIG. 14 shows induction ratio of γδ T cells in breast cancer patient-derived peripheral blood mononuclear cells when compound 7, which is a bisphosphonic acid POM ester derivative, was used.

Experimental Example 22 (FIG. 14)

Measurement of Induction Ratio in γδ T Cells

In the same manner as in Experimental Example 21 except that mononuclear cells obtained from the peripheral blood of breast cancer patients were used, compound 7 was added, and the cells were cultured at 37° C. under 5% $CO_2$ atmosphere. IL-2 was added at a concentration of 30 IU/ml on day 2 and day 3, and the cells were cultured at a concentration of 100 IU/ml from day 4. After 17 days of culture, the cells were recovered, and cell surface molecule was analyzed by flow cytometry in the same manner as in Experimental Example 21. Also, the ratio (%) of γδ T cells having the Vδ2 region in CD3 cells was determined.

The results thereof are shown in FIG. 14. It was found that γδ T cells having a high purity of not less than 96% were obtained even in the peripheral blood of cancer-carrying patients.

Experimental Example 23 (Table 9)

Study of Solubilizer of a Bisphosphonic acid ester Derivative

Trimethyl β-cyclodextrin (hereinafter to be also referred to as "TMβCD") (Tokyo Chemical Industry Co., Ltd.), dimethyl β-cyclodextrin (hereinafter to be also referred to as "DMβCD") (Tokyo Chemical Industry Co., Ltd.), Tween80 (Tokyo Chemical Industry Co., Ltd.), HCO-60 (trade name: Nikko Chemicals Co., Ltd.) (PEG-60 hydrogenated castor oil) as solubilizers were dissolved in ethanol (EtOH) (10 ml), bisphosphonic acid ester derivative compound 7 (7.4 mg) was added and mixed well, and the mixture was 10-fold diluted with saline, and the stability of each solution was observed at room temperature.

The results are shown in Table 9.

TABLE 9

| solubilizer | amount necessary for solubilization | stability |
| --- | --- | --- |
| TMβCD:143 mg | 10 molar equivalents | no precipitation for one week or longer and transparency maintained |
| DMβCD:133 mg | 10 molar equivalents | no precipitation for one week or longer and transparency maintained |
| Tween 80:1.3 g | 100 molar equivalents | precipitated one week later |
| HCO-60:3.5 g | 100 molar equivalents | precipitated one week later |

Unalkylated βCD was not dissolved in EtOH. When a solution of unalkylated βCD in saline was mixed with a solution of bisphosphonic acid ester derivative in EtOH solution, precipitates were produced.

From the above, it was clarified that solubilization of hardly water-soluble bisphosphonic acid ester derivative by alkylated cyclodextrin can be performed with a small amount as compared to other surfactants, and such mixed solution is also superior in stability.

Figure 15:
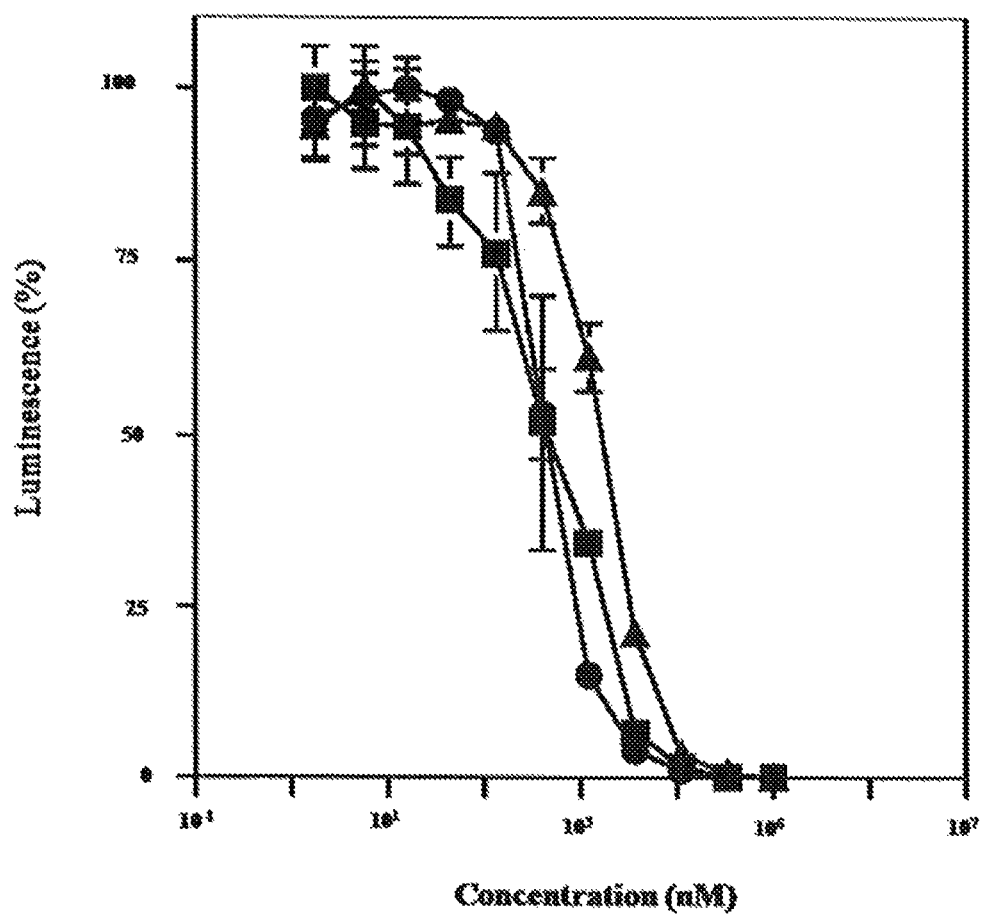
FIG. 15 shows inhibition of proliferation of bladder cancer cell line EJ-1 in a mixed solution containing compound 7, which is a bisphosphonic acid POM ester derivative, and alkylated βCD.

Experimental Example 24 (FIG. 15)

Study of Inhibition of Proliferation of Bladder Cancer Cell Line EJ-1 by Mixed Solution Containing bisphosphonic acid ester Derivative and alkylated βCD The property of randomly dimethylated βCD (DMβCD) and completely trimethylated βCD (TMβCD) as solubilizers in the solubilization of bisphosphonic acid ester derivative was studied. Compound 7 was used as a bisphosphonic acid ester derivative, and DMSO was used as a control solubilizer.

First, a mixed solution of a bisphosphonic acid ester derivative and DMβCD or TMβCD was prepared, reacted with EJ-1 at various concentration of 33.33 nM and an influence thereof on the cell proliferation was studied.

A mixed solution of a bisphosphonic acid ester derivative and DMβCD or TMβCD was prepared as follows. A 10 mM ethanol solution of DMβCD or TMβCD is prepared. A bisphosphonic acid ester derivative (compound 7) is added at 1 mM, and the mixture is mixed well. These were used as "7/DMβCD" solution and "7/TMβCD" solution. The solutions can be preserved at −30° C. When in use, it is diluted with saline or a medium to 100 pM to 1 μM based on the bisphosphonic acid ester derivative. A DMSO solution of a bisphosphonic acid ester derivative was "7/DMSO" solution.

A cell proliferation test was performed as follows.
First, EJ-1 was cultured in RPMI1640 medium supplemented with 10% calf serum (complete RPMI1640 medium) up to immediately before confluence. Then, the cells were recovered with 0.25% trypsin/EDTA, washed with complete RPMI1640 to give cell suspension ($1 \times 10^4$ cells/ml). This was seeded by 50 μl in a 96-well flat bottom plate, and adjusted to secure $5 \times 10^2$ cells in each well. Thereto was added 7/DMSO, 7/DMβCD or 7/TMβCD, which was 3-fold series diluted from 2 mM, by 50 μl each to set the final concentration to one-third series diluted from 1 mM. The plate was cultured at 37° C. under 5% $CO_2$ atmosphere for 4 days, and the viable cell number was measured (n=3) as the ATP content. As the ATP measurement method, a standard quantification method using luciferin luciferase was used. The luminescence level was measured by a luminometer. Taking the value obtained from the medium control as 100%, the inhibition of cell proliferation was shown using the ratio to the medium control.

In FIG. 15, the definition of each symbol is as follows.
-●- is 7/DMSO, -▲- is 7/DMβCD, -■- is 7/TMβCD 7/TMβCD and 7/DMSO showed almost equivalent bladder cancer intracellular transferability, and $IC_{50}$ relative to EJ-1 was several hundred nM. On the other hand, 7/DMβCD showed bladder cancer intracellular transferability of about one-tenth thereof. Therefore, it was clarified that alkylated cyclodextrin, particularly 7/TMβCD, has a superior pharmacological action of the same level as 7/DMSO.

Figure 16:
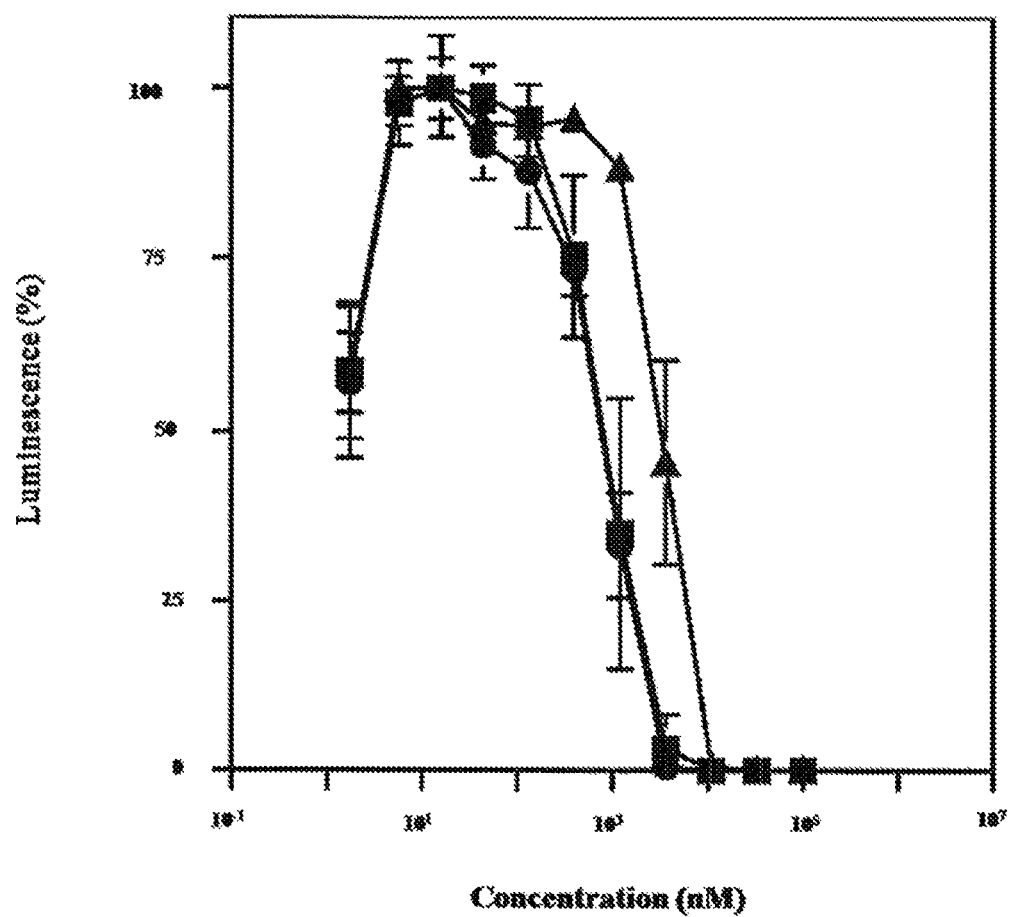
FIG. 16 shows inhibition of proliferation of monocyte tumor cell line U937 in a mixed solution containing compound 7, which is a bisphosphonic acid POM ester derivative, and alkylated βCD.

Experimental Example 25 (FIG. 16)

Study of Inhibition of Proliferation of monocyte Tumor Cell Line U937 by Mixed Solution Containing bisphosphonic acid ester Derivative and alkylated βCD The property of DMβCD and TMβCD as solubilizers was studied in the same manner as in Experimental Example 24, by using monocyte tumor cell line U937 and DMSO as a control of the solubilizer. First, using compound 7 as a bisphosphonic acid ester derivative, 7/DMβCD and 7/TMβCD was prepared in the same manner as in Experimental Example 24, reacted with U937 at various concentrations, and an influence thereof on the cell proliferation was studied.

U937 was cultured in RPMI1640 medium up to immediately before confluence. This was resuspended in new complete RPMI1640 medium to give a cell suspension ($1 \times 10^4$ cells/ml). This was seeded by 50 μl in a 96-well flat bottom plate, and adjusted to secure $5 \times 10^2$ cells in each well. Thereto was added 7/DMSO, 7/DMβCD or 7/TMβCD, which was 3-fold series diluted from 2 mM, by 50 μl each to set the final concentration to one-third series diluted from 1 mM. The plate was cultured at 37° C. under 5% $CO_2$ atmosphere for 4 days, and the viable cell number was measured (n=3) as the ATP content. As the ATP measurement method, a standard quantification method using luciferin luciferase was used.

In FIG. 16, the definition of each symbol is as follows. -●- is 7/DMSO, -▲- is 7/DMβCD, -■- is 7/TMβCD Similar to Experimental Example 24, 7/TMβCD and 7/DMSO showed almost equivalent monocyte tumor intracellular transferability, and $IC_{50}$ relative to U937 was several hundred nM. On the other hand, 7/DMβCD showed, similar to Experimental Example 24, monocyte tumor intracellular transferability of about one-tenth thereof. From the results, similar to Experimental Example 24, it was clarified that alkylated cyclodextrin, particularly 7/TMβCD, has a superior pharmacological action of the same level as 7/DMSO.

Figure 17:
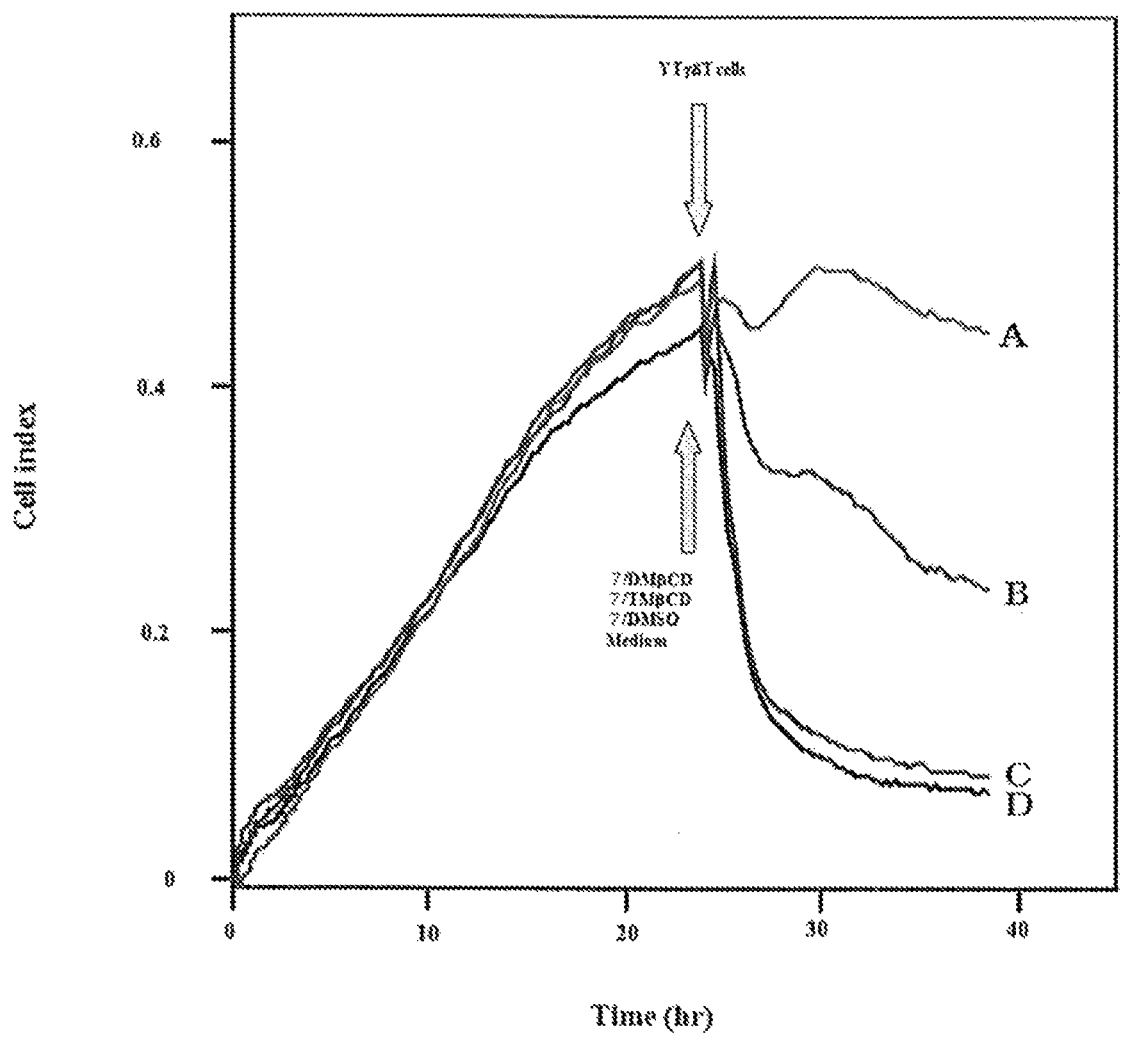
FIG. 17 shows cytotoxicity activity of peripheral blood γδ T cells of healthy adult against bladder cancer cell line EJ-1 pre-treated with a mixed solution containing compound 7, which is a bisphosphonic acid POM ester derivative, and alkylated βCD.

Experimental Example 26 (FIG. 17)

Study of cytotoxicity Activity of γδ T Cells in Peripheral Blood of Healthy Adult on Bladder Cancer Cell Line EJ-1 Pre-Treated with Mixed Solution Containing bisphosphonic acid ester Derivative and alkylated βCD To study the property of DMβCD and TMβCD as solubilizers, 7/DMSO, 7/DMβCD and 7/TMβCD were prepared using compound 7 as a bisphosphonic acid ester derivative, and reacted with bladder cancer cell line EJ-1 at the final concentration of 33.33 nM. Furthermore, healthy adult peripheral blood-derived γδ T cells were reacted and the cytotoxicity thereof was studied.

First, 7/DMSO, 7/DMβCD and 7/TMβCD were prepared in the same manner as in Experimental Example 24. A cytotoxicity test was performed as follows. EJ-1 was cultured in complete RPMI1640 medium up to immediately before confluence. Then, the cells were recovered using 0.25% trypsin/EDTA, and washed with complete RPMI1640 to give a cell suspension ($3 \times 10^4$ cells/ml). Here, the baseline impedance of a 96-well E-plate added with 100 μl of complete RPMI1640 medium was measured. After the measurement of the baseline, the cell suspension was seeded by 100 μl in a 96-well flat bottom E-plate, and adjusted to ensure $3 \times 10^3$ cells in each well. This plate was cultured at 37° C. under 5% $CO_2$ atmosphere for 24 hr, and the impedance was measured every 15 min. The 50 μl of the medium was removed from each well, and 7/DMSO, 7/DMβCD or 7/TMβCD was added by 50 μl to make the final concentration of bisphosphonic acid ester derivative 33.33 nM. As a control, a well added with 50 μl of the medium was also prepared. To transfer the medicament into tumor cells, the plate was incubated at 37° C. under 5% $CO_2$ atmosphere for 14 hr more. The cell proliferation of EJ-1 is shown as an increase in the impedance (cell index), and EJ-1 cytotoxicity by γδ T cells is shown as a decrease in the impedance.

In FIG. 17, A shows a medium-added treatment control, B shows 7/DMβCD treatment, C shows 7/TMβCD treatment, and D shows 7/DMSO treatment, and the vertical axis shows viable cell number (impedance), and the horizontal axis shows time. The position of arrow shows the time when each medicament solution was added. FIG. 17 shows representative experiment results in 10 times of independent experiments. EJ-1 treated with 7/TMβCD or 7/DMSO showed almost equivalent sensitivity relative to the cytotoxicity potency of γδ T cells, and it was clarified that γδ T cells can be sufficiently immunized at 33.33 nM based on the concentration of bisphosphonic acid ester derivative. On the other hand, 7/DMβCD showed intracellular transferability of about one-tenth thereof. From the results, it was clarified that alkylated cyclodextrin, particularly 7/TMβCD, has a superior pharmacological action of the same level as 7/DMSO.

Figure 18:
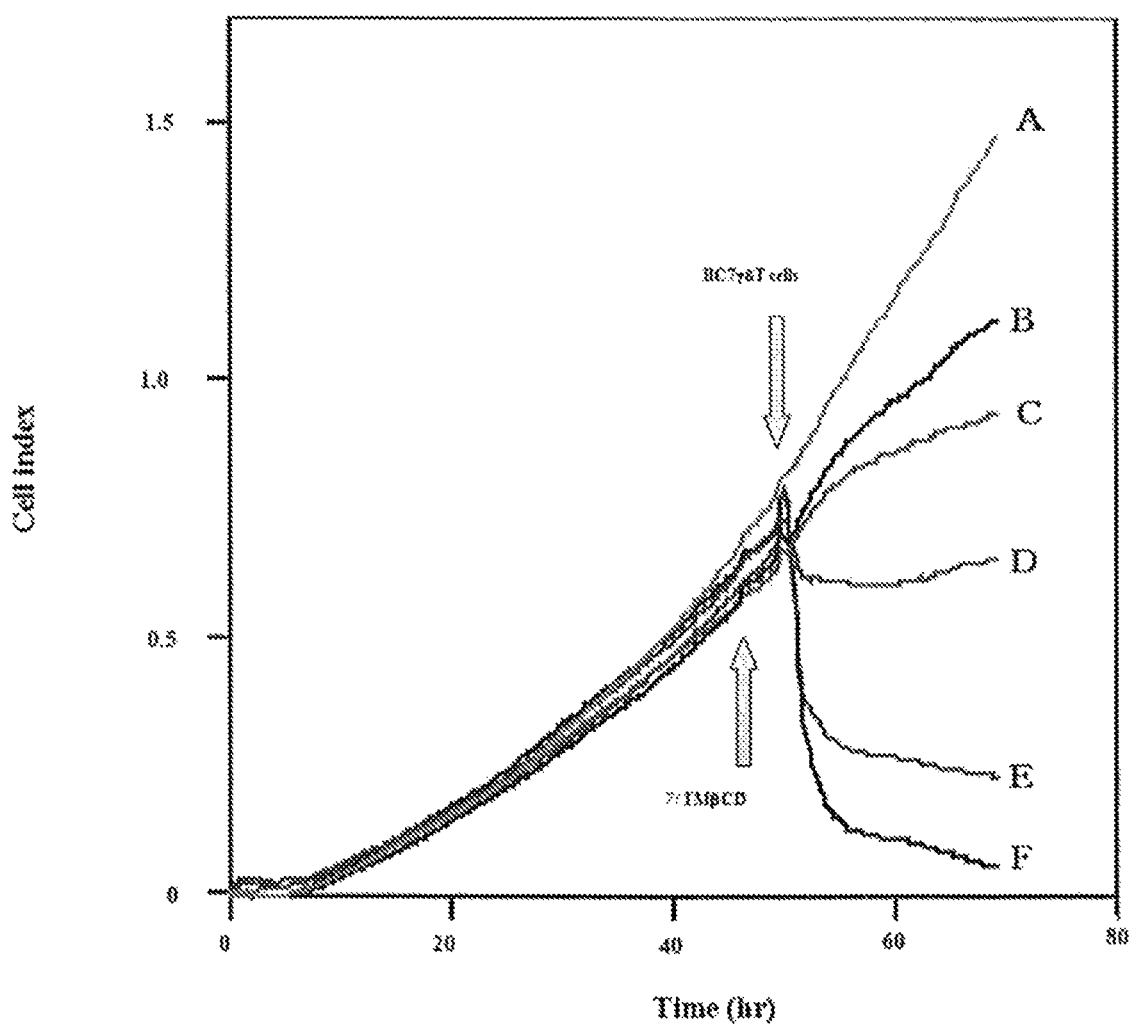
FIG. 18 shows cytotoxicity activity of peripheral blood γδ T cell BC7 of breast cancer patient against breast cancer cell line T-47D pre-treated with a mixed solution containing compound 7, which is a bisphosphonic acid POM ester derivative, and alkylated βCD.

Experimental Example 27 (FIG. 18)

Study of cytotoxicity Activity of γδ T Cells in Peripheral Blood of Breast Cancer Patient on Breast Cancer Cell Line T-47D Pre-Treated with Mixed Solution Containing bisphosphonic acid ester Derivative and alkylated βCD To study the property of 7/TMβCD, it was reacted with breast cancer cell T-47D at various concentrations. Furthermore, peripheral blood-derived γδ T cells of breast cancer patient were reacted and the cytotoxicity thereof was studied.

Using compound 7 as a bisphosphonic acid ester derivative and TMβCD as a solubilizer, 7/TMβCD was prepared in the same manner as in Experimental Example 24. A cytotoxicity test was performed as follows. T-47D was cultured in complete RPMI1640 medium up to immediately before confluence. Then, the cells were recovered using 0.25% trypsin/EDTA, and washed with complete RPMI1640 to give a cell suspension ($5 \times 10^4$ cells/ml). Here, the baseline impedance of a 96-well E-plate added with 100 μl of complete RPMI1640 medium was measured. After the measurement of the baseline, the cell suspension was seeded by 100 μl in a 96-well flat bottom E-plate, and adjusted to ensure $5 \times 10^3$ cells in each well. This plate was cultured at 37° C. under 5% $CO_2$ atmosphere for 46.5 hr, and the impedance was measured every 15 min. The 50 μl of the medium was removed from each well, and 7/TMβCD was added by 50 μl to make the final concentration of compound 7 0 nM, 1.56 nM, 12.5 nM, 25 nM, 50 nM. To transfer the medicament into tumor cells, the plate was incubated at 37° C. under 5% $CO_2$ atmosphere for 3.5 hr more. Then, the culture medium was removed by 50 μl from each well, and 50 μl of γδ T cells derived from the peripheral blood of a breast cancer patient, which was suspended at $1 \times 10^5$ cells/50 μl, was added. As a control, a well treated with 50 nM 7/TMβCD and added with complete RPMI1640 medium instead of γδ T cells was also prepared. While measuring changes in the impedance every 15 min, the plate was incubated for 15 hr more at 37° C. under 5% $CO_2$ atmosphere. The cell proliferation of T-47D is shown as an increase in the impedance, and T-47D cytotoxicity by γδ T cells is shown as a decrease in the impedance.

In FIG. 18, A shows 50 nM 7/TMβCD+medium, B shows 0 nM 7/TMβCD+γδ T cells, C shows 1.56 nM 7/TMβCD+γδ T cells, D shows 12.5 nM 7/TMβCD+γδ T cells, E shows 25 nM 7/TMβCD+γδ T cells, F shows 50 nM 7/TMβCD+γδ T cells, and the vertical axis shows viable cell number (impedance), and the horizontal axis shows time. The position of arrow shows the time when each medicament solution was added. FIG. 18 shows representative experiment results in 10 times of independent experiments. T-47D treated with 7/TMβCD showed sensitivity in a medicament concentration dependent manner relative to the cytotoxicity potency of γδ T cells, and it was clarified that γδ T cells can be sufficiently immunized at 25 nM based on the concentration of bisphosphonic acid ester derivative. From the results, it was clarified that 7/TMβCD is superior in intracellular transferability and has a remarkable pharmacological action.

INDUSTRIAL APPLICABILITY

The novel bisphosphonic acid ester derivatives of the present invention exhibit a superior direct tumor cytotoxicity effect and a superior virus-infected cell cytotoxicity effect. By efficiently increasing the intracellular level of isopentenyl diphosphate to be a substrate of farnesyl diphosphate synthase, activation of γδ T cells via butyrophilin 3A1 is induced, and an efficient indirect tumor cytotoxicity effect and an efficient virus-infected cell cytotoxicity effect, via an immune effect, are exhibited.

This application is based on a patent application No. 2014-257451 filed in Japan (filing date: Dec. 19, 2014), the contents of which are incorporated in full herein.

The invention claimed is:

1. A bisphosphonic acid ester derivative selected from the group consisting of

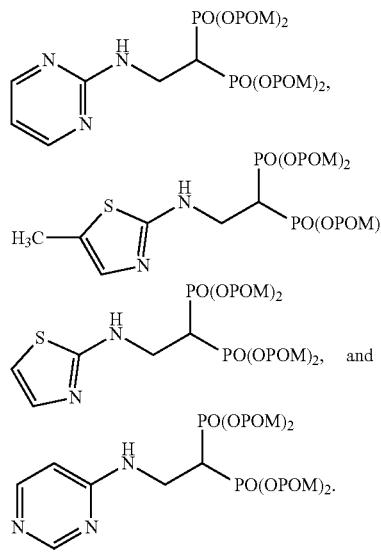

2. A pharmaceutical composition comprising the bisphosphonic acid ester derivative according to claim 1 as an active ingredient.

3. The pharmaceutical composition according to claim 2 further comprising alkylated cyclodextrin.

4. The pharmaceutical composition according to claim 3, wherein the alkylated cyclodextrin is trimethyl-β-cyclodextrin.

5. The pharmaceutical composition according to claim 2, wherein the bisphosphonic acid ester derivative is at least one selected from an anti-tumor cell agent, an antiproliferative agent and/or cytotoxic agent for a virus infected cell, and an agent for proliferation and/or induction of γδ type T cells.

6. The pharmaceutical composition according to claim 3, wherein the bisphosphonic acid ester derivative is at least one selected from an anti-tumor cell agent, an antiproliferative agent and/or cytotoxic agent for a virus infected cell, and an agent for proliferation and/or induction of γδ type T cells.

7. The pharmaceutical composition according to claim 4, wherein the bisphosphonic acid ester derivative is at least one selected from an anti-tumor cell agent, an antiproliferative agent and/or cytotoxic agent for a virus infected cell, and an agent for proliferation and/or induction of γδ type T cells.

8. A method of dissolving a bisphosphonic acid ester derivative comprising:
    (a) dissolving alkylated cyclodextrin in a water-soluble organic solvent to provide dissolved alkylated cyclodextrin in a water-soluble organic solvent, and
    (b) mixing the bisphosphonic acid ester derivative of claim 1 with the dissolved alkylated cyclodextrin in a water-soluble organic solvent.

9. The method according to claim 8, wherein the alkylated cyclodextrin is trimethyl-β-cyclodextrin.

10. The bisphosphonic acid ester derivative according to claim 1, wherein the bisphosphonic acid ester derivative is

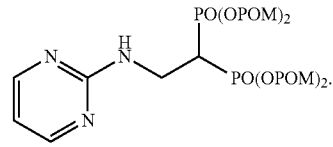

11. The bisphosphonic acid ester derivative according to claim 1, wherein the bisphosphonic acid ester derivative is

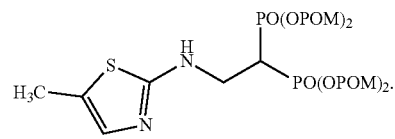

12. The bisphosphonic acid ester derivative according to claim 1, wherein the bisphosphonic acid ester derivative is

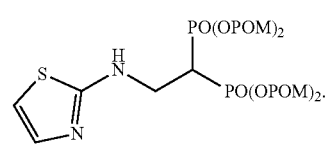

13. The bisphosphonic acid ester derivative according to claim 1, wherein the bisphosphonic acid ester derivative is

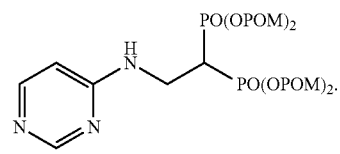

14. A pharmaceutical composition comprising the bisphosphonic acid ester derivative according to claim 10 as an active ingredient.

15. A pharmaceutical composition comprising the bisphosphonic acid ester derivative according to claim 11 as an active ingredient.

16. A pharmaceutical composition comprising the bisphosphonic acid ester derivative according to claim 12 as an active ingredient.

17. A pharmaceutical composition comprising the bisphosphonic acid ester derivative according to claim 13 as an active ingredient.

* * * * *